(12) United States Patent
Gammie et al.

(10) Patent No.: US 11,872,133 B1
(45) Date of Patent: Jan. 16, 2024

(54) VALVE TRANSLOCATION DEVICE AND METHOD FOR THE TREATMENT OF FUNCTIONAL VALVE

(71) Applicants: University of Maryland, Baltimore, Baltimore, MD (US); University of Maryland Medical System LLC, Baltimore, MD (US)

(72) Inventors: James Gammie, Stevenson, MD (US); Rachael Quinn, Abingdon, MD (US); Chetan Pasrija, Gaithersburg, MD (US)

(73) Assignee: University of Maryland, Baltimore; University of Maryland Medical System LLC, Baltimore, MD (US)

(*) Notice: Subject to any disclaimer, the term of this patent is extended or adjusted under 35 U.S.C. 154(b) by 0 days.

(21) Appl. No.: 17/816,080

(22) Filed: Jul. 29, 2022

Related U.S. Application Data

(63) Continuation of application No. 17/584,157, filed on Jan. 25, 2022, which is a continuation of application No. 16/888,322, filed on May 29, 2020, now Pat. No. 11,259,925, which is a continuation of application No. PCT/US2020/031110, filed on May 1, 2020, said application No. 17/584,157 is a continuation-in-part of application No. 16/761,181, filed as application No. PCT/US2018/059253 on Nov. 5, 2018, now abandoned.

(60) Provisional application No. 62/842,085, filed on May 2, 2019, provisional application No. 62/581,085, filed on Nov. 3, 2017.

(51) Int. Cl.
    *A61F 2/24* (2006.01)

(52) U.S. Cl.
    CPC .......... *A61F 2/2445* (2013.01); *A61F 2/2454* (2013.01); *A61F 2/2463* (2013.01)

(58) Field of Classification Search
    CPC .... A61F 2/2427; A61F 2/2445; A61F 2/2454; A61F 2/246; A61F 2/2463
    See application file for complete search history.

(56) References Cited

U.S. PATENT DOCUMENTS

| | | | |
|---|---|---|---|
| 6,749,630 B2* | 6/2004 | McCarthy | A61F 2/2448 623/2.37 |
| 2009/0198324 A1* | 8/2009 | Orlov | A61F 2/2445 623/2.37 |
| 2012/0136435 A1* | 5/2012 | Brunnett | A61F 2/2448 623/2.36 |
| 2016/0045312 A1* | 2/2016 | Braido | A61B 5/02028 623/2.37 |
| 2018/0325663 A1* | 11/2018 | Taylor | A61L 27/18 |
| 2020/0345495 A1* | 11/2020 | Gammie | A61F 2/2448 |

FOREIGN PATENT DOCUMENTS

WO    WO-2007040998 A1 *  4/2007  ........... A61F 2/2442

* cited by examiner

*Primary Examiner* — William H Matthews
(74) *Attorney, Agent, or Firm* — Riverside Law LLP

(57) ABSTRACT

The present invention provides devices for treating functional mitral regurgitation and methods of use thereof. The devices translocate a subject's mitral valve in an apical direction. The devices thereby treat mitral regurgitation while preserving a subject's original mitral valve and chordae tendinae.

20 Claims, 58 Drawing Sheets

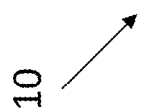

```
┌─────────────────────────┐     ┌─────────────────────────┐     ┌─────────────────────────┐
│ Separate one or more    │     │ Attach to the leaflet   │     │ Attach to the annulus   │
│ native leaflets from a  │     │ edge of the native      │     │ edge of the native      │
│ native annulus, the     │ ──▶ │ annulus an annulus end  │ ──▶ │ leaflet(s) a leaflet    │
│ separated native        │     │ of an annulus portion   │     │ end of a leaflet        │
│ leaflet(s) having an    │     │ of a ring-shaped body,  │     │ portion of the ring-    │
│ annulus edge at which   │     │ the annulus end having  │     │ shaped body, the        │
│ the native leaflet(s)   │     │ a perimeter             │     │ leaflet portion being   │
│ were joined to the      │     │                         │     │ axially spaced from     │
│ native annulus and the  │     │         14              │     │ the annulus portion,    │
│ native annulus having   │     │                         │     │ the leaflet end having  │
│ a leaflet edge at which │     │                         │     │ a perimeter equal to    │
│ the annulus was joined  │     │                         │     │ or larger than the      │
│ to the leaflet edge of  │     │                         │     │ perimeter of the        │
│ the native leaflet(s)   │     │                         │     │ annulus end             │
│                         │     │                         │     │                         │
│         12              │     │                         │     │         16              │
└─────────────────────────┘     └─────────────────────────┘     └─────────────────────────┘
```

FIG. 5A

FIG. 6A
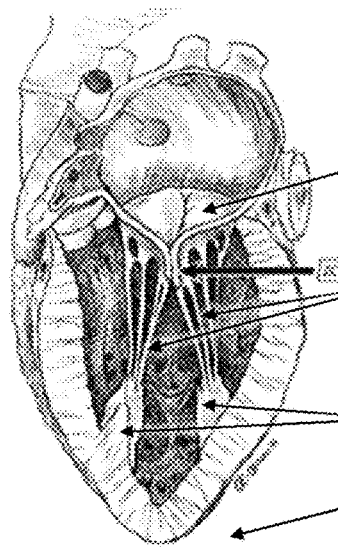
FIG. 6B
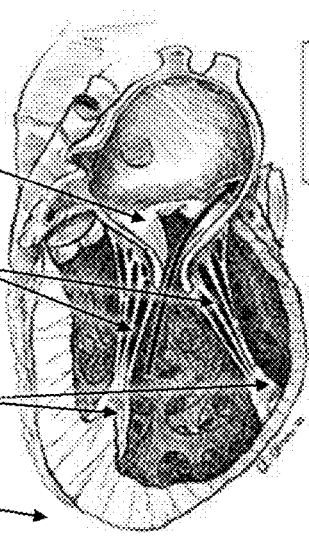
FIG. 6C
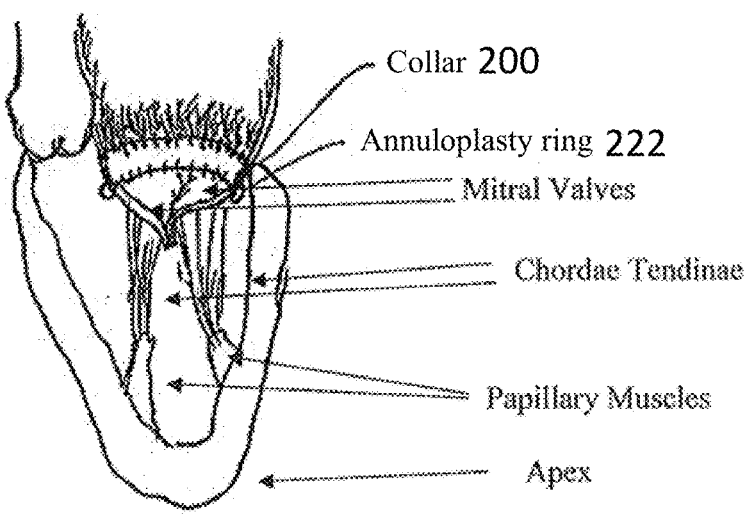
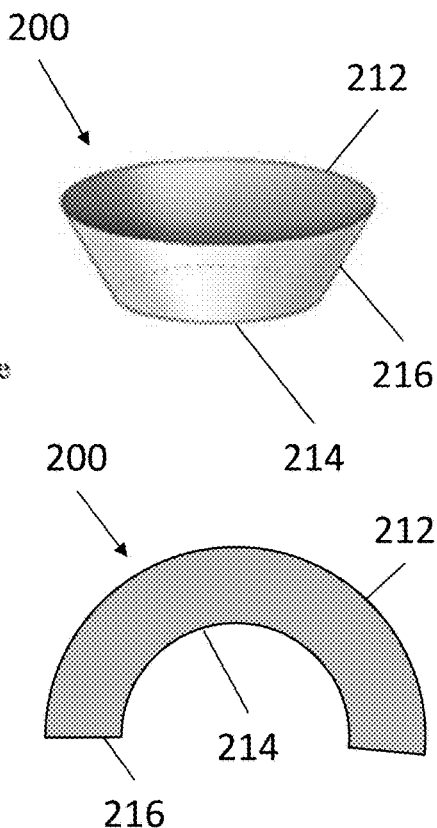

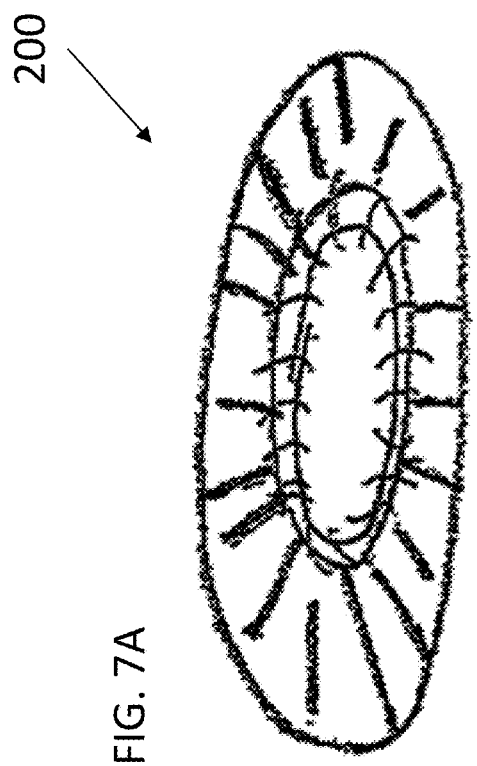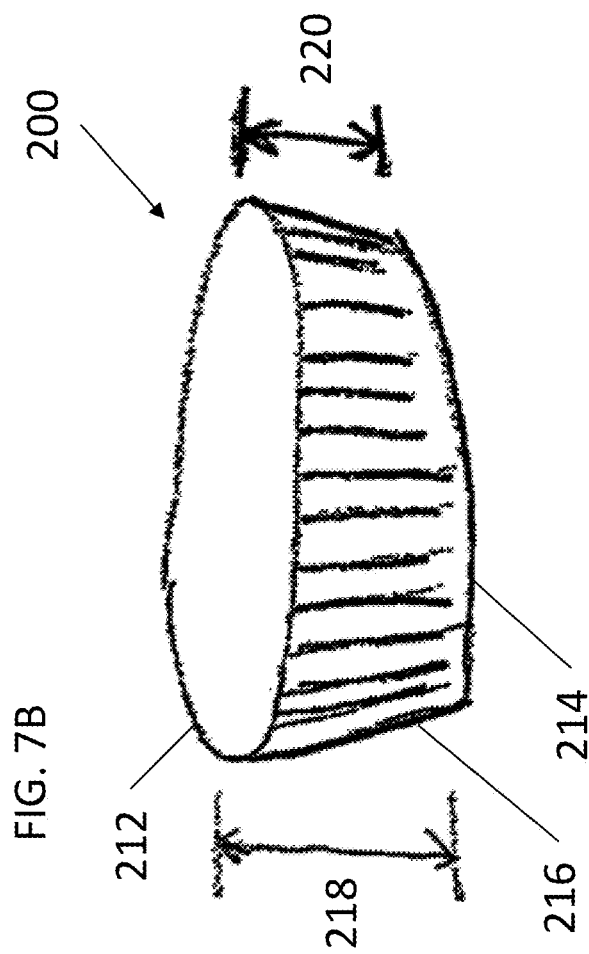
FIG. 7A
FIG. 7B

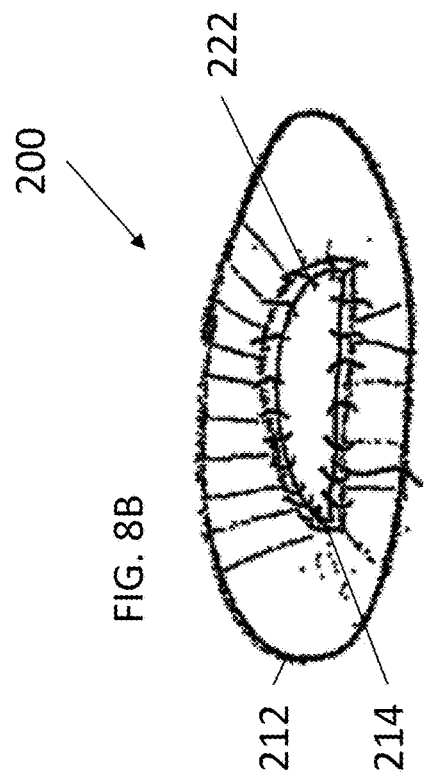
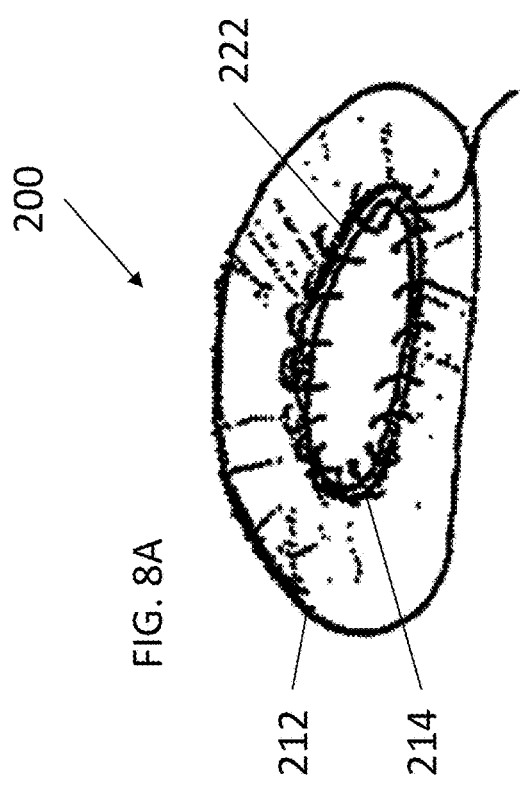
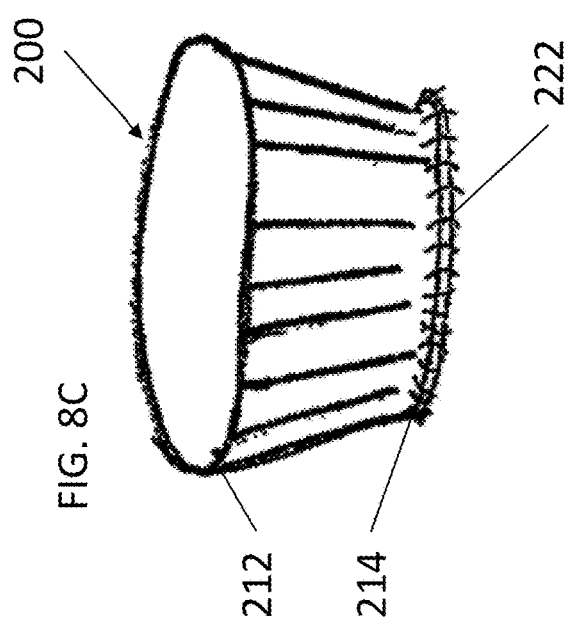

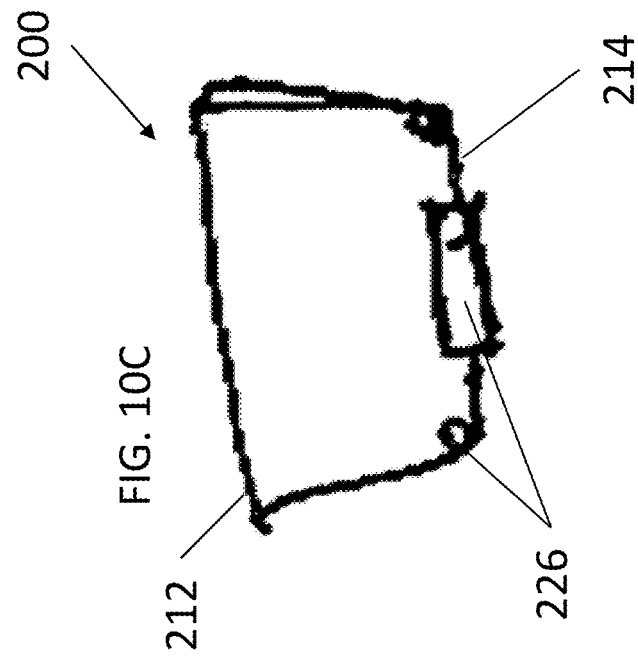
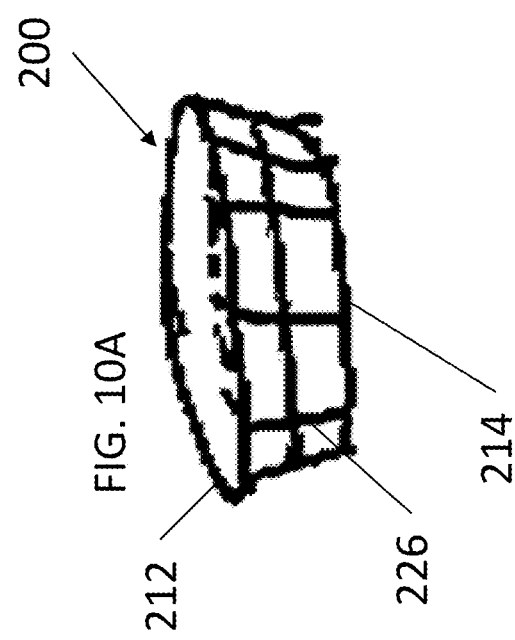
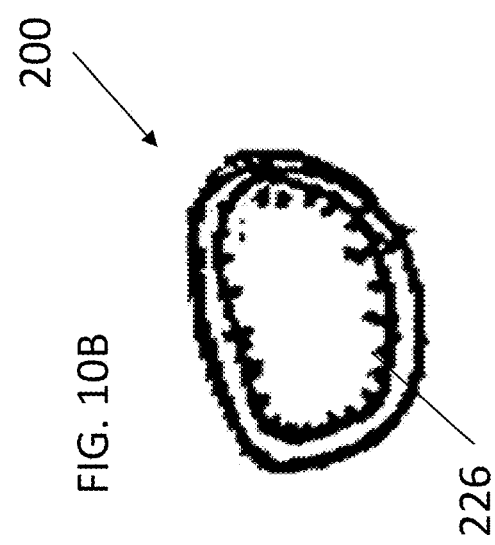

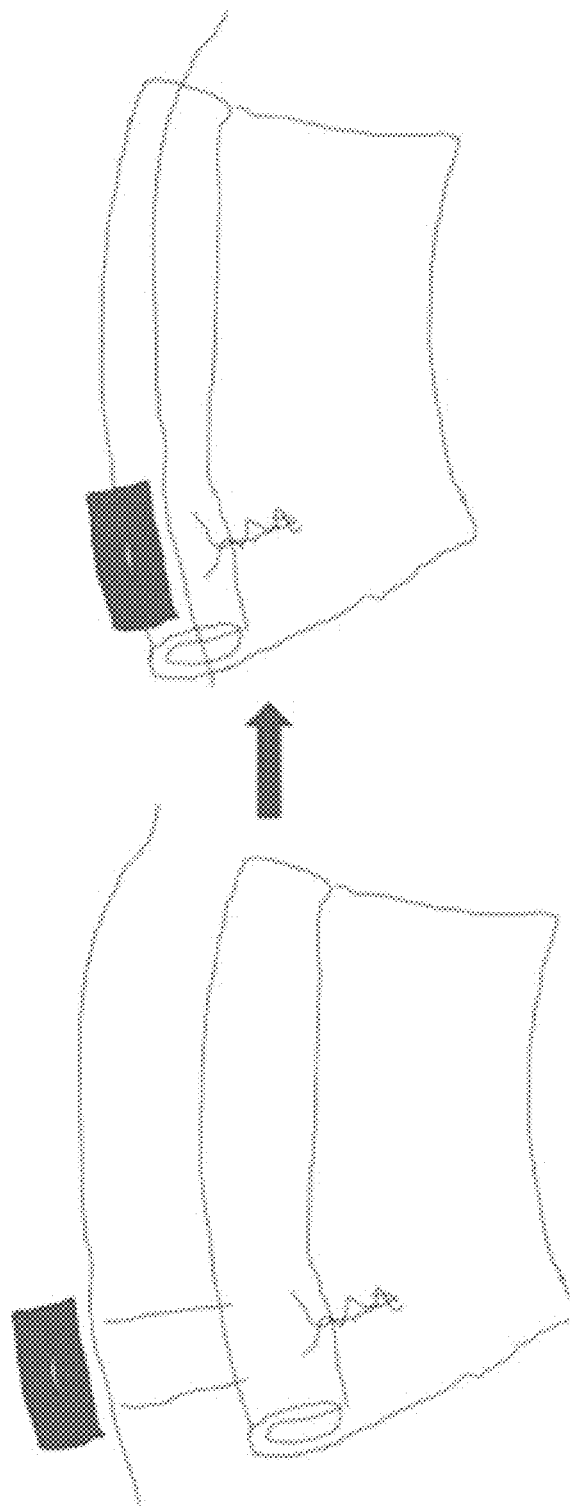
FIG. 13

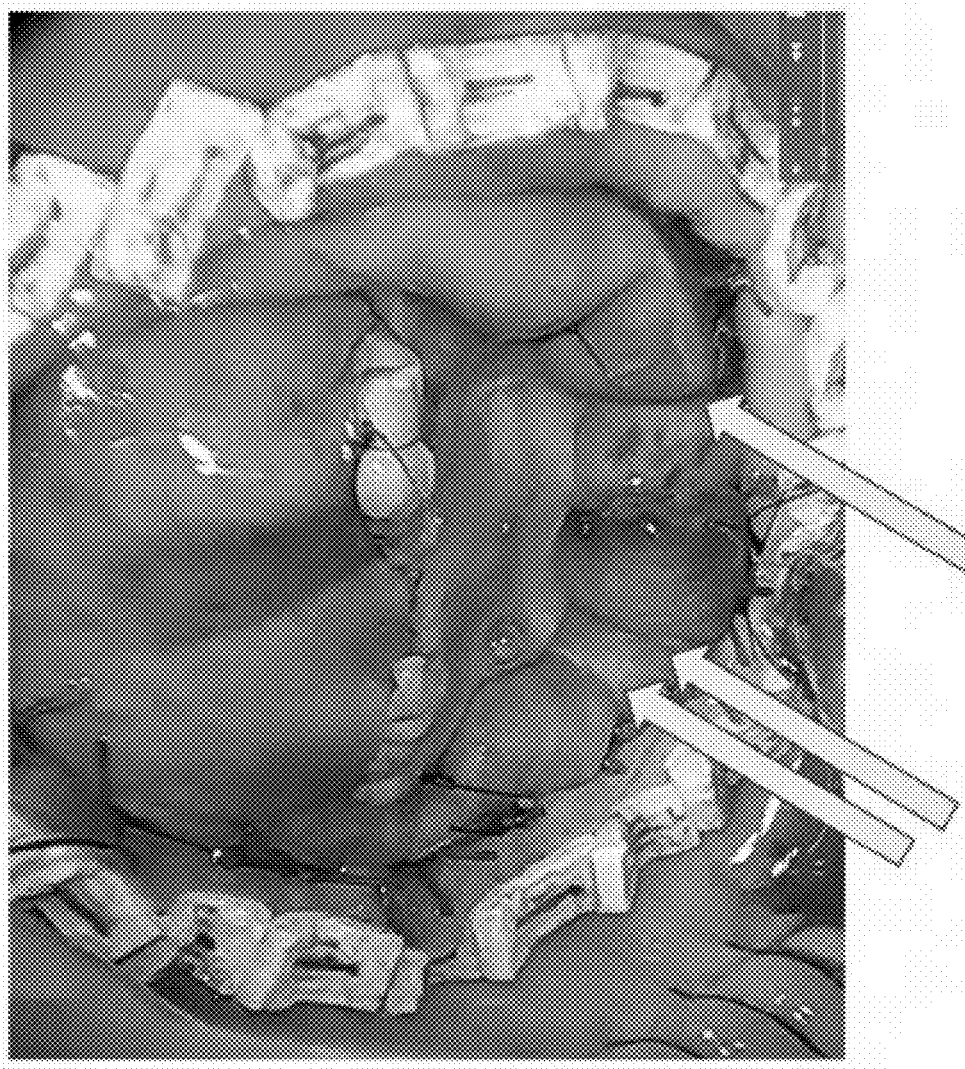
FIG. 19 Pleats/folds in patch in clinical case

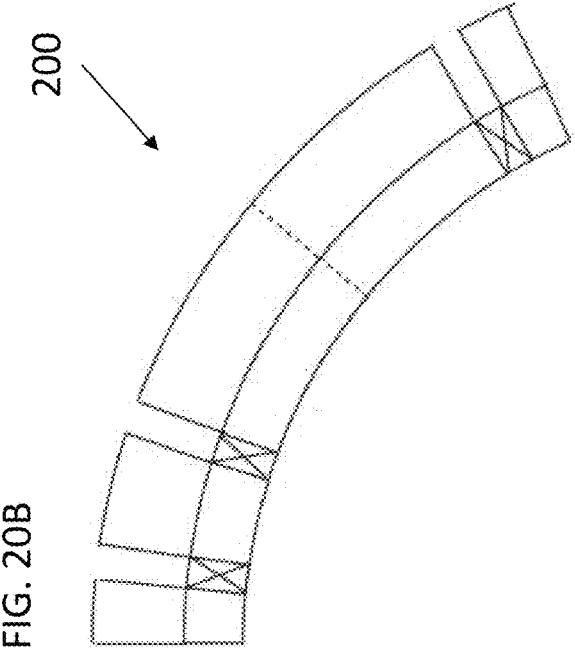
FIG. 20A
FIG. 20B
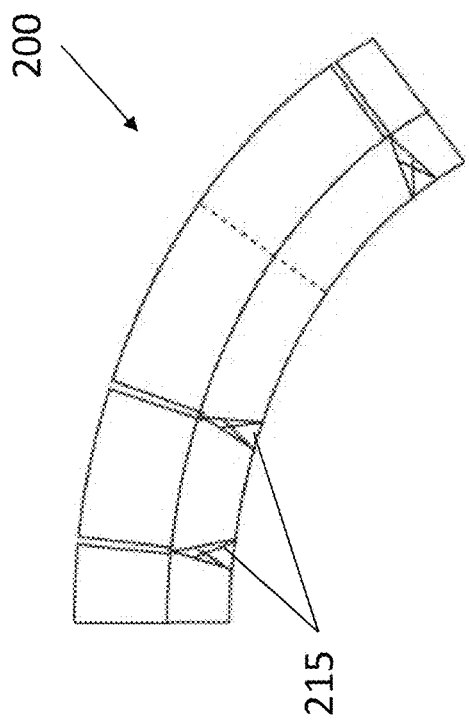
FIG. 20C
FIG. 20D
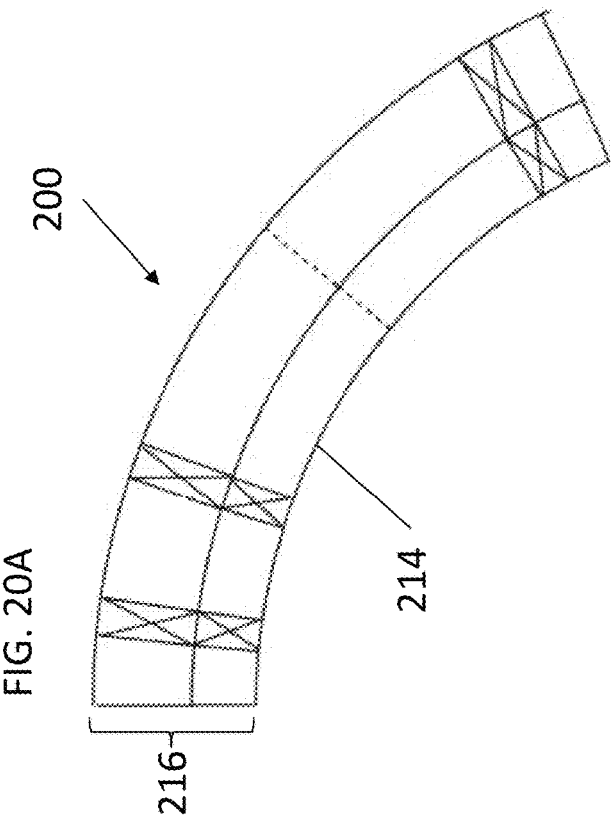
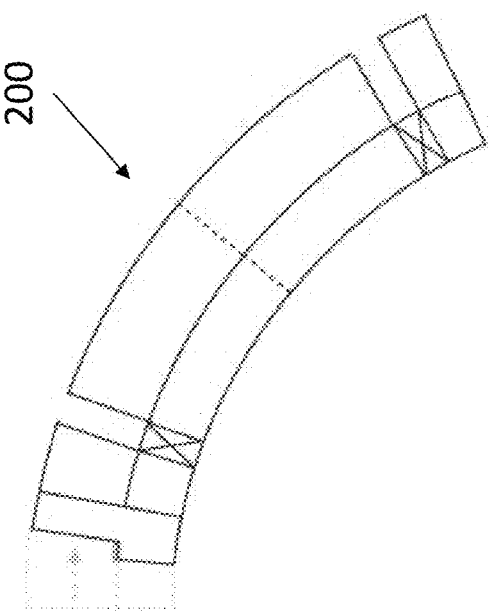

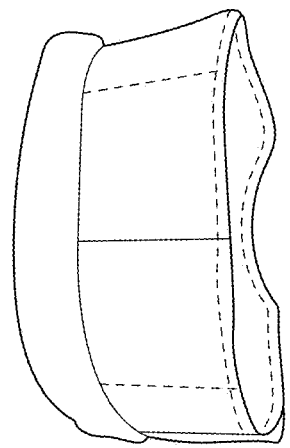
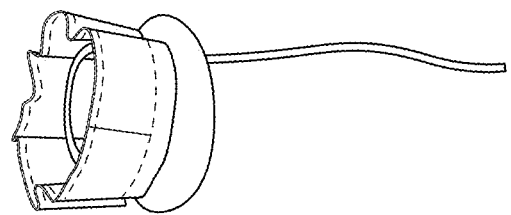
FIG. 22A

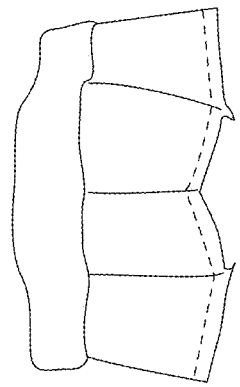
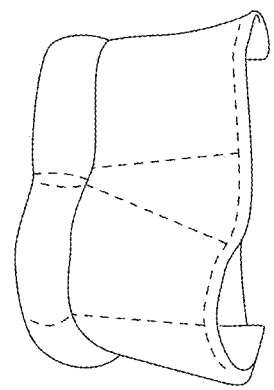
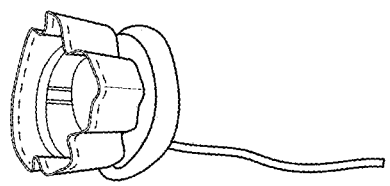
FIG. 22B

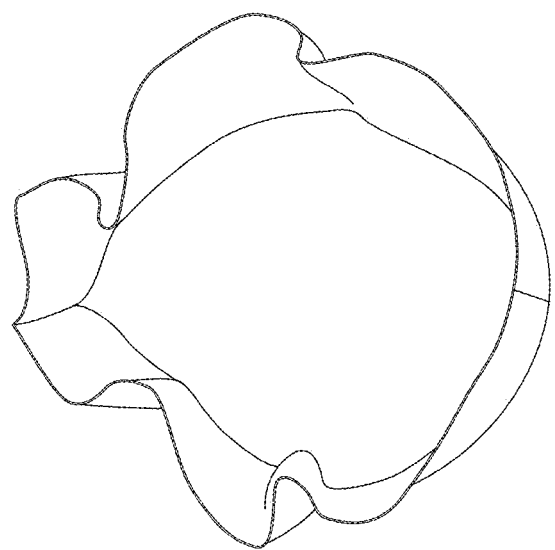
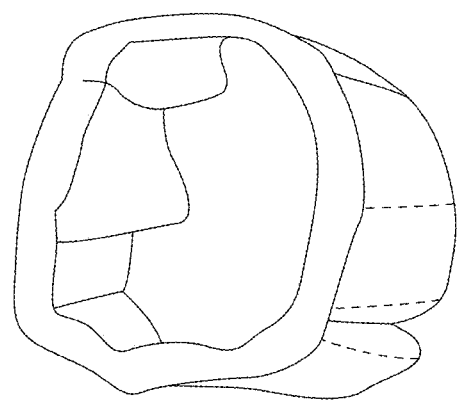
FIG. 22C

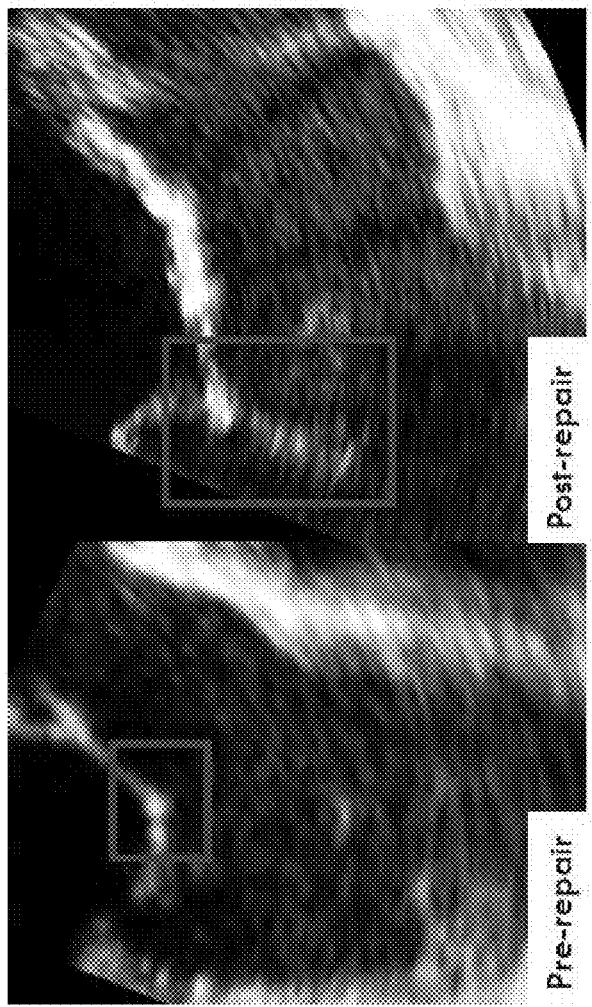
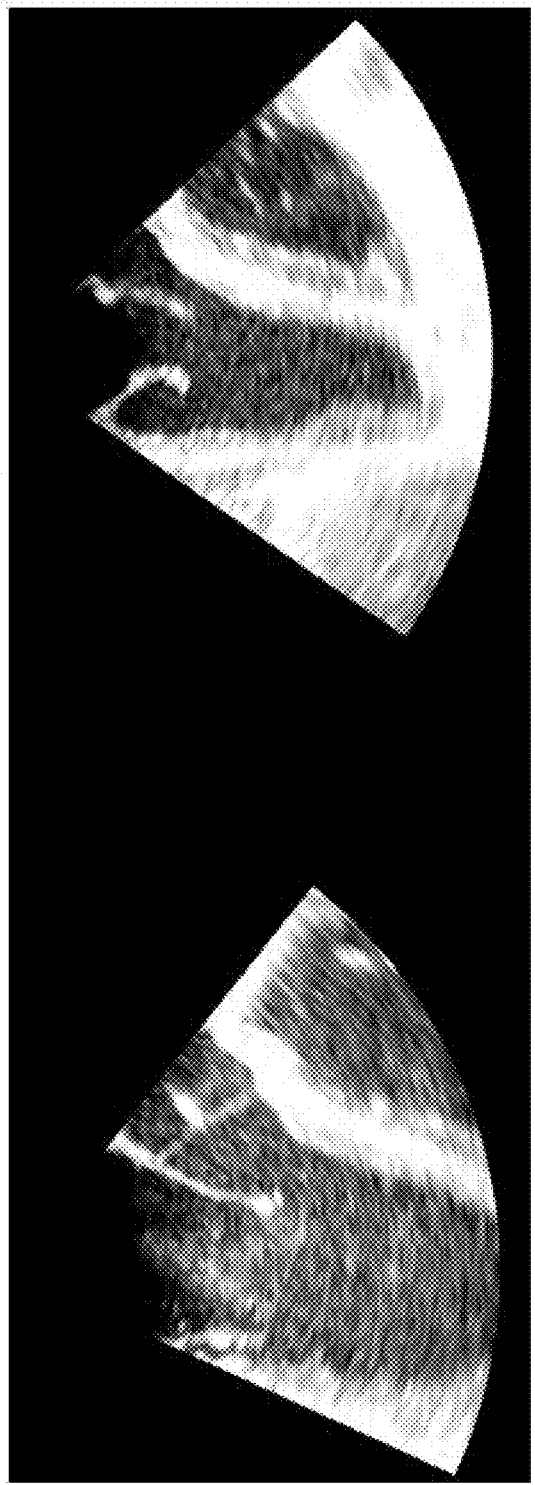
FIG. 42A

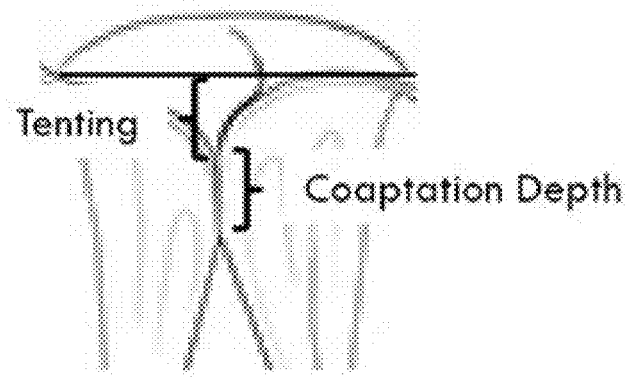
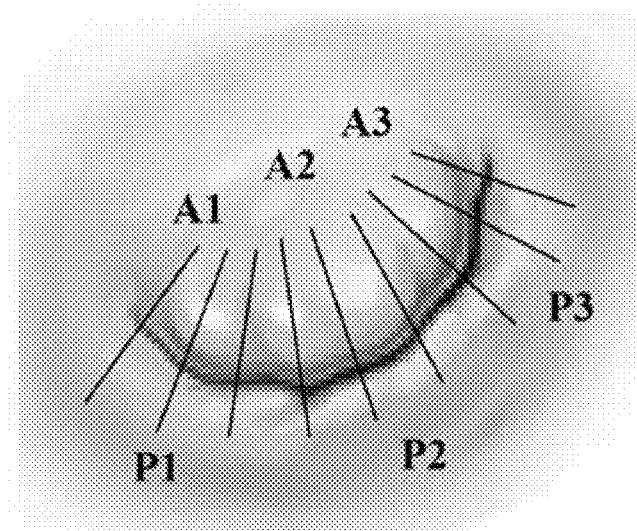
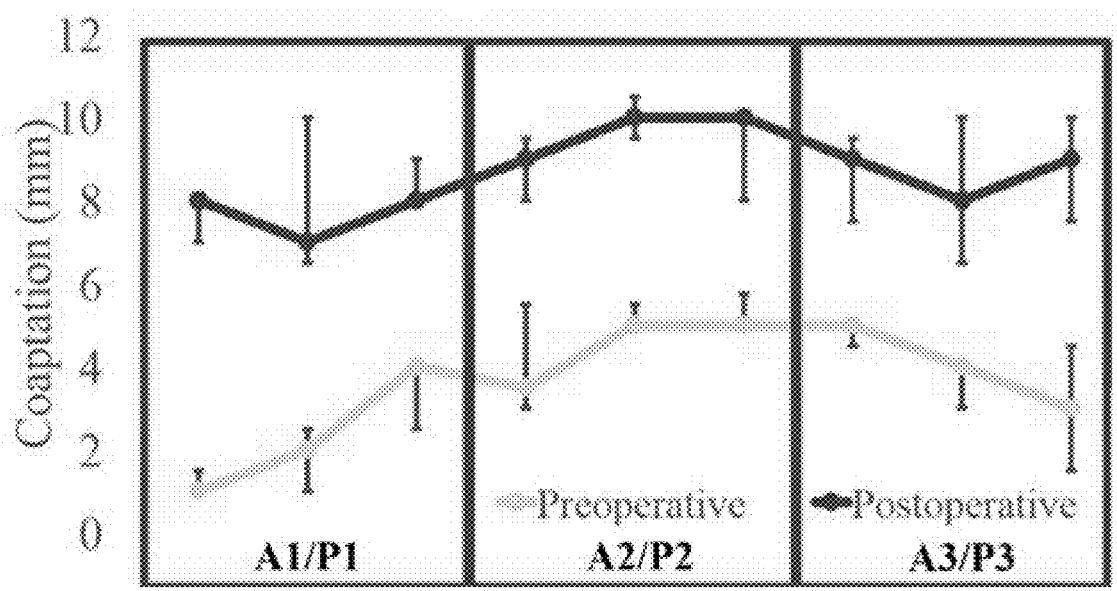
FIG. 42B

VALVE TRANSLOCATION DEVICE AND METHOD FOR THE TREATMENT OF FUNCTIONAL VALVE

CROSS-REFERENCE TO RELATED APPLICATIONS

This application is a continuation of U.S. patent application Ser. No. 17/584,157, filed on Jan. 25, 2022, which is a continuation of U.S. patent application Ser. No. 16/888,322 filed on May 29, 2020, which issued as U.S. Pat. No. 11,259,925 on Mar. 1, 2022, which is a continuation of International Application No. PCT/US20/31110, filed May 1, 2020, which claims priority to U.S. Provisional Application No. 62/842,085, filed May 2, 2019, the disclosures of each of which are hereby incorporated by reference herein in their entirety. Further, U.S. patent application Ser. No. 17/584,157 is a continuation-in-part of U.S. patent application Ser. No. 16/761,181 filed on May 1, 2020, which is a US national entry of International Application No. PCT/US18/59253, filed Nov. 5, 2018, which claims priority to U.S. Provisional Patent Application No. 62/581,085, filed Nov. 3, 2017, the disclosures of which are each hereby incorporated by reference herein in their entirety

BACKGROUND OF THE INVENTION

There is presently no reliable, durable mitral valve repair option for patients with functional mitral regurgitation (FMR). In patients with FMR, the mitral valve is usually normal, but left ventricular dysfunction (due to coronary artery disease, idiopathic myocardial disease, or nonischemic cardiomyopathy) is present. The abnormal and dilated left ventricle causes papillary muscle displacement, which results in leaflet tethering with associated annular dilation that prevents coaptation (generally defined as abutment of the edges of the two mitral valve leaflets). Thus, fundamental geometric issues of FMR include annular dilation, annular flattening, leaflet tethering, and increased interpapillary distances.

Although restrictive mitral annuloplasty (RMA) is usually initially effective in abrogating mitral regurgitation, there is clear data that these repairs are not as durable as replacing the mitral valve with a prosthetic (tissue or mechanical) valve. RMA involves suturing a semi-rigid ring around the perimeter of the mitral valve (the annulus) to decrease the area of the mitral orifice and increase the amount of coaptation of the two leaflets. The frequent progressive ineffectiveness of RMA is generally due to continued adverse remodeling and enlargement of the left ventricle, with continued geometric distortion—including continued restriction of the leaflets into the ventricular cavity with resulting failure of coaptation.

For example, in the ACORN trial (see J Thorac Cardiovasc Surg. 2011 September; 142(3):569-74) that included mostly patients with idiopathic FMR, the recurrence rate of severe mitral regurgitation (MR) was 19 percent at 5 years. Recent data from a randomized trial that compared repair and replacement of the mitral valve for severe FMR demonstrated that nearly 60 percent of patients with mitral valve repairs or replacements suffered recurrence of moderate or greater MR at 2 years. Importantly, the group of patients with recurrence also showed less favorable ventricular reverse remodeling (i.e. they had bigger ventricles) compared to a repair group that had durable treatment of MR. Fundamentally, a restrictive mitral annuloplasty does not leave an adequate surface area for coaptation. A variety of techniques have been tried to repair FMR in a more durable fashion than current techniques, but none have had widespread adoption or success.

While replacing the mitral valve with a prosthetic valve is the most durable current technique, prosthetic valves have significant downsides, including risks of thromboembolism, prosthetic valve infection, degeneration of bioprostheses, mandatory anticoagulation of mechanical valves, and a higher perioperative mortality risk. While there are clear benefits to mitral valve repair compared to replacement for patients with degenerative mitral valve disease, annuloplasty insertion for treating FMR is associated with a very high rate of early recurrence of mitral regurgitation (e.g., 58% at two years in a randomized CTSN trial, NEJM 2016).

Common techniques often use a MitraClip®, and are based on a surgical approach (the "Alfieri" stitch) that is known to be only variably effective. The MitraClip® procedure involves placing a Dacron®-covered titanium clip such that the middle portion of the anterior and posterior leaflets are joined, which forms the mitral valve into a "double orifice" valve. Results from treatment of FMR with the MitraClip® have been suboptimal and a substantial number of patients have either residual or recurrent mitral regurgitation.

Therefore, there is a need in the art for improved devices and methods for treating functional mitral regurgitation. The present invention addresses this need.

SUMMARY OF THE INVENTION

In some embodiments, an apparatus comprises a ring-shaped body having an annulus portion and a leaflet portion axially spaced from the annulus portion, the annulus portion having an annulus end having a perimeter and being configured to be attached to an annulus of a native heart valve from which a leaflet of the native heart valve has been separated, the leaflet portion having a leaflet end having a perimeter equal to or larger than the annulus portion perimeter and being configured to be attached to the native heart valve leaflet and thereby to connect the native heart valve leaflet to the native heart valve annulus.

In some embodiments, the leaflet portion of the ring-shaped body includes a pleat having an expandable portion extending to the leaflet end of the ring-shaped body to define in part the perimeter of the leaflet end and a fixed portion spaced from the leaflet end, the expandable portion of the pleat being configured to be attached to the native heart valve leaflet.

In some embodiments, the pleat is a first pleat, the expandable portion of the first pleat is configured to be attached to the leaflet, the leaflet portion of the ring-shaped body includes a second pleat having an expandable portion extending to the leaflet end of the ring-shaped body further to define in part the perimeter of the leaflet end and a fixed portion spaced from the leaflet end, the expandable portion of the second pleat being configured to be attached to the leaflet.

In some embodiments, the leaflet end of the ring-shaped body has a first circumferential portion having a thickness and a second circumferential portion have a thickness different from the thickness of the first circumferential portion.

In some embodiments, the native heart valve leaflet is a first leaflet from a plurality of native heart valve leaflets that have been separated from the native heart valve, the first leaflet having a first thickness and a second leaflet from the plurality of native heart valve leaflets having a second thickness, the first thickness being greater than the second thickness, and the thickness of the first circumferential portion being approximately equal to the first thickness and the thickness of the second circumferential portion being approximately equal to the second thickness.

In some embodiments, the native heart valve is a mitral valve, the first leaflet is an anterior leaflet and the second leaflet is a posterior leaflet.

In some embodiments, the annulus end has a thickness greater than a thickness of the remainder of the annulus portion.

In some embodiments, the annulus portion is formed of a sheet of material, the annulus end is integrally formed with the remainder of the annulus portion with multiple layers of the sheet of material.

In some embodiments, the annulus end is formed by rolling the sheet of material.

In some embodiments, the annulus end is formed separately from, and coupled to, the annulus portion.

In some embodiments, the ring-shaped body is formed of biological tissue.

In some embodiments, the biological tissue is human or bovine pericardial tissue.

In some embodiments, the ring-shaped body is formed of at least one of decellularized tissue, polymer, or artificial fabric.

In some embodiments, the annulus portion has a thickness different from the leaflet portion.

In some embodiments, a method of repairing a native heart valve having a native annulus and native leaflets extending from the native annulus, comprises separating a native leaflet from the native annulus, the separated native leaflet having an annulus edge at which the native leaflet was joined to the annulus and the native annulus having a leaflet edge at which the annulus was joined to the leaflet edge of the native leaflet; attaching to the leaflet edge of the native annulus an annulus end of an annulus portion of a ring-shaped body, the annulus end having a perimeter; and attaching to the annulus edge of the native leaflet a leaflet end of a leaflet portion of the ring-shaped body, the leaflet portion being axially spaced from the annulus portion, the leaflet end having a perimeter equal to or larger than the perimeter of the annulus end.

In some embodiments, the native leaflet is circumferentially redundant in configuration, the leaflet portion of the ring-shaped body includes a pleat having an expandable portion extending to the leaflet end of the ring-shaped body and a fixed portion spaced from the leaflet end, and the attaching to the annulus edge of the native leaflet includes circumferentially expanding the native leaflet and attaching the expandable portion of the pleat to the native leaflet.

In some embodiments, the native leaflet is a first native leaflet and the separating includes separating a second native leaflet from the native annulus, the separated second native leaflet having an annulus edge at which the second native leaflet was joined to the annulus, the second native leaflet being segmented, the pleat is a first pleat, and the leaflet portion of the ring-shaped body includes a second pleat having an expandable portion extending to the leaflet end of the ring-shaped body and a fixed portion spaced from the leaflet end, and the attaching to the annulus edge including attaching the expandable portion of the second pleat to the second native leaflet.

In some embodiments, the native leaflet is a first native leaflet and the separating includes separating a second native leaflet from the native annulus, the first native leaflet having a first thickness and the second native leaflet having a second thickness, the first thickness being greater than the second thickness, the leaflet end of the ring-shaped body has a first circumferential portion having a thickness approximately equal to the first thickness and a second circumferential portion having a thickness less than the thickness of the first circumferential thickness and approximately equal to the second thickness, and the attaching to the annulus edge including attaching the first circumferential portion to the first native leaflet and attaching the second circumferential portion to the second native leaflet.

In some embodiments, the native heart valve is a mitral valve, the first native leaflet is an anterior leaflet, and the second native leaflet is a posterior leaflet.

In some embodiments, the attaching to the leaflet edge of the native annulus and the attaching to the annulus edge of the native leaflet includes suturing.

In some embodiments, the attaching to the leaflet edge of the native annulus includes passing sutures through the annulus end of the ring-shaped body, through the native annulus, and through a plurality of pledgets distributed circumferentially around the native annulus.

In some embodiments, a method of repairing a native heart valve having a native annulus and native leaflets extending from the native annulus, comprising separating a native leaflet from the native annulus, the separated native leaflet having an annulus edge at which the native leaflet was joined to the annulus and the native annulus having a leaflet edge at which the annulus was joined to the leaflet edge of the native leaflet; attaching to the leaflet edge of the native annulus an annulus end of an annulus portion of a semi-annular body; and attaching to the annulus edge of the native leaflet a leaflet end of a leaflet portion of the semi-annular body, the leaflet portion being axially spaced from the annulus portion.

In some embodiments, the native leaflet is a first native leaflet from a plurality of native leaflets extending from the native annulus, the attaching to the leaflet edge the annulus end of the annulus portion of the semi-annular body occurring with a second native leaflet extending from the native annulus.

In some embodiments, the method further comprises: separating from the native annulus a third native leaflet from the plurality of native leaflets, the third separated native leaflet having an annulus edge at which the native leaflet was jointed to the annulus; and attaching to the annulus edge of the third native leaflet the leaflet end of the leaflet portion of the semi-annular body.

In some embodiments, the separating the native leaflet from the native annulus includes separating less than an entirety of the native leaflet from the native annulus, thereby leaving a portion of the native leaflet attached to and extending from the native annulus.

In some embodiments, the portion of the native leaflet attached to and extending from the native annulus is between about 2 mm and about 4 mm in length.

In some embodiments, the native heart valve is a tricuspid valve.

In some embodiments, an apparatus comprises a ring-shaped body having an annulus portion and a leaflet portion axially spaced from the annulus portion, the annulus portion having an annulus end and being configured to be attached to an annulus of a native heart valve from which a leaflet of the native heart valve has been separated, the leaflet portion having a leaflet end including a pleat having an expandable portion extending to the leaflet end and a fixed portion spaced from the leaflet end, the expandable portion of the pleat being configured to be attached to the native heart valve leaflet and thereby to connect the native heart valve leaflet to the native heart valve annulus.

In some embodiments, the expandable portion of the pleat has a first configuration in which the leaflet end has a first perimeter and a second, expanded configuration, in which the leaflet end has a second perimeter greater than the first perimeter.

In some embodiments, the annulus end has a perimeter, and the leaflet end has a perimeter equal to or greater than the annulus end perimeter when the expandable portion of the pleat is in its second, expanded configuration.

In some embodiments, the annulus end has a perimeter, and the leaflet end has a perimeter less than the annulus end perimeter when the expandable portion of the pleat is in its second, expanded configuration.

In some embodiments, a translocation collar device comprises a substantially ring-shaped band of material having a first edge, a second edge opposite from the first edge, and a width in between; wherein the collar device is attachable to a circumferentially separated valve such that the first edge is attached to a valve annulus and the second edge is attached to a valve perimeter to translocate the valve in an apical direction.

In some embodiments, the first edge or the second edge has a diameter between about 20 mm and 60 mm.

In some embodiments, the width is between about 5 mm and 15 mm.

In some embodiments, the width is biased such that the first edge and the second edge are separated by a variable distance.

In some embodiments, the device is constructed from a length of material having an arc shape, with a first end, a second end, an outer arc, and an inner arc, such that the first end and the second end are joinable together to form a substantially ring-shaped band.

In some embodiments, the device further comprises one or more concentric folds aligned in parallel with the first edge and the second edge, such that the width is variable.

In some embodiments, the width is fixable by applying one or more sutures or adhesives to the one or more concentric folds.

In some embodiments, the device further comprises one or more annuloplasty rings attached to the annular edge, the apical edge, or both.

In some embodiments, the device further comprises one or more cuffs attached to the first edge, the second edge, or a position in between.

In some embodiments, the material is selected from the group consisting of: polymer, fabrics, plastics, metals, autograft tissue, allograft tissue, xenograft tissue, and engineered tissue constructs.

In some embodiments, one of the first edge and the second edge is rolled to form a sewing cuff or collar.

In some embodiments, the ring-shaped band of material comprises one or more pleats extending from the first edge to the second edge.

In some embodiments, at least one flap of material extends from one of the first edge and the second edge to form at least one neo-leaflet.

In some embodiments, a plurality of artificial chords are looped along an outer edge of the at least one flap of material and the edge that the at least one flap of material extends from.

In some embodiments, a method of translocating a valve, the method comprises the steps of providing a translocation collar device having a ring-like shape with a first edge, a second edge, and a width in between; forming a circumferential incision around a perimeter of a valve to separate a valve annulus from a valve perimeter; circumferentially attaching the first edge of the collar device to the valve annulus; and circumferentially attaching the second edge of the collar device to the valve perimeter.

In some embodiments, the translocation collar device is sized to fit the valve annulus and valve perimeter by measuring the dimensions of the valve annulus and valve perimeter.

In some embodiments, the translocation collar device is sized to fit the valve annulus and valve perimeter by performing and measuring the dimensions of a 3D echocardiogram of a heart containing the valve.

In some embodiments, the circumferential incision is formed while keeping the valve and associated structures intact, the associated structures including leaflets, commissures, chordae tendinae, and papillary muscles.

In some embodiments, the first edge and the second edge of the collar device are attached after the circumferential incision is fully formed and the valve annulus is completely separated from the valve perimeter.

In some embodiments, the first edge and the second edge of the collar device are attached as the circumferential incision is being formed and the valve annulus is partially separated from the valve perimeter.

In some embodiments, a valve translocation kit, comprises at least one translocation collar device having a ring-like shape with a first edge, a second edge, and a width in between; and one or more suture threads, suture pledgets, forceps, scissors, scalpels, translocation collar device holders, and combinations thereof.

In some embodiments, the kit further comprises one or more circumferential bands, each circumferential band configured to wrap around papillary muscles connected to a valve.

In some embodiments, the kit further comprises one or more tethers or artificial chords.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

FIG. 5A is a flowchart illustrating a method of deploying a valve translocation device to a desired location in a body, according to an embodiment.

FIG. 6A and FIG. 6B depict in front cross-sectional view the anatomy of a left atrium, left ventricle, and mitral valve, in an open and closed configuration, respectively. FIG. 6C depicts an exemplary translocation collar device and the implantation of the translocation collar device around the mitral valve to displace it towards the apex of the heart, according to an embodiment.

FIG. 7A and FIG. 7B depict exemplary translocation collar devices having biased heights.

FIG. 8A through FIG. 8C depict exemplary translocation collar devices having annuloplasty rings.

FIG. 10A through FIG. 10C depict exemplary translocation collar devices having sewing cuffs.

FIG. 11A shows a full template. FIG. 11B shows the top portion of the template rolled over twice to form the sewing cuff or collar. Markings on the template and patch show quadrants (unbroken lines) and eighth marks (dashed lines), which are transcribed onto the template. FIG. 11C shows the completed sewing cuff or collar on template; red indicates running suture to secure the rolled edge to the body of the device. Dashed lines are original template outline.

FIG. 13 is a photograph (top) shows the rolled sewing cuff or collar of an exemplary translocation collar device ready for suturing and a schematic of the rolled sewing cuff or collar and a pledget supporting a suture (bottom).

FIG. 19 is a photograph showing that the native mitral valve is characterized by "clefts" between portions of the posterior leaflet.

FIG. 20A through FIG. 20I depict the progression of the formation of an exemplary translocation collar device. FIG. 20A shows the full template; the device is drawn on to a pericardium, transferring all marks from the template to the pericardium. The 'X' and 'x' notations indicate the locations of the three pleats. The upper 'X' is located in the area that will be rolled/cuffed, and the lower 'x' is in the patch proper that will be pleated. FIG. 20B shows the creation of a pleat, where the areas 'X' are cut out of the pericardium, leaving the areas 'x' intact. FIG. 20C shows the 'x' portions are folded over such that the cut edges (where the 'X' portions were removed) line up (at the halfway point of the 'x' portion on the patch). The pleat is sewn in place using running prolene suture (red hash marks). This is done for all pleats in the device. FIG. 20D shows three pleats have been created. The 'x' portions are 'hidden' inside the pleat, shown as triangles in the body of the patch, secured by the stitches at the level of the collar (red hash marks). FIG. 20E shows the sewing collar portion of the device is then rolled over twice. It can be held in position using clamps while it is sewn into place with running prolene suture. FIG. 20F shows the completed patch, showing the rolled edge of the sewing collar has been stitched down (red hash marks). Figure-of-eight stitches are placed at the juncture between pleats where the 'X' portions were removed, so as to prevent leaks. Grey dashed lines show the original template shape. FIG. 20G shows the completed pleated device. FIG. 20H shows the completed frustrum-shaped device in 3D. FIG. 20I shows a ruffled device in 3D.

FIG. 22A through FIG. 22C depict an exemplary translocation collar device with pleats prototyped using surgical drape material. FIG. 22A depicts a completed pleated device (having 4 pleats) mounted to a mitral valve replacement sizer (left) and unmounted (right) showing the 'anterior leaflet' portion. FIG. 22B depicts the device mounted to a mitral valve sizer (left) and unmounted (middle, right) showing 'posterior leaflet' portion with pleats. FIG. 22C depicts additional views of the unmounted device from the atrial/annular side (left) and the ventricular/leaflet side (right).

FIG. 42A and FIG. 42B depict the results of an in vivo swine analysis comparing the effects of implanting a prototype translocation collar device on mitral valve coaptation.

DETAILED DESCRIPTION

Figure 1:
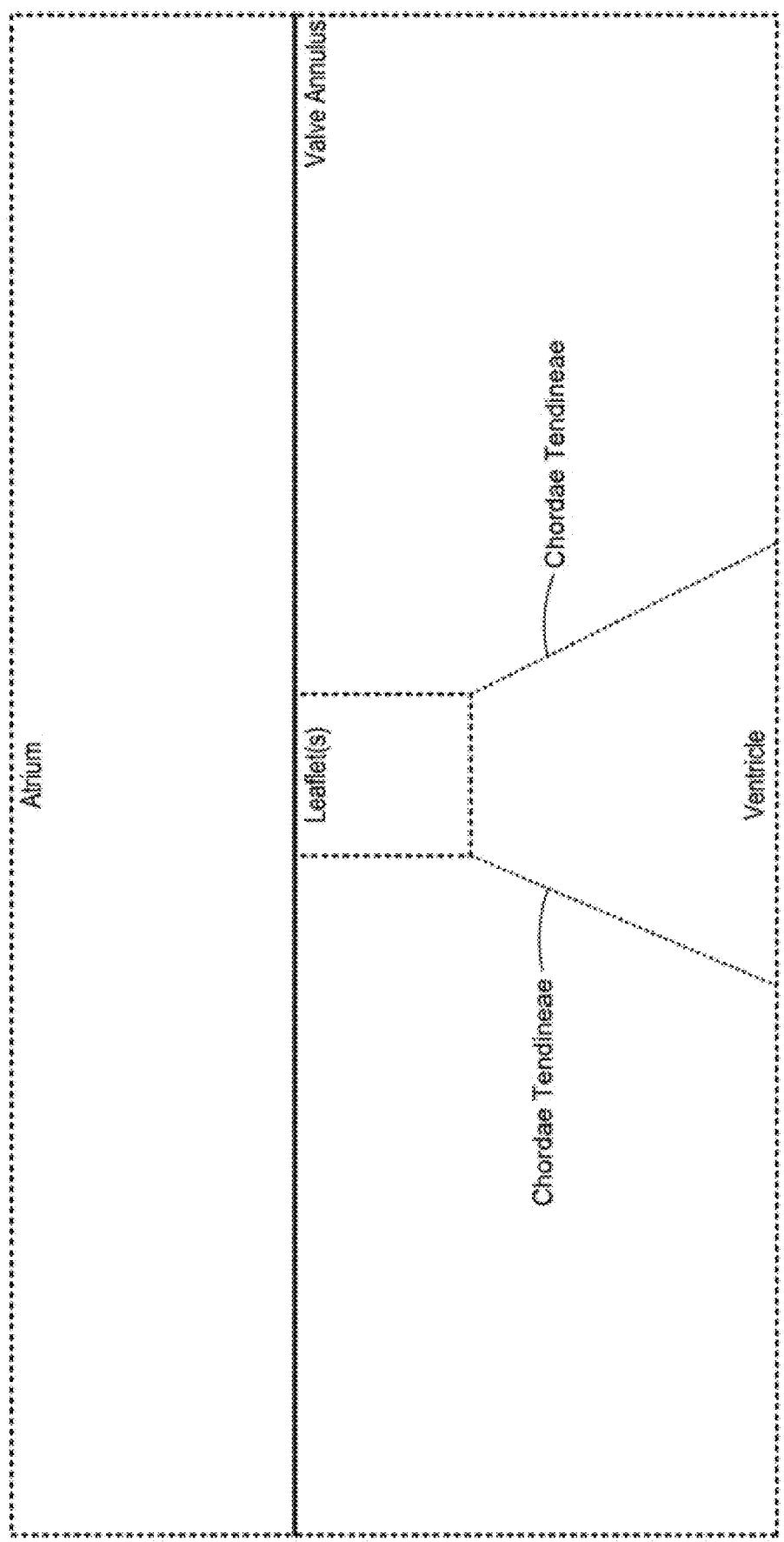
FIG. 1 is a front view schematic illustration of a native heart valve.

The present invention provides devices and techniques for durable and reasonably adaptable valve translocation to repair and treat regurgitation. The device translocates a subject's mitral valve (and/or other heart valve, such as a tricuspid valve) in the ventricle, positioning the mitral valve toward the apex of the subject's heart to compensate for the fundamental geometric issues of FMR, such as annular dilation, annular flattening, leaflet tethering, and increased interpapillary distances. The device is configured to decrease the amount of tethering of the patient's mitral valve leaflets to increase the coaptation surface area between the two mitral valve leaflets. The device preserves the original mitral valve and chordae tendinae in an intact manner. Therefore, the device increases the likelihood of a durable repair and an effective and lasting treatment of FMR. In addition, the device addresses flattening of the annulus and annular dilation.

Definitions

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein. Rather, these embodiments are provided so that this disclosure will be thorough and complete, and will fully convey the scope of the inventive concepts to those skilled in the art. Like numbers refer to like elements throughout.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

As used herein, the singular forms "a", "an" and "the" are intended to include the plural forms as well, unless the context clearly indicates otherwise. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," etc.). Similarly, the terms "comprises" and/or "comprising," when used in this specification, specify the presence of stated features, integers (or fractions thereof), steps, operations, elements, and/or components, but do not preclude the presence or addition of one or more other features, integers (or fractions thereof), steps, operations, elements, components, and/or groups thereof. As used in this document, the term "comprising" means "including, but not limited to."

As used herein the term "and/or" includes any and all combinations of one or more of the associated listed items. It should be understood that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All ranges disclosed herein also encompass any and all possible subranges and combinations of subranges thereof unless expressly stated otherwise. Any listed range should be recognized as sufficiently describing and enabling the same range being broken down into at least equal subparts unless expressly stated otherwise. As will be understood by one skilled in the art, a range includes each individual member. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments therebetween. This applies regardless of the breadth of the range.

Some biocompatible synthetic material(s) can include, for example, polyesters, polyurethanes, polytetrafluoroethylene (PTFE) (e.g., Teflon), and/or the like. Where a thin, durable synthetic material is contemplated, synthetic polymer materials such expanded PTFE or polyester may optionally be used. Other suitable materials may optionally include elastomers, thermoplastics, polyurethanes, thermoplastic polycarbonate urethane, polyether urethane, segmented polyether urethane, silicone polyether urethane, polyetheretherketone (PEEK), silicone-polycarbonate urethane, polypropylene, polyethylene, low-density polyethylene (LDPE), high-density polyethylene (HDPE), ultra-high density polyethylene (UHDPE), polyolefins, polyethylene-glycols, polyethersulphones, polysulphones, polyvinylpyrrolidones, polyvinylchlorides, other fluoropolymers, polyesters, polyethylene-terephthalate (PET) (e.g., Dacron), Poly-L-lactic acids (PLLA), polyglycolic acid (PGA), poly(D, L-lactide/glycolide) copolymer (PDLA), silicone polyesters, polyamides (Nylon), PTFE, elongated PTFE, expanded PTFE, siloxane polymers and/or oligomers, and/or polylactones, and block co-polymers using the same.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Valve Translocation Device

Figure 2:
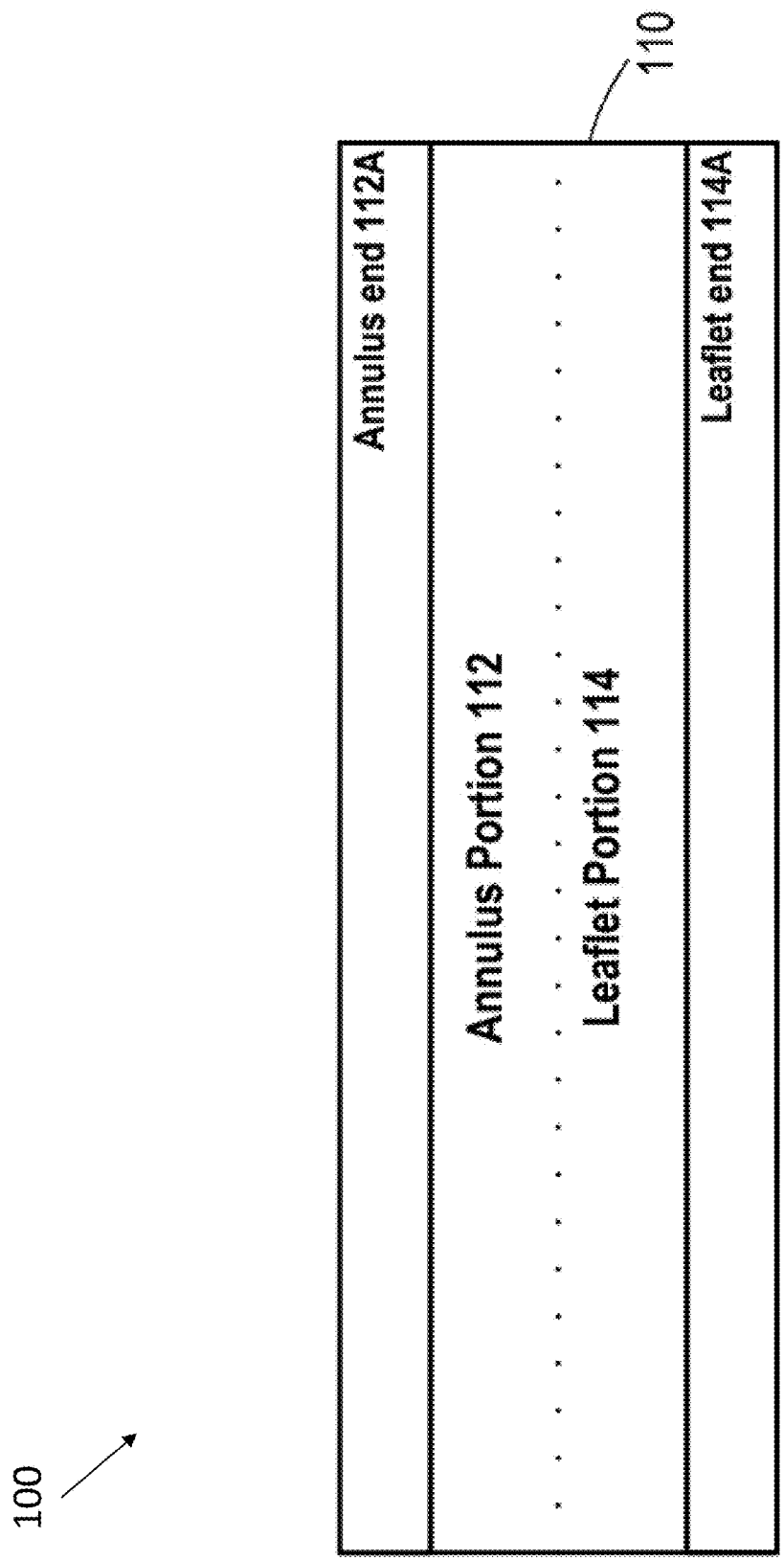
FIG. 2 is a front view schematic illustration of a valve translocation device, according to an embodiment.
Figure 3:
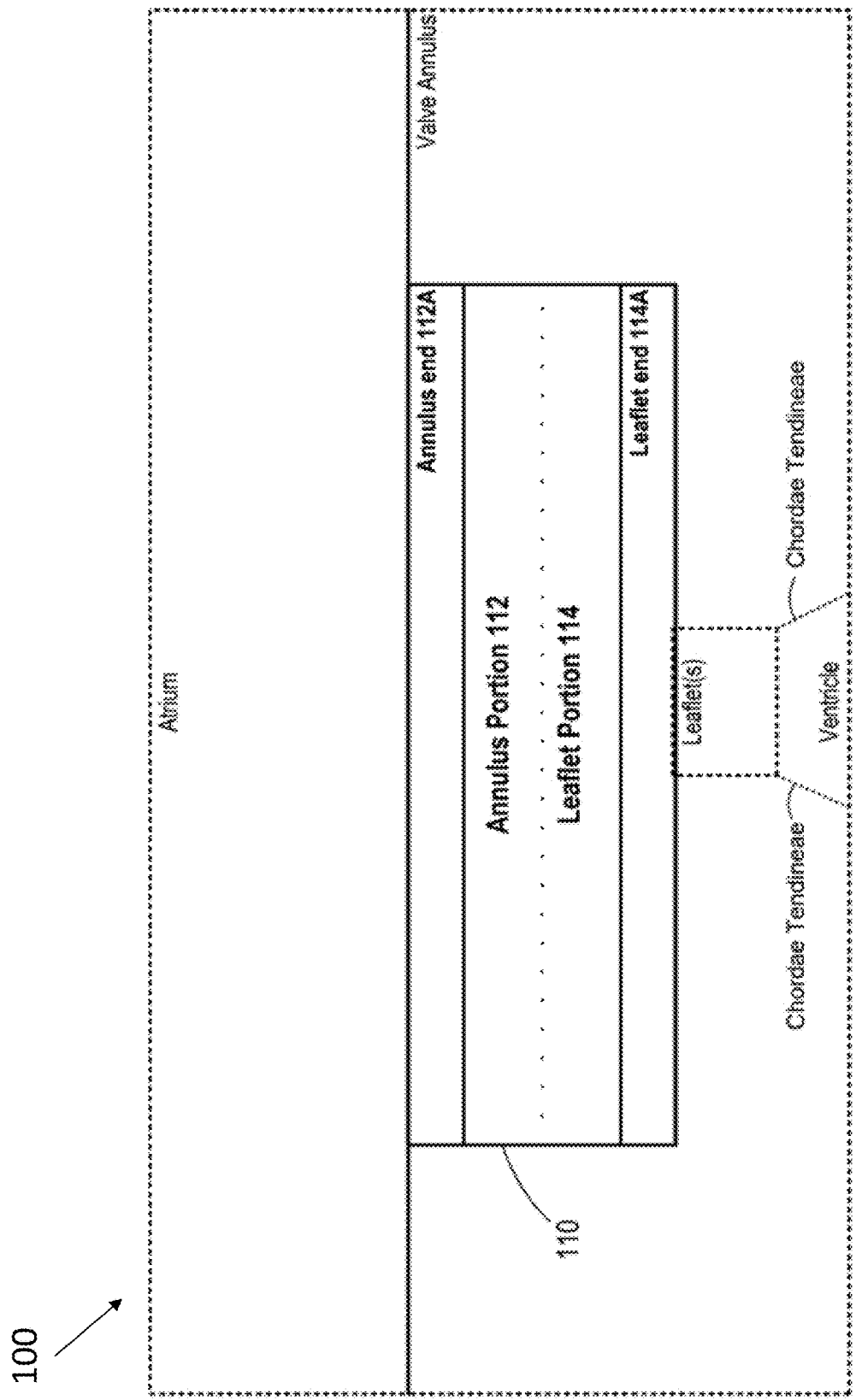
FIG. 3 is a front view schematic illustration of the valve translocation device of FIG. 2 deployed within the native heart valve of FIG. 1.
Figure 4:
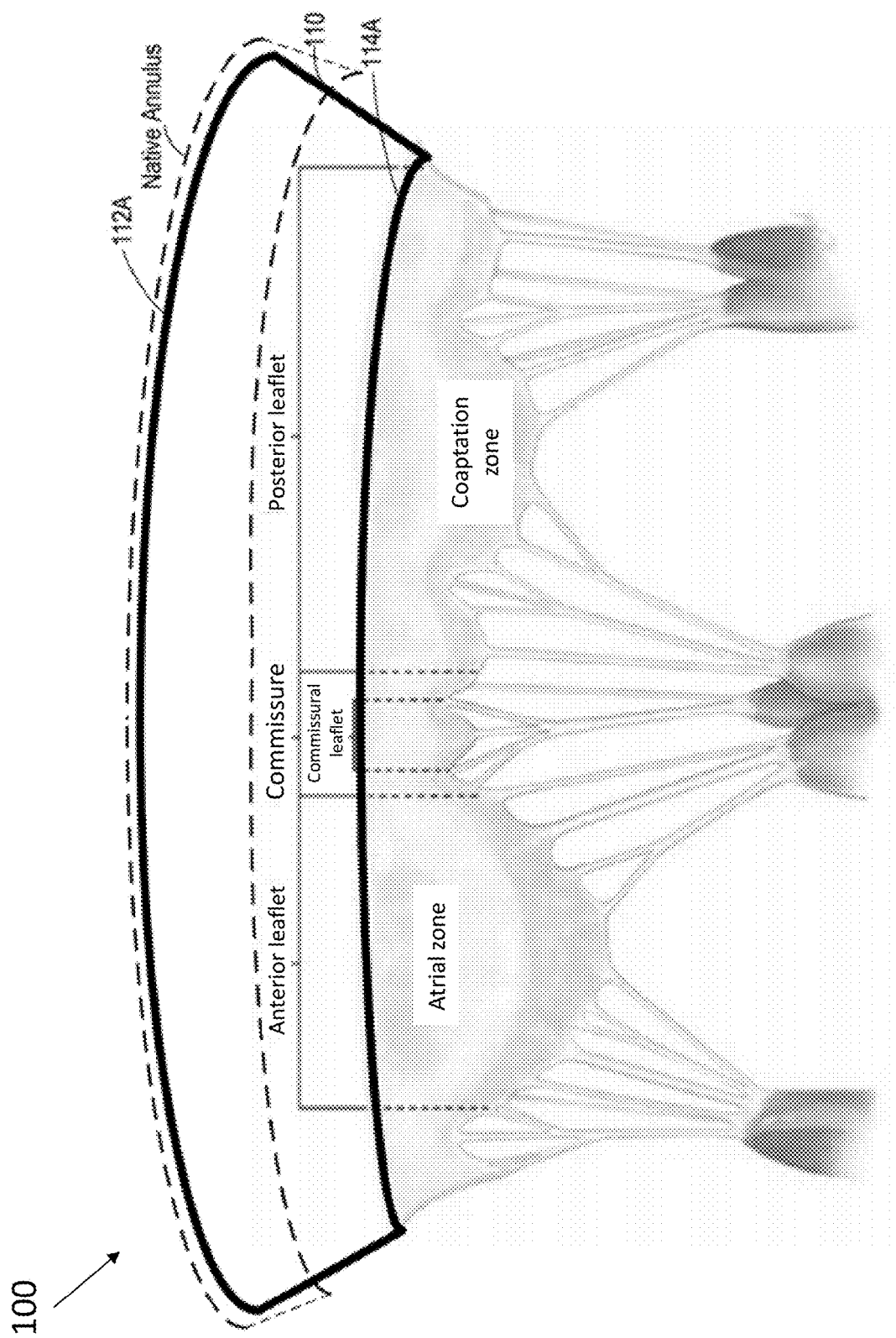
FIG. 4 is an opened and flattened view of the valve translocation device of FIG. 2 deployed within the native heart valve.

Referring now to FIG. 1 through FIG. 3, front view schematic illustrations of a native heart valve, a valve translocation device 100, and the valve translocation device 100 deployed within the native heart valve are shown, respectively, according to some embodiments. FIG. 4 is an opened and flattened view of the valve translocation device 100 deployed within the native heart valve.

The valve translocation device 100 (also referred to herein as "translocation device," "device," "patch," and "translocation collar device") is configured to be deployed in a heart within a body (e.g., of a human patient) and to effectively relocate at least a portion of a native heart valve to improve valve function (e.g., optimize valve leaflet coaptation during systole and minimize valve obstruction to blood flow during diastole). More specifically, in use, one or more native heart valve leaflets that have been detached from the heart can be coupled to the valve translocation device 100, and the translocation device 100 can be attached to the heart to place the native leaflet(s) in a position within the heart different from their native position (e.g., further into the ventricle of the heart). In this manner, for patients with damaged/dilated ventricles, for example, as discussed in further detail herein, moving at least a portion of the valve towards the ventricle can improve overall valve function.

As shown in FIG. 1, a native heart valve sits between an atrium and a ventricle, and includes an annulus from which leaflets are suspended. The annulus is made up of the confluence of three structures: the atrium, the ventricle, and the leaflets, with the leaflets operably connected to papillary muscles (not shown) via chordae tendinae. The translocation device 100 can be deployed to any suitable native valve within a heart such as, for example, the mitral valve and/or the tricuspid valve. For example, the translocation device 100 can be mitral valve translocation device configured to be deployed within the native mitral valve of a human heart to supplement and/or replace the functioning of the native mitral valve. As another example, the translocation device 100 can be a tricuspid valve translocation device configured to be deployed within the native tricuspid valve of a human heart to supplement and/or replace the functioning of the native tricuspid valve.

As described herein, during a translocation procedure, one or more native leaflets are detached from the patient and then reattached to the patient via the translocation device 100. The one or more native leaflets can be detached in any suitable manner, and the location of detachment can be any suitable location (e.g., it can vary from one native leaflet to another). For example, when operating on a native tricuspid valve, given the proximity of the tricuspid valve to portion(s) of the heart's conduction system, it is important not to disturb and/or damage the conduction system. Accordingly, in some instances, e.g., to avoid any interruption to the AV node (adjacent the native septal leaflet), a portion (e.g., about 2 mm to about 4 mm) of the native septal leaflet can remain attached to the native annulus, with the remaining portion of the native septal leaflet being detached therefrom. In this manner, the operator can avoid trauma to the conduction system. Further, with the portion of the septal leaflet remaining attached to the native annulus, the translocation device 100 can be secured (e.g., sewn) to the native anatomy without damaging the conduction system.

Figure 48:
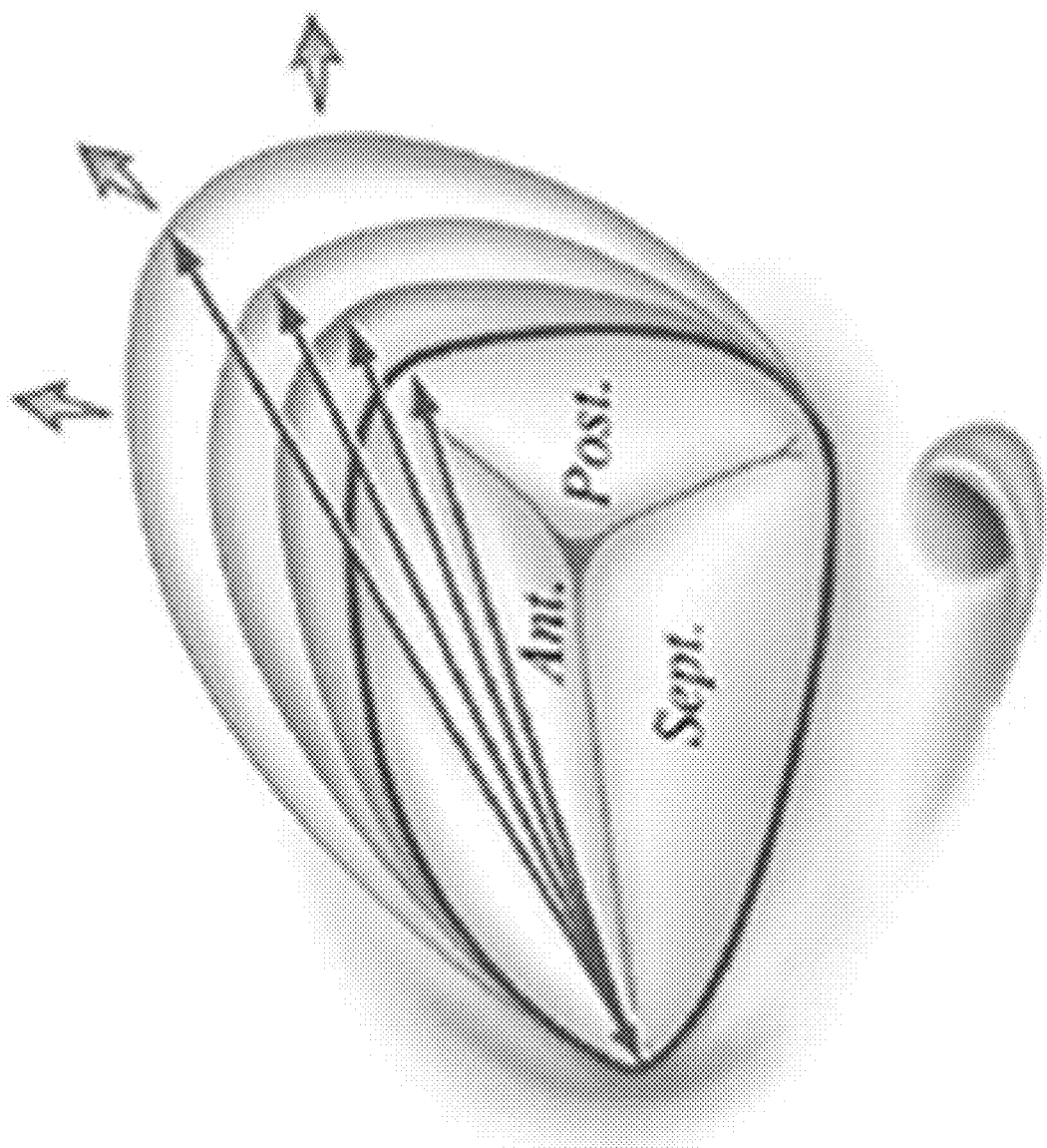
FIG. 48 is a schematic illustration of a tricuspid valve, showing that although the base of the anterior and posterior leaflets may dilate, the septal leaflet may not.

The translocation device 100 may be sized and/or shaped in any suitable manner. In some embodiments, the translocation device 100 is annular or ring-shaped. In some embodiments the translocation device 100 is partially, but not completely, annular or ring-shaped. In such embodiments, for example, the translocation device 100 can be semi-annular such that when implanted it extends circumferentially around a portion of the native annulus, e.g., a portion of the native annulus from which a native leaflet has been separated, and does not extend circumferentially around a portion of the native annulus from which a native leaflet remains intact. Regarding a native tricuspid valve, for example, in some instances, one or two of the three native leaflets can be separated from the native annulus and attached to the translocation device 100, while the remaining one or two native leaflets can be remain attached to extending from the native annulus; and in some implementations, the translocation device 100 can be semi-annular such that it circumscribes less than the entirety of the circumference of the annulus (e.g., less than 360 degrees). For example, regarding a native tricuspid valve, in some implementations, the translocation device 100 can be semi-annular such that it circumscribes and/or subtends the anterior and posterior leaflets, but not the septal leaflet. This is because in a tricuspid valve, although the bases of the anterior and posterior leaflets may dilate, the base of the septal leaflet does not. This is illustrated schematically in FIG. 48.

Further, each of the three native leaflets of a tricuspid valve form about 120 degrees of the orifice, or native annulus. Accordingly, in some embodiments, a semi-annular translocation device 100 can approximate 120 degrees (e.g., if subtending one leaflet) or 240 degrees (e.g., if subtending two leaflets). In various embodiments, the semi-annular translocation device 100 can approximate any suitable degrees less than 360 degrees, such as, for example, between about 90 and about 120 degrees, between about 120 and about 150 degrees, between about 150 and about 180 degrees, between about 180 and about 210 degrees, between about 210 and about 240 degrees, between about 240 degrees and about 270 degrees, between about 270 degrees and about 310 degrees, and between about 310 degrees and less than 360 degrees, and any suitable sub-ranges therebetween.

As shown in FIG. 2, the translocation device 100 includes a body 110. The body 110 includes or defines an annulus portion 112 and a leaflet portion 114 axially spaced from the annulus portion 112. The annulus portion 112 includes or defines an annulus end 112A that is configured to be attached to an annulus of a native heart valve after one or more native leaflets have been separated from the annulus. The leaflet portion 114 includes or defines a leaflet end 114A that is configured to be attached to the native heart valve leaflet(s).

With the leaflet end 114A attached to the native heart valve leaflet(s) and the annulus end 112A attached to the annulus, the native heart valve leaflet(s) are thereby connected to the native heart valve annulus (also referred to herein as "annulus" or "native annulus").

The body 110 can have any suitable shape and/or size. In some embodiments, the shape and/or size of the body 110 can vary across the body 110. For example, in some embodiments, the material of the body 110 may have a first thickness (i.e., distance between inner and outer diameter) in a first location, and a second thickness different from the first thickness in a second location different from the first location. The material of the body 110 can vary in thickness in any suitable manner, e.g., it can vary axially and/or circumferentially in any suitable direction (e.g., from annulus end 112A to leaflet end 144A, or vice versa). In some instances, for example, the thickness of the material of the body 110 at its annulus portion 112 can be different (e.g., larger or smaller) than the thickness of the material of the body 110 at its leaflet portion 114. In a similar manner, the thickness can vary between the annulus end 112A, the remaining annulus portion 112, the leaflet end 114A, and the remaining leaflet portion 114. In some instances, for example when translocating a native mitral valve, the body 110 may have a first thickness at a location configured for the anterior leaflet, and a second thickness less than the first thickness at a location configured for the posterior leaflet (similar to native leaflet thickness differences). As another example, given that native heart valve leaflets often vary in thickness, in some embodiments, the body 110 may have a first circumferential portion having a thickness approximately equal to the thickness of a first native leaflet, and a second circumferential portion having a thickness approximately equal to the thickness of the second native leaflet. As yet a further example, in some embodiments, the first circumferential portion could have a first thickness at a location configured to subtend an native anterior leaflet, and a second thickness, less than the first thickness, at a location configured to subtend a native posterior leaflet. Further, in some such embodiments, the body 110 may have additional circumferential portions having other thicknesses, e.g., a circumferential portion to be located at a commissure could have a thickness less than the thickness at the location configured to subtend the native anterior leaflet.

As another example, in some embodiments, the body 110 can vary in length between the annulus end 112A and the leaflet end 114A. In this manner, for example, a first circumferential portion can have a first length between the annulus end 112A and the leaflet end 114A while a second circumferential portion different from the first circumferentially portion can have a second length between the annulus end 112A and the leaflet end 114A that is different from the first length (see e.g., FIG. 7B).

The body 110 can be formed of any suitable material or combination of materials. In some embodiments, for example, the body 110 is formed of decellularized tissue, biological tissue, human pericardial tissue, bovine pericardial tissue, artificial fabric, polymer, and/or polytetrafluoroethylene.

The body 110 may be configured to simulate proper native valve function, including, for example, maximizing leaflet opening during diastole (i.e., blood flow from atrium to ventricle), and preventing backflow (i.e., from ventricle to atrium) during systole. The native mitral valve, for example, includes clefts between portions of the posterior leaflet, providing an increased perimeter and/or circumference, and which allow or encourage the posterior leaflet to sufficiently open (e.g., more than they otherwise would) during diastole, and the segmentation of the posterior leaflet by these clefts allows or encourages each segment to lie flat against the posterior ventricular wall, thereby limiting obstruction to blood flow.

To achieve similar functionality, in some embodiments, the leaflet portion 114 of the body 110 has a perimeter that is equal to or larger than the perimeter of the annulus portion 112. In this manner, the annulus portion 112 (and the annulus end 112A, in particular) can be sized (e.g., with a particular perimeter) to attach and/or mate with the native annulus sufficient to create a fluid-tight seal therebetween (e.g., to prevent leaks around the valve), and the leaflet portion 114 (and the leaflet end 114A, in particular) can be sized (e.g., with a relatively similar or larger perimeter) to create a sufficient opening and allow the native leaflets to sufficiently move away from the desirable blood flow path (e.g., during diastole).

In embodiments in which the perimeter of the leaflet portion 114 is larger than the perimeter of the annulus portion, the relatively larger perimeter of the leaflet portion 114 can be defined or accomplished in any suitable manner. In some implementations, for example, the body 110 can be formed with an annulus portion having a fixed perimeter less than a fixed perimeter of the leaflet portion (see e.g., FIG. 6C (top right), with the first edge 212 configured to be the leaflet portion 114 and the second edge 214 configured to be the annulus portion 112.

In some implementations, for example, the leaflet portion 114 includes one or more pleats (not shown). The pleat(s) can have an expandable portion (not shown) and a fixed portion (not shown) spaced from the leaflet end 114A. The expandable portion extends to the leaflet end 114A to define at least partially the relatively larger perimeter of the leaflet end 114A, and the expandable portion is configured to be attached to the native leaflet(s). The pleat(s) are configured to open or unfold (i.e., expand). In some embodiments, the material of the pleat can be stretchable, e.g., in addition to the pleat(s)' expandability or ability to unfold or open. In some embodiments, the pleat(s) are formed of a material that is not stretchable. Accordingly, the pleat(s) can be expanded, unfolded, opened, etc., regardless of the nature of the material of the pleat, to thereby provide an increased perimeter and/or diameter. The pleat(s) can not only increase the perimeter, as described above, but the pleat(s) can also mimic the natural segmentation (e.g., provided by clefts) of native valve leaflets, thereby further improving diastolic flow. While the leaflet portion 114 having one or more pleats is described above as providing for a perimeter larger than a perimeter of the annulus portion 112 (when expanded), in some embodiments, the leaflet portion 114 includes one or more pleats to provide for an increased perimeter (i.e., the leaflet portion 114 has a first configuration with a first perimeter, and a second, expanded configuration, with a second perimeter larger than the first perimeter), whereas the increased perimeter is less than or equal to the perimeter of the annulus portion 112. In this manner, a body 110 having a leaflet portion 114 with one or more pleats can have a leaflet portion 114 perimeter less than, equal to, or greater than, its annulus portion perimeter 112, depending on the particular implementation.

As described in further detail herein, some native leaflets have clefts or are otherwise characterized as bunched-up or circumferentially redundant in configuration. In this manner, when such a native leaflet is separated from a native annulus, the native leaflet is allowed to unfurl or circumferentially expand. Upon such expansion, the leaflet end in its unfurled state can, for example, be attached to the expandable portion of the pleat when the expandable portion of the pleat is in its expanded configuration.

The leaflet portion 114 can include any suitable number of pleats, e.g., one pleat, two pleats, three pleats, four pleats, five pleats, six pleats, or more. In some implementations, the number of pleats can match the number of native leaflets to be attached to the leaflet portion 114. For example, when dealing with a native mitral valve, in such implementations, a first pleat can be configured to be attached to an anterior native leaflet, and a second pleat can be configured to be attached to a posterior native leaflet. In some implementations, the one or more pleats can be configured to attach to one native leaflet, while another portion of the leaflet portion 114 configured to attach to another native leaflet can have no pleats. For example, when treating a native mitral valve, in such implementations, a portion of the leaflet portion 114 configured to be attached to the posterior leaflet has one or more pleats, and the portion of the leaflet portion 114 configured to be coupled to the anterior leaflet has no pleats.

The pleat(s) can have any suitable number of folds, any suitable size, and any suitable thickness, and the expandable portion can expand to any suitable size. In some implementations, for example, each pleat can add about 5 mm of perimeter to the expandable portion of the leaflet portion 114. So, for instance, three or four pleats can collectively add about 15 mm to about 20 mm to the perimeter. In some embodiments, the pleat(s) can fall anywhere within the range of about 2 mm to about 15 mm, when expanded.

The pleat(s) can be formed in any suitable manner. In some embodiments, for example, the pleat(s) can be formed by one or more cuts and one or more rolls and/or folds. For example, the body 110 can be formed of a sheet of material, and the sheet of material can be cut and then rolled or folded to create a pleat, as described in further detail herein. The pleat(s) can be held in place by any suitable technique. For example, the pleat(s) can be sewn in place using suture (e.g., a sterile surgical suture composed of polypropylene).

In some embodiments, in addition to or instead of the leaflet portion 114 including pleat(s), the leaflet portion 114 can include or define ruffles and/or waves along a portion or the entire circumference of the leaflet portion 114. In this manner, the ruffles and/or waves can provide similar functionality as the clefts of a native valve. Similar to as described with respect to the pleat(s), the ruffles and/or waves can be arranged, for example, to be coupled to a posterior native leaflet, an anterior native leaflet, or both.

The annulus portion 112 can be sized and configured to be coupled to the native valve annulus in any suitable manner. In some embodiments, for example, the annulus portion 112 can be secured to the native valve annulus using sutures. For instance, the sutures can be threaded through the annulus end 112A of the annulus portion 112 and through the native valve annulus, and then tied off to secure the body 110 to the native valve annulus. The sutures can be of any suitable type and size. In some embodiments, for example, the sutures are size 3-0.

In some implementations, the annulus portion 112 is secured to the native valve annulus using pledgets to limit or prevent any fluid leaks between the external surface of the annulus portion 112 and the native annulus when the translocation device 200 is secured to the native annulus. Any suitable number and arrangement of pledgets can be used, and the pledgets can be formed of any suitable material or combination of materials. In some embodiments, for example, the pledgets can be formed of a polymer, such as, a polytetrafluoroethylene. In some implementations, each pledget can be circumferentially distributed with a gap between each pledget (e.g., an interrupted pledgeted configuration).

In some embodiments, in addition to or instead of using the pledgets, the annulus end 112A includes or is formed into a collar that is configured to promote a fluid-tight seal between the external surface of the annulus end 112A or collar and the native annulus when the translocation device 100 is secured to the native annulus. In use, the translocation device 200 will be subjected to ventricular pressure with each systole cycle, and so such a collar can limit or prevent leakage caused by that ventricular pressure around the translocation device 110. In some implementations, the annulus end 112A has a thickness greater than a thickness of the remainder of the annulus portion 112, to in part, promote the fluid-tight seal described above. In some embodiments, the annulus end 112A is formed separately from, and then coupled to, the remainder of the annulus portion 112, while in some embodiments, the annulus end 112A is monolithically or integrally formed with the remainder of the annulus portion 112. In some embodiments, the annulus portion 112 is formed of a sheet of material, and the annulus end is monolithically or integrally formed with the remainder of the annulus portion 112 with multiple layers of the sheet of material, e.g., to form a collar. In such embodiments, in some implementations, the annulus end 112A is formed by rolling the sheet of material.

In some embodiments, the annulus end 112A is or includes a separate ring (e.g., a sewing ring) made from a material (e.g., Dacron) or combination of materials, and is coupled to the remainder of the annulus portion 112. In some implementations, the ring can be rigid or semi-rigid, and/or more rigid than the implementations described above in which the annulus end 112A is formed by rolling the sheet of material.

In some embodiments, the body 110 can include one or more alignment markers to assist an operator (e.g., a surgeon) to align and orient the body 110 within the native annulus. Similarly, in some instances, the native valve can be marked before detaching one or more native leaflets, such that the operator can match a marker on the body 110 with a marker on the native anatomy. For example, in some embodiments, the body 110 can include four alignment markers circumferentially distributed thereabout, e.g., at 12:00, 3:00, 6:00, and 9:00. The body 110 can include any suitable number of alignment markers, in any suitable arrangement. Further, the alignment markers can be formed of any suitable material. For example, one or more alignment markers can be formed of suture, and/or one or more alignment markers can be formed of ink.

Although various embodiments described herein include a leaflet portion having a leaflet end with a perimeter larger than the annulus portion perimeter (and/or the perimeter of the annulus end), in some embodiments, the leaflet portion has a leaflet end having a perimeter equal to the annulus portion perimeter (and/or the perimeter of the annulus end). In yet further embodiments, the leaflet portion has a leaflet end having a perimeter less than the annulus portion perimeter (and/or the perimeter of the annulus end). For example, when translocating a native tricuspid valve, in some implementations, the annulus end perimeter configured to be attached to the native annulus has a perimeter greater than the leaflet end perimeter configured to be attached to one or more native leaflets.

FIG. 5A is a flowchart illustrating a method 10 of deploying a valve translocation device to a desired location in a body, according to an embodiment. The method 10 includes, at 12, separating a native leaflet from a native annulus. The separated native leaflet has an annulus edge at which the native leaflet was joined to the native annulus. The native annulus has a leaflet edge at which the annulus was joined to the leaflet edge of the native leaflet.

The method 10 further includes, at 14, attaching to the leaflet edge of the native annulus an annulus end of an annulus portion a ring-shaped body. The annulus end has a perimeter. The method 10 further includes, at 16, attaching to the annulus edge of the native leaflet a leaflet end of a leaflet portion of the ring-shaped body. The leaflet portion is axially spaced from the annulus portion. The leaflet end has a perimeter larger than the perimeter of the annulus end.

Figure 5B:
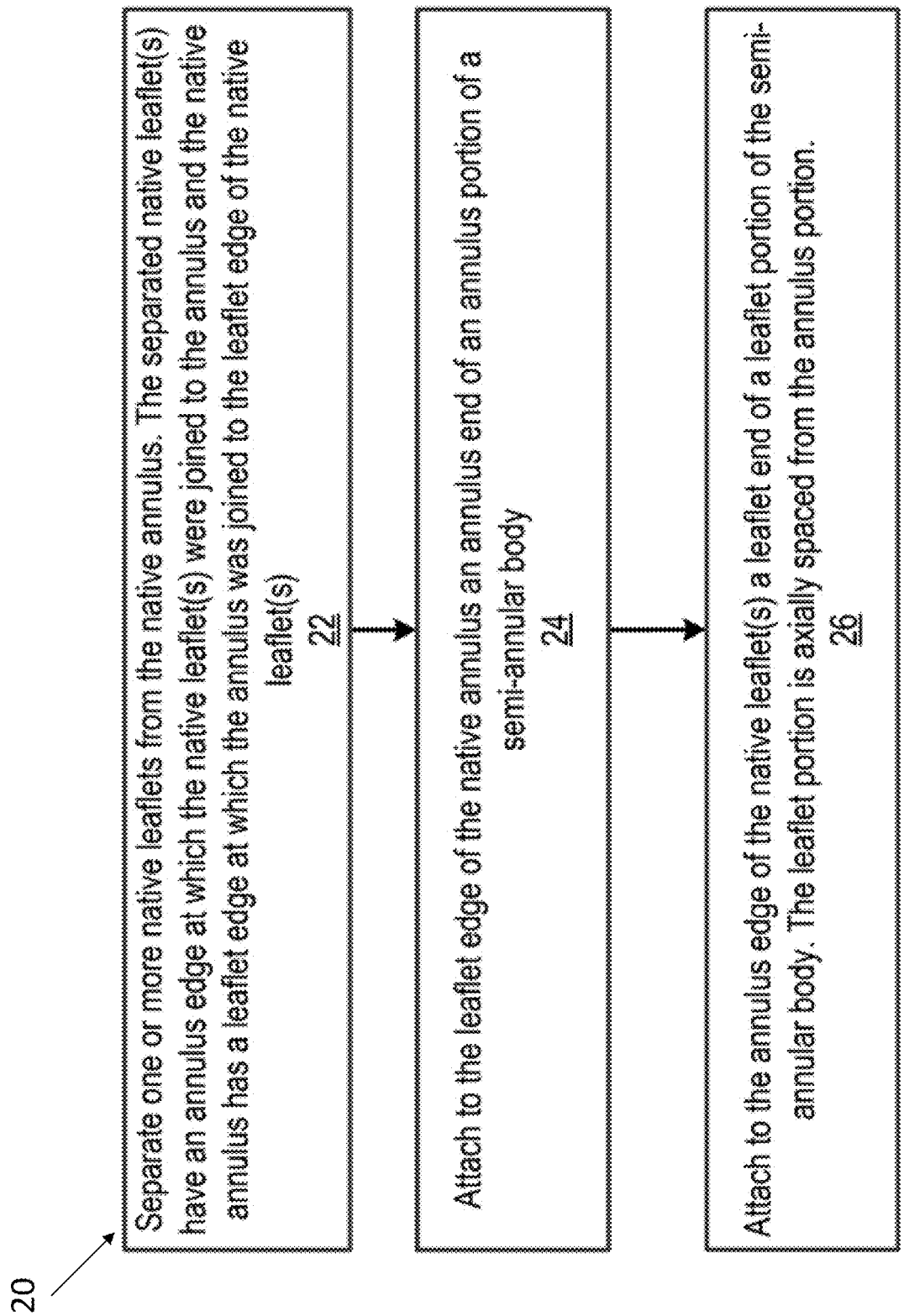
FIG. 5B is a flowchart illustrating a method of deploying a valve translocation device to a desired location in a body, according to an embodiment.

FIG. 5B is a flowchart illustrating a method 20 of deploying a valve translocation device to a desired location in a body, according to an embodiment. The method 20 includes, at 12, separating a native leaflet from a native annulus. The separated native leaflet has an annulus edge at which the native leaflet was joined to the annulus and the native annulus has a leaflet edge at which the annulus was joined to the leaflet edge of the native leaflet. The method further includes, at 24, attaching to the leaflet edge of the native annulus an annulus end of an annulus portion of a semi-annular body. The method further includes, at 26, attaching to the annulus edge of the native leaflet a leaflet end of a leaflet portion of the semi-annular body. The leaflet portion is axially spaced from the annulus portion.

The present invention provides devices for treating functional mitral regurgitation and methods of use thereof. The devices translocate a subject's mitral valve in an apical direction. The devices thereby treat mitral regurgitation while preserving a subject's original mitral valve and chordae tendinae.

Translocation Collar Device

Referring now to FIG. 6C, an exemplary translocation collar device 200 is depicted. Device 200 comprises a ring-like band of material having an exterior, an interior, a first edge 212, a second edge 214, and a width 216 in between. In some embodiments, first edge 212 is configured and shaped to attach to a subject's mitral annulus and second edge 214 is configured and shaped to attach to a subject's translocated mitral valve. In some embodiments, second edge 214 is configured and shaped to attach to a subject's mitral annulus and first edge 212 is configured and shaped to attach to a subject's translocated mitral valve. First edge 212 forms a first opening having an opening diameter. Second edge 214 forms a second opening having a second opening diameter. Contemplated dimensions for device 200 include but are not limited to first edge 212 having a diameter between about 20 mm and 60 mm, second edge 214 having a diameter between about 5 mm and 15 mm, and width 216 between about 5 mm and 15 mm. The first edge opening and the second edge opening together form a valvular aperture. In some embodiments, the first edge opening diameter is larger than the second edge diameter opening, while in other embodiments the second edge opening diameter is larger than the first edge diameter opening, such that device 200 has a substantially truncated (e.g., frustum conical-like) conical shape.

Referring now to FIG. 6C, an exemplary translocation collar device 200 is depicted. Device 200 can be constructed the same as or similar to, and can function the same as or similar to, any of the valve translocation devices described herein. Thus, portions of the device 200 are not described in further detail herein. Device 200 includes a ring-like band of material having an exterior, an interior, a first edge 212 (e.g., a leaflet end of a leaflet portion), a second edge 214 (e.g., an annulus end of an annulus portion), and a width 216 in between. In some embodiments, first edge 212 is configured and shaped to attach to a subject's mitral annulus and second edge 214 is configured and shaped to attach to a subject's translocated mitral valve. In some embodiments, second edge 214 is configured and shaped to attach to a subject's mitral annulus and first edge 212 is configured and shaped to attach to a subject's translocated mitral valve, e.g., such that the first edge 212 has a perimeter greater than a perimeter of the second edge 214 (to which the native valve leaflet(s) are attached). First edge 212 forms a first opening having an opening diameter. Second edge 214 forms a second opening having a second opening diameter. Contemplated dimensions for device 200 include but are not limited to first edge 212 having a diameter between about 20 mm and 60 mm, second edge 214 having a diameter between about 5 mm and 15 mm, and width 216 between about 5 mm and 15 mm. The first edge opening and the second edge opening together form a valvular aperture. In some embodiments, the first edge opening diameter is larger than the second edge diameter opening, while in other embodiments the second edge opening diameter is larger than the first edge diameter opening, such that device 200 has a substantially truncated (e.g., frustum conical-like) conical shape.

In some embodiments, first edge 212 or second edge 214 is sized to have substantially the same diameter as the diameter of a subject's mitral annulus in a dilated condition, while the opposing edge is sized to have substantially the same diameter and shape of a subject's normal mitral valve in an undilated condition. In some embodiments, device 200 is formed from a length of material having width 216 and an arc-shape, wherein an outer edge has a length equal to the circumference of first edge 212 and an inner edge has a length equal to the circumference of second edge 214, such that the thin band of material can be joined end-to-end to form the substantially truncated conical shape of device 200.

Referring now to FIG. 7A and FIG. 7B, in some embodiments device 200 has an oblique or slanted truncated cone-like shape, in which first edge 212 and second edge 214 are not concentric. For example, while in some embodiments first edge 212 and second edge 214 can be in parallel alignment, in other embodiments first edge 212 and second edge 214 can have an angle difference that is between about 30 degrees and about 80 degrees, such as an angle difference between about 60 degrees and about 70 degrees. Device 200 has a variable width 216, thereby forming a first height 218 and a second height 220, wherein a first height 218 can be greater, such as in a posteromedial segment. While a symmetrical device 200 can be advantageous for subjects having global left ventricular dysfunction that require symmetric displacement of the mitral valve into the ventricle, a device 200 having an oblique or slanted shape can be advantageous to treat a subject's particular condition, such as a greater height at a posteromedial portion for inferior ischemic myopathy.

Referring now to FIG. 8A through FIG. 8C, in some embodiments device 200 can further include an annuloplasty ring 222. Annuloplasty ring 222 can be attached to the interior or exterior of first edge 212, second edge 214, or both. In some embodiments, annuloplasty ring 222 can have an asymmetrical shape or non-circular shape sized to fit the anatomy of a subject, as would be understood by those skilled in the art. Annuloplasty ring 222 can have any typical size, such as a size 26, 28, or 30 annuloplasty ring or the like.

Figure 9A:
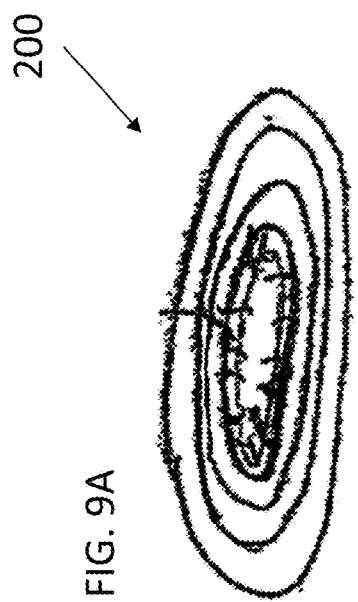
FIG. 9A through FIG. 9C depict exemplary translocation collar devices having adjustable heights.
Figure 9B:
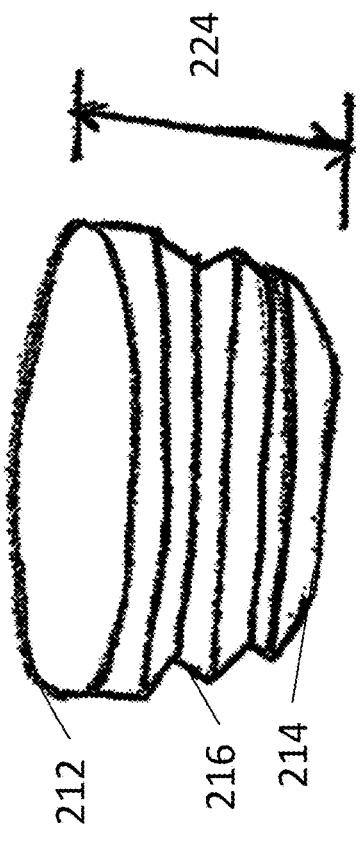
Figure 9C:
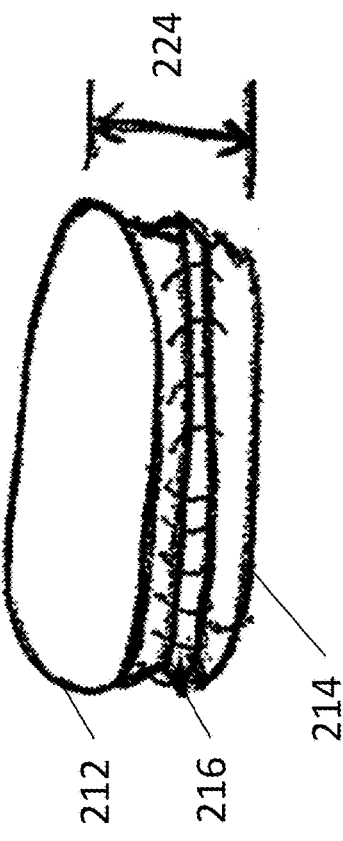

Referring now to FIG. 9A through FIG. 9C, in some embodiments device 200 can further include concentric folding aligned in parallel with first edge 212 and second edge 214 along width 216, providing device 200 with a customizable height 224. Device 200200 can be used with unaltered concentric folding to provide a variable range of movement after implantation. A variable range of movement can be advantageous by permitting device 200 to adapt to varying heart rates. Device 200 can also have height 224 customized to the dimensions of a subject by placing a suture or adhesive along the concentric folding, thereby fixing height 224 (FIG. 9C).

Figure 47B:
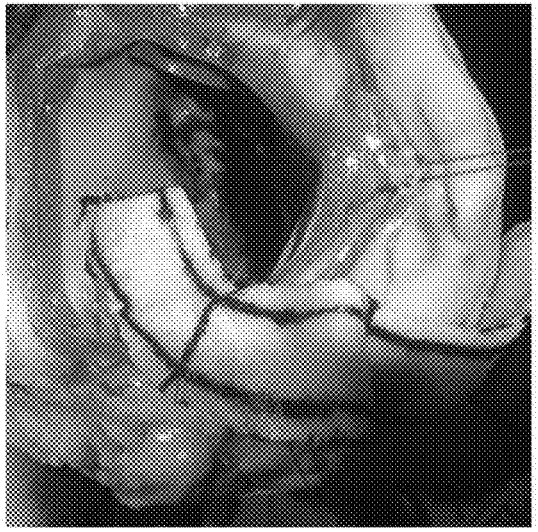
FIG. 47A through FIG. 47D depict a sequence of implanting a prototype translocation collar device having 2 mm upper and lower tabs for horizontal mattress sutures.
Figure 47D:
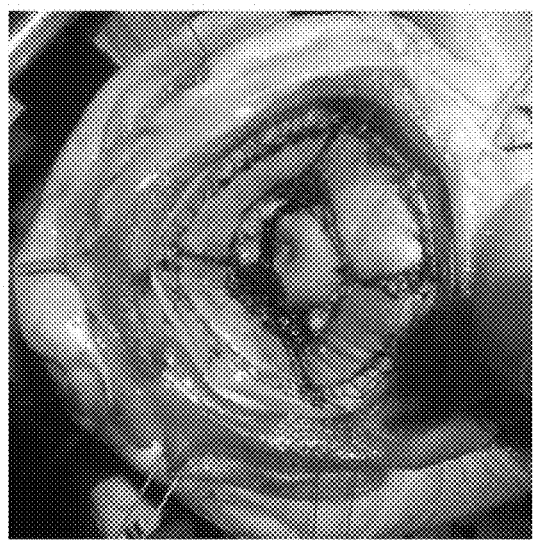
Figure 47A:
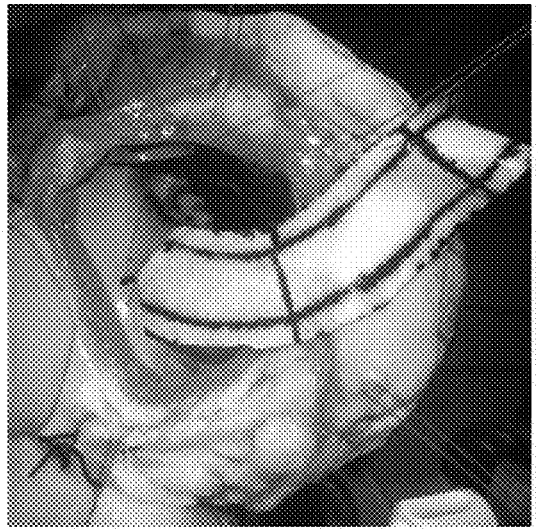
Figure 47C:
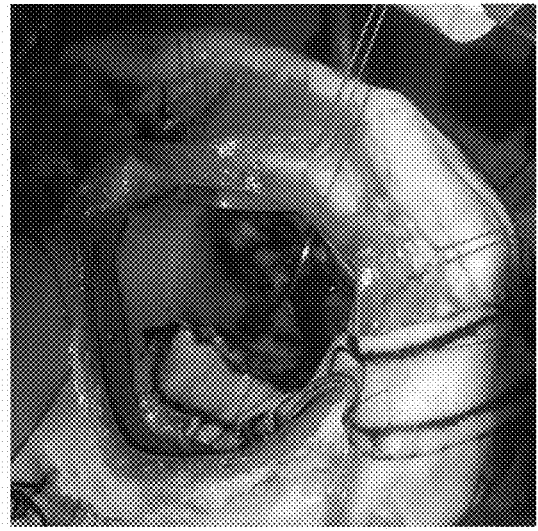

Referring now to FIG. 10A through FIG. 10C, in some embodiments device 200 can further include one or more sewing cuffs 26. Sewing cuffs 26 can be attached to the exterior of device 200, to first edge 212, to second edge 214, or combinations thereof. Sewing cuffs 26 provide device 200 with larger and more durable attachment surfaces for suturing to a subject's tissues. In some embodiments, device 200 can further include a small extension beyond first edge 212 and second edge 214 to increase attachment surfaces for sutures (e.g., FIG. 47A, 2 mm extensions marked by solid line parallel to annular and apical edges of the collar device).

Figure 11A:
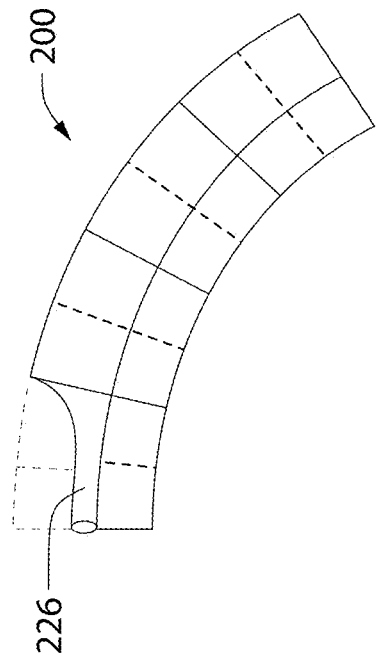
FIG. 11A through FIG. 11D depict the progression of the formation of an exemplary translocation collar device.
Figure 11B:
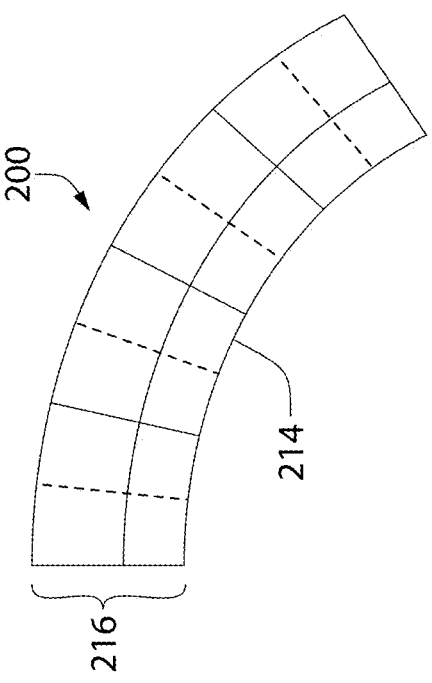
Figure 11C:
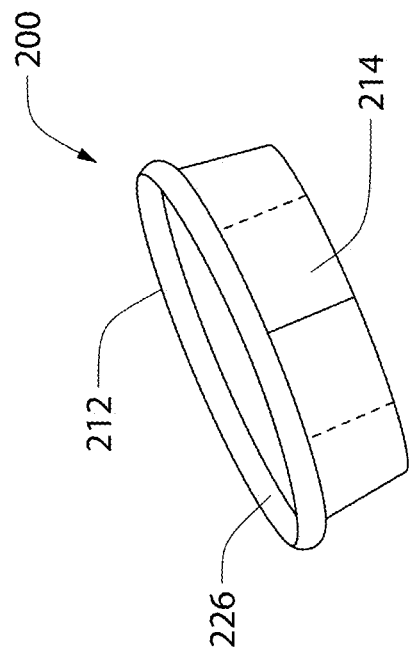
Figure 11D:
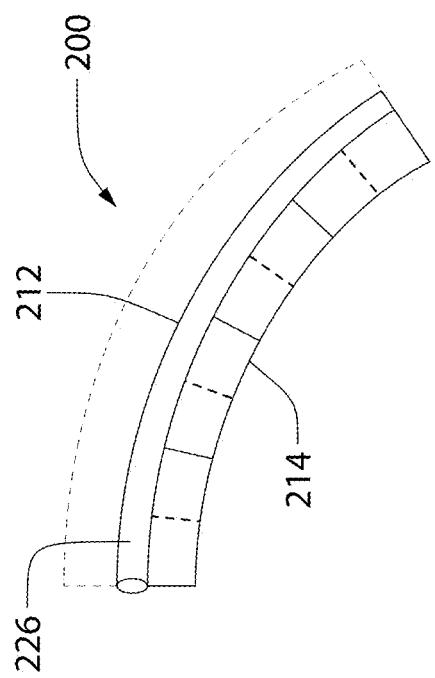

Referring now to FIG. 11A through FIG. 11D, in some embodiments device 200 includes a rolled sewing cuff or collar 26 on an outer circumference. For example, as shown in FIG. 11A through FIG. 11D, an exemplary device 200 is created using a full template. For demonstration purposes, device 200 in FIG. 11A is described with the dimensions of 25 mm in depth (width 216), 105 mm in length on an outer arc, and 95 mm in length on an inner arc. It should be appreciated that device 200 of the present invention are not limited to any particular size. In FIG. 11B, the top portion of the template (about 15 mm in depth) (e.g., the annulus portion) is rolled over twice and secured with a running suture to the body of device 200 to form the sewing cuff or collar 26. Markings on the template and device 200 show quadrants (unbroken lines) and eighth marks (dashed lines), which can be transcribed onto the pericardium of a patient. The completed sewing cuff or collar 26 is shown in FIG. 11C, and the completed frustrum-shaped device 200 is shown in FIG. 11D.

Figure 12:
FIG. 12 is a photograph showing the rolled sewing cuff or collar of an exemplary translocation collar device after it has been completed but before it is ready to be implanted. The device must then be sewn end-to-end into a cylinder/frustrum shape. Markings on the device shown quadrants (unbroken lines) and eighth marks (dashed lines). These markings facilitate proper orientation and suturing of the device to the native mitral annulus and native mitral valve.

FIG. 12 is a photograph demonstrating the rolled sewing cuff or collar 26 of device 200 after it has been completed but before it is ready to be implanted. Device 200 can then be sewn end-to-end into a cylinder/frustrum shape. Markings on device 200 shown quadrants (unbroken lines) and eighth marks (dashed lines). These markings facilitate proper orientation and suturing of device 200 to the native mitral annulus and native mitral valve.

FIG. 13 demonstrates the rolled sewing cuff or collar 26 of device 200 ready for suturing. While this is one embodiment, there are many other embodiments; device 200 could be constructed by attaching a sewing cuff 226 to the main body of device 200. Sewing cuff 226 can be made of any material, such as a Dacron sewing ring similar to that which is seen on commercially available replacement valves, to which device 200 would be attached. While the rolled sewing cuff or collar 26 may be flexible, there may be situations in which the sewing cuff 226 would be semirigid or rigid. The rolled edge serves as a gasket to seal the outer suture line, which is subject to ventricular pressure with each systole.

Figure 14:
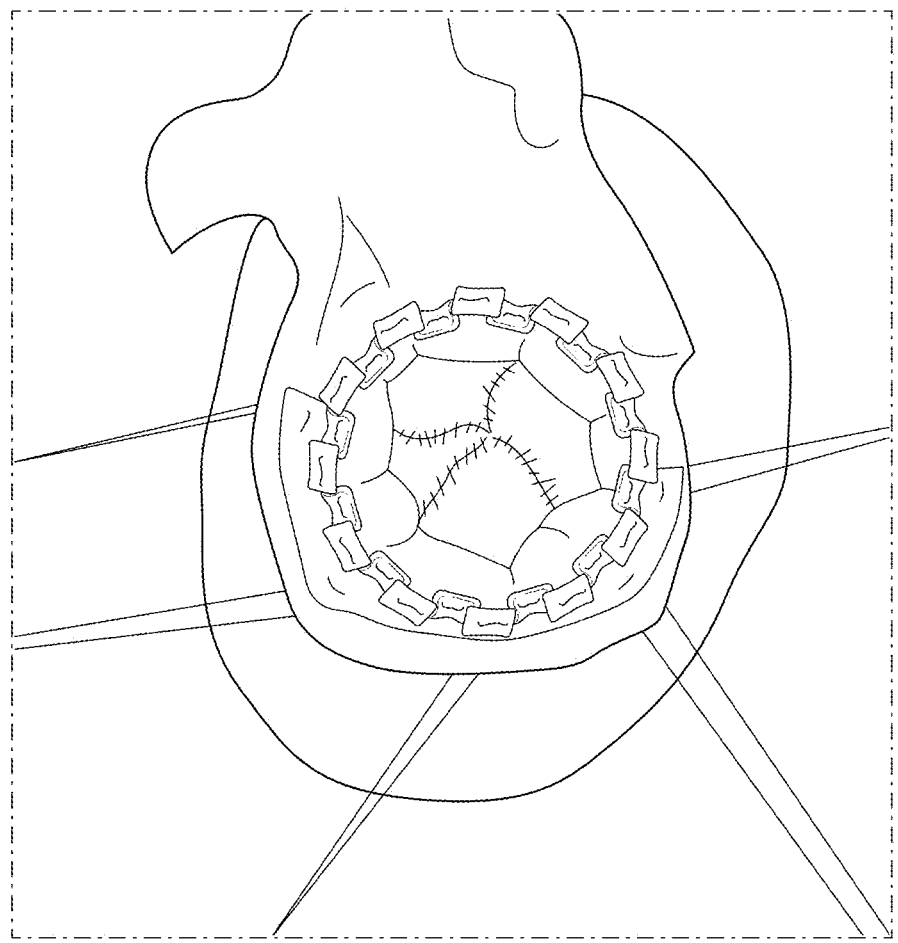
FIG. 14 is a photograph showing the use of an interrupted pledgeted horizontal mattress suture line using relatively small pledgets.

In some embodiments, suturing of device 200 can be enhanced using an interrupted pledgeted horizontal mattress suture line using relatively small pledgets (FIG. 14). While typical mitral valve replacement is done using similar sutures, usually 12-14, device 200, in some implementations benefits from using smaller (e.g., 7 mm×3 mm×1.5 mm, firm) Teflon pledgets and to place 20 or more total pledgeted sutures as shown in FIG. 14. Use of a smaller number of large pledgets, in some instances, leads to constriction/decreased diameter of the outer suture line. In some embodiments, the use of a rigid or semi-rigid sewing ring can allow for fewer pledgets to be placed, more similar to typical mitral valve replacements. In some embodiments, the rolled outer edge of device 200 is flexible and provides two advantages. A flexible device 200 facilitates sliding device 200 down into the annulus prior to suturing (i.e., the surgeon slides device 200 down over all the sutures), which is in contrast to a stiff/rigid sewing ring (like a standard prosthetic replacement valve) which is oftentimes difficult to place into the annulus. A flexible device 200 may also better preserve annular motion (the normal mitral annulus expands and contracts during the cardiac cycle) and may also better preserve ventricular function at the base of the heart (which can be compromised after insertion of a conventional rigid annuloplasty ring or a mitral prosthesis).

Figure 15:
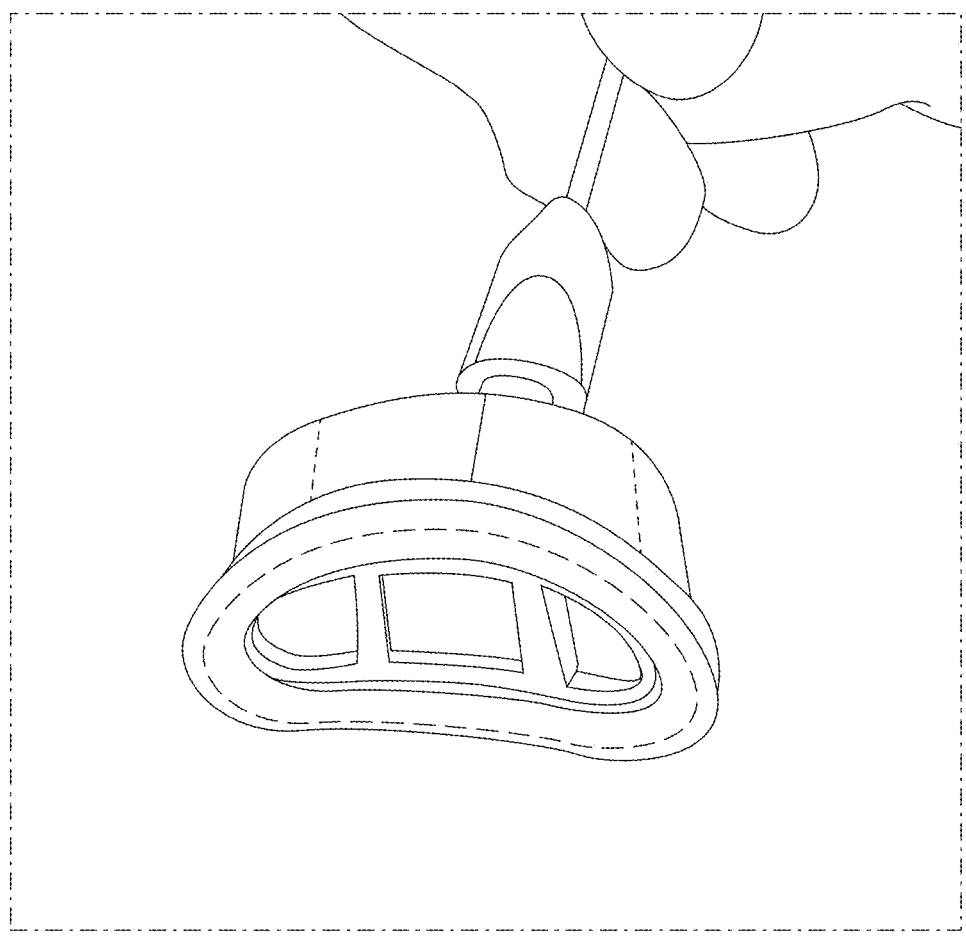
FIG. 15 is a photograph showing an exemplary translocation collar device mounted on a rigid circular holder, in order to facilitate suturing of the device. In this example, a mitral annuloplasty ring has been used as the rigid circular holder.
Figure 16:
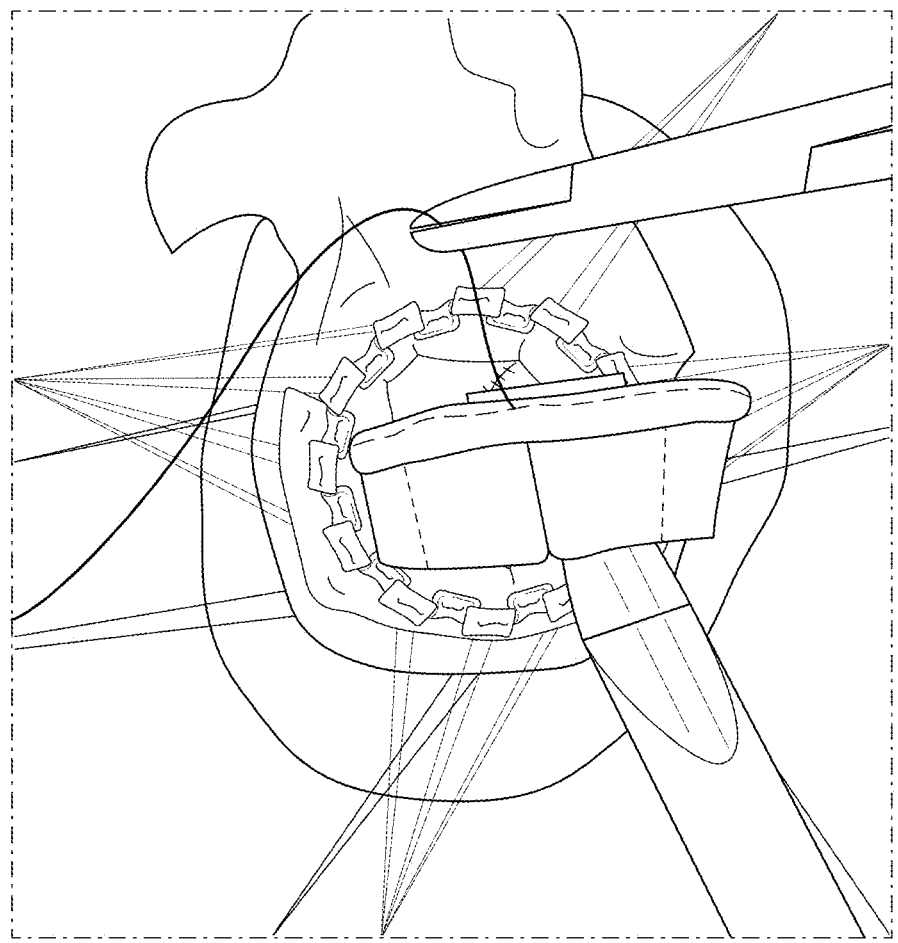
FIG. 16 is a photograph showing the placement of the pledgeted stitches through the sewing cuff of an exemplary translocation collar device.
Figure 17:
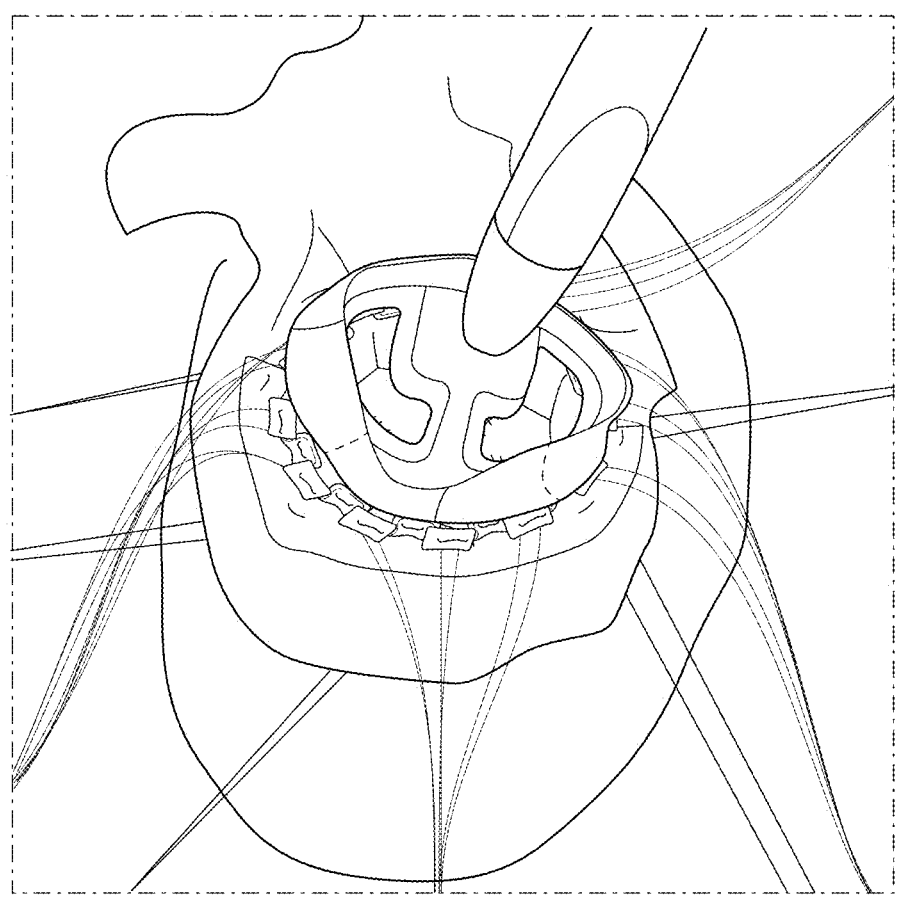
FIG. 17 is a photograph showing the translocation collar device seated down into the annulus of the valve once all stitches are placed.
Figure 18:
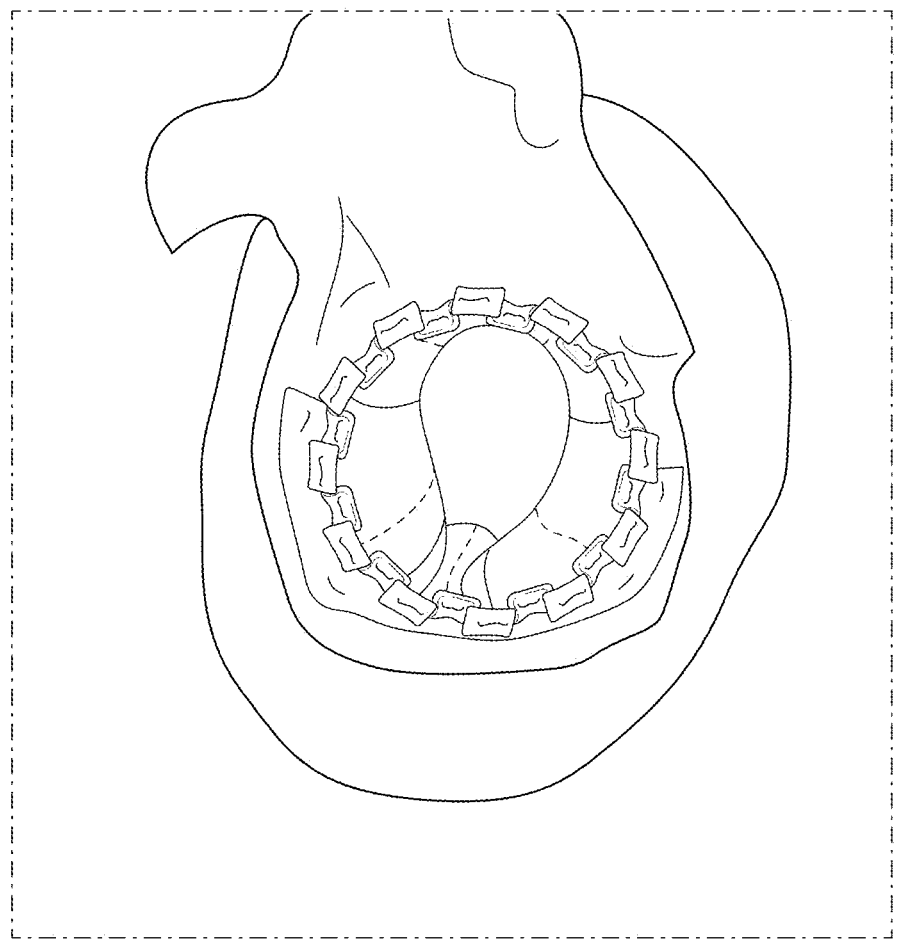
FIG. 18 is a photograph showing the holder removed, all pledgeted stitches tied, and the translocation collar device naturally inverting when pushed down into the ventricle. At this point the native mitral leaflets can be sewn to the bottom (free edge) of the device.

FIG. 15 demonstrates device 200 mounted on a rigid circular holder in order to facilitate suturing of device 200. In this example a mitral annuloplasty ring is being used as the rigid circular holder. Additional holder styles may be circular in shape. However, as the translocation procedure does not incorporate annuloplasty, the holder ring is removed prior to implantation (see FIG. 16 through FIG. 18). Sutures are placed as shown in FIG. 15 (and in typical fashion for a conventional mitral valve replacement) with the pledget on the atrial surface of the annulus and the sutures emerging on the ventricular side of the annulus. They are then placed in the rolled sewing cuff or collar 26 of device 200. While various suture sizes can be used, size 3-0 sutures are of optimal size in some implementations. Device 200 in FIG. 12 has been everted from its final position in a patient. Once the sutures are placed through the rolled edge, device 200 is lowered into position, the holder sutures on the holder divided, and the holder removed. At this point, device 200 is inverted back into the ventricle, the outer sutures tied, and the native mitral leaflets can be sewn to the free edge (e.g., leaflet end of leaflet portion) at the bottom of device 200.

Sizing of device 200 is now described. The circumference of the native mitral valve annulus can be measured using any suitable technique, including for example, transesophageal echocardiography (TEE) during mid-diastole; typically patients with secondary MR have circumferences between 100 and 140 mm. Device 200 sizes implanted range between 70 mm outer circumference (60 mm inner circumference) and 105 mm outer circumference (95 mm inner circumference), with the most commonly chosen size being 105×95 mm. Device 200 can, in some embodiments, for example, have a constant length (referred to as the width of device 200), such as 10 mm for example, between the outer and inner circumference (e.g., 150 mm by 95 mm), while in some embodiments the length (width) between the outer and inner circumference can be vary. In some such embodiments, for example, device 200 can be wider in some locations (e.g., the anterior leaflet aspect) than in others (e.g., the posterior leaflet portion).

Geometries of device 200 are now described. In order to simulate the native mitral valve function and to maximize leaflet opening during diastole, it is important to maximize the diameter of the inner suture line (e.g., the leaflet end of the leaflet portion). In some embodiments, the circumference and/or the diameter of the inner suture line is larger than that of the outer suture line (e.g., the annulus end of the annulus portion). In order to achieve this goal, another embodiment of the present invention includes one or more pleats in the portion of device 200 that subtends the posterior leaflet (e.g., the leaflet portion). As an example implementation, each pleat can add 5 mm of circumference to the inner suture line. Device 200 can include any suitable number of pleats. In an exemplary embodiment, device 200 includes 3 to 4 total pleats. In aggregate, using the example of each pleat adding 5 mm of circumference, the 3 to 4 pleats adds 15 to 20 mm to the circumference of the inner suture line. In some embodiments, device 200 can include multiple pleats, with one or more of the pleats being different in size; e.g., a first pleat can add 4 mm of circumference and a second pleat can add 6 mm of circumference. Additional embodiments of device 200 can include more than 4 pleats or can add length to the inner suture line by creating a ruffle or wave effect along device 200. Pleats, ruffles, and/or waves can be placed on either the anterior, posterior, or both leaflets. The native mitral valve is characterized by "clefts" between portions of the posterior leaflet (FIG. 19), which allow the posterior leaflet to open maximally during diastole (when blood flows from the atrium to the ventricle) and in fact the segmentation of the posterior leaflet by these clefts allows each segment to lie flat against the posterior ventricular wall and cause a minimum amount of obstruction to blood flow. The pleats serve the dual function of increasing the overall circumference of the inner suture line to create a larger opening in diastole and of mimicking the "segmentation" of the native posterior leaflet to contribute to improved diastolic flow.

Figure 20E:
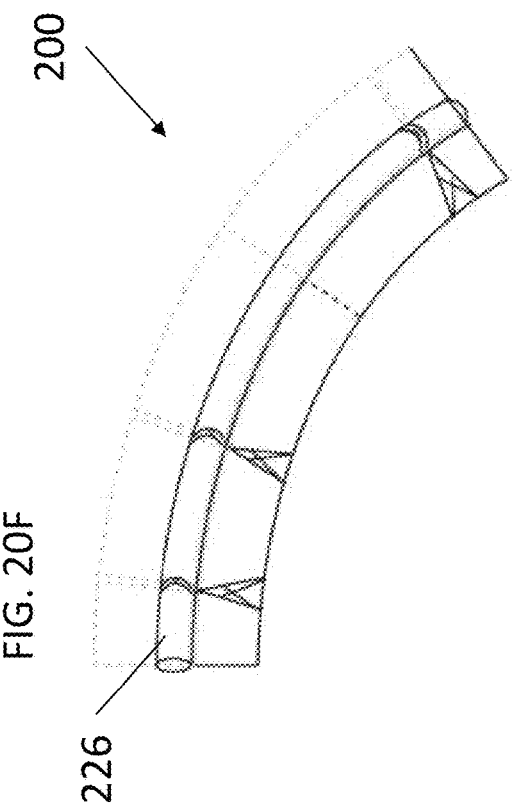
Figure 20F:
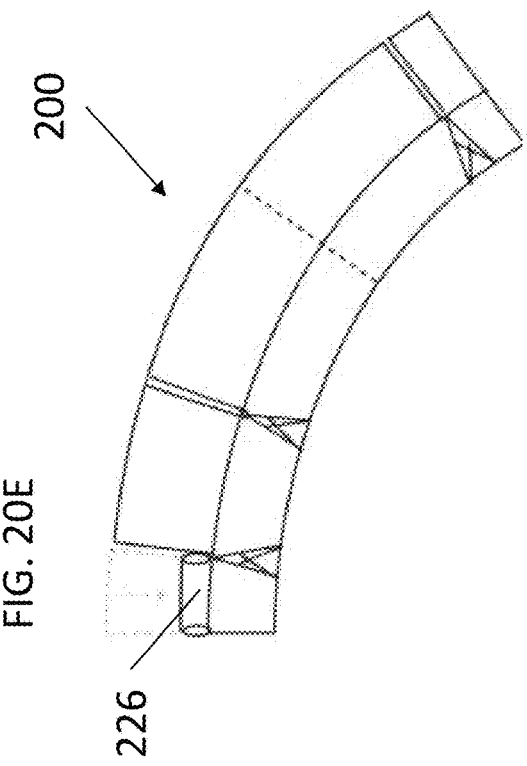
Figure 20G:
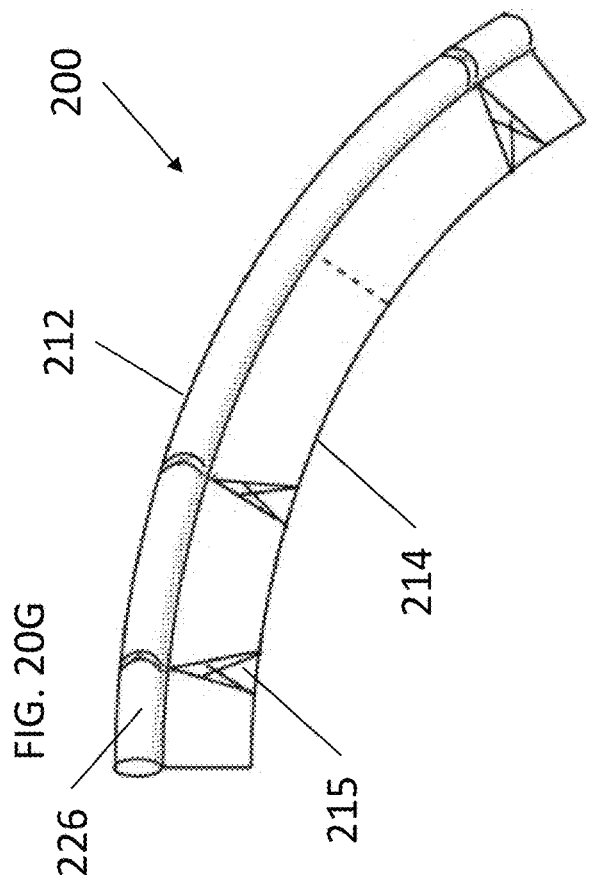
Figure 20H:
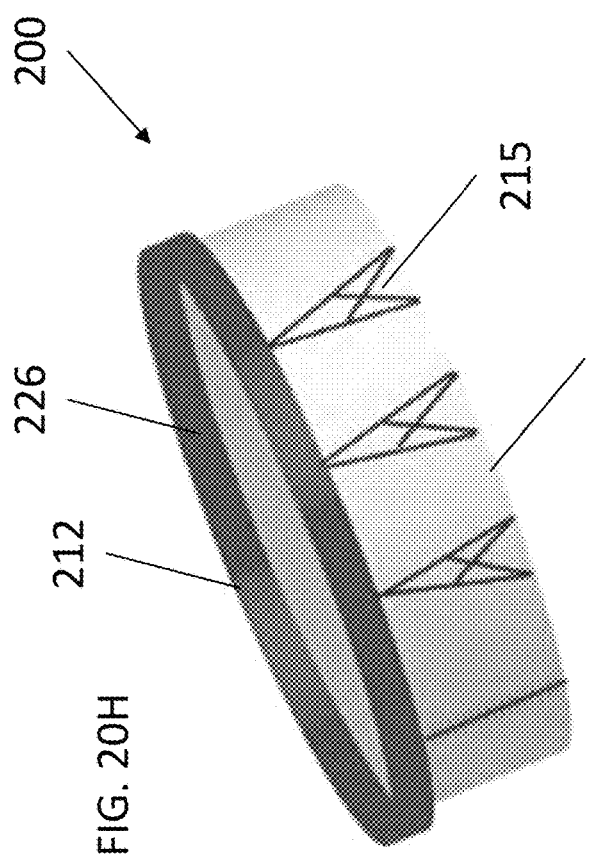

The progression of the creation of device 200 with pleats 215 is shown in FIG. 20A through FIG. 20H. The starting full template is shown in FIG. 20A. For demonstration purposes, device 200 in FIG. 20A is described with the dimensions of 25 mm in depth, 105 mm in length on an outer arc, and 95 mm in length on an inner arc. It should be appreciated that device 200 is not limited to any particular size. The top portion of the template (15 mm in depth) is rolled over twice to form the sewing collar, leaving about 10 mm below the collar to form the depth of device 200. Markings on the template and device 200 show the location of each plate (X-marks) and the location of the center of device 200 to be placed at the center of the anterior leaflet (dashed line). Pleat 15 location "X" is the portion of the plate on the sewing collar and 'x' is the portion on device 200 proper. The "X" portion on the sewing collar is cut out (FIG. 20B), while the 'x' portion on device 200 is sewn together using a running suture (FIG. 20C) to form a pleat 15 (FIG. 20D). The sewing collar is then rolled twice and stitched down with a running suture (FIG. 20E). Next, figure-of-eight stitches are placed in the sewing collar at the locations where the pleats 215 were formed to ensure no leakage from the collar (FIG. 20F). This embodiment is also applicable to the translocated tricuspid. The completed pleated device 200 is shown in FIG. 20G; the completed frustrum-shaped device 200 is shown in FIG. 20H.

Figure 20I:
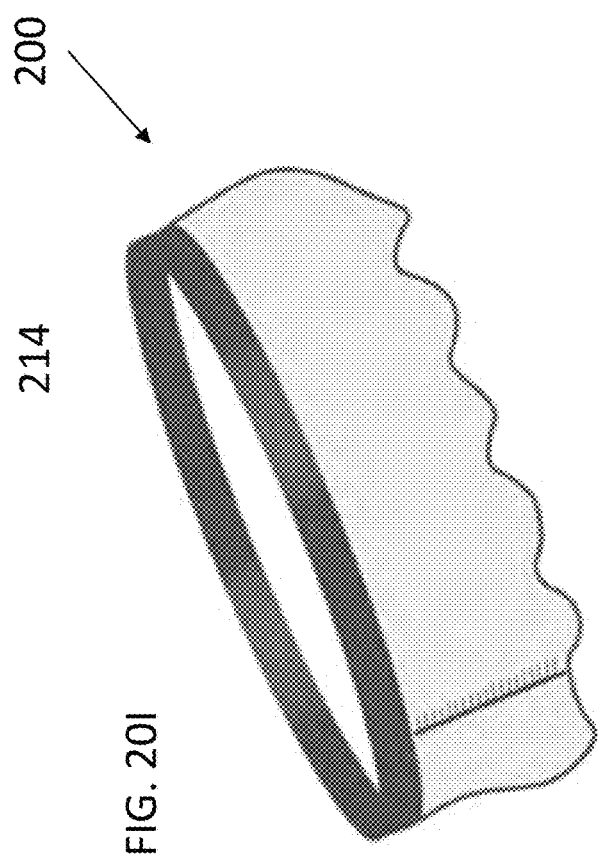
Figure 21:
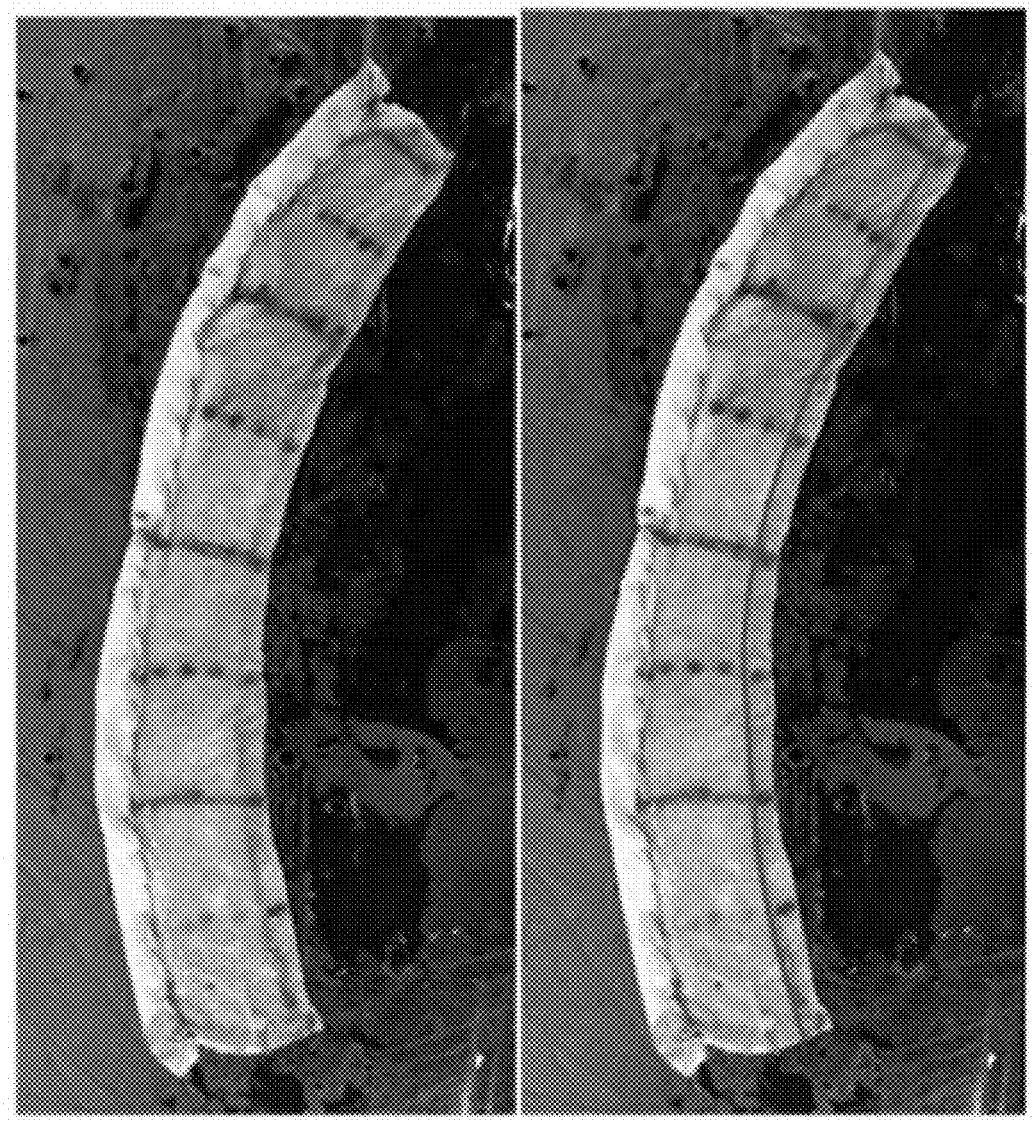
FIG. 21 shows (top) an exemplary translocation collar device showing colored marks for alignment and (bottom) tissue below the red line is given in order to provide room to attach the inner suture line to the native mitral valve—this can be left long and trimmed back as necessary.

While pleats 215 are described for demonstration purposes to be 5 mm in size, they can be smaller or larger as needed (e.g., 2 to 15 mm). The number of pleats 215 can vary between 2 to 6 or more, for example. The length of the inner suture line can increased using alternative methods, such as by ruffling device 200 instead of or in addition to creating distinct pleats 215 (FIG. 20I). Markers (either suture or colored marks) can be placed on device 200 at the 12 o'clock, 3 o'clock, 6 o'clock, and 9 o'clock positions, and/or other suitable locations. These markers help a surgeon to sew and align the inner suture line with the native valve, which are marked respectively at similar locations prior to be detached from its native annulus. While the depth of device 200 below the sewing collar is described for demonstration purposes to be about 10 mm, an exemplary device 200 can have a depth of between about 5 mm to 25 mm depending on a patient's geometry. In some embodiments, device 200 can include a few extra millimeters of depth (about 1 to 3 mm) on the inner suture line portion in order to provide room to attach the inner suture line (marked in FIG. 21).

FIG. 22A depicts a completed pleated device 200 (having 4 pleats 215) mounted to a mitral valve replacement sizer (left) and unmounted (right) showing the 'anterior leaflet' portion, wherein device 200 is prototyped using surgical drape material. FIG. 22B depicts a prototype device 200 mounted to a mitral valve sizer (left) and unmounted (middle, right) showing 'posterior leaflet' portion with pleats 215. FIG. 22C depicts additional views of the unmounted device 200 from the atrial/annular side (left) and the ventricular/leaflet side (right).

The translocation devices of the present invention can be constructed from any material suitable for implanting, including but not limited to biocompatible polymers, fabrics, plastics, metals, as well as biological tissue such as autografts, allografts, xenografts, and engineered tissue constructs, and combinations thereof. Exemplary materials include Dacron® cloth (flexibility modified by albumin coating), gluteraldehyde-fixed bovine pericardium, a subject's native pericardium, and the like.

In some embodiments, the devices are made from autologous pericardium treated with 0.625% glutaraldehyde for 2-3 minutes then rinsed with saline. The devices can also be made from bovine or other animal tissue pericardium. Bovine pericardium (usually treated with glutaraldehyde) is widely used for valvular replacement prostheses and for intracardiac and intravascular patching. The devices can also have a varied thickness. For example, the portion of the devices that subtends the native anterior mitral valve leaflet can be thicker (such as the typical thickness of native anterior leaflet) and the portion that subtends the posterior leaflet can be thinner (to replicate the native leaflet, which is thinner than the anterior leaflet).

Materials including tissue can be can be treated with a sterilization step. The sterilization step can apply any suitable sterilization method, including but not limited to radiation (e.g., gamma radiation, x-ray radiation, ultraviolet sterilization, and electron beam processing), gaseous formaldehyde, carbon dioxide, ozone, ethylene oxide, peracetic acid, ethanol, hydrogen peroxide, and the like. The tissue can be provided with original cells, completely decellularized, or decellularized and reseeded with host cells. In some embodiments, the tissue can be enhanced with one or more additives, including but not limited to one or more additional extracellular matrix material and/or blends of naturally occurring extracellular matrix material, such as collagen, fibrin, fibrinogen, thrombin, elastin, laminin, fibronectin, vitronectin, hyaluronic acid, chondroitin 4-sulfate, chondroitin 6-sulfate, dermatan sulfate, heparin sulfate, vixapatin (VP12), heparin, and keratan sulfate, proteoglycans, and combinations thereof. The additives can include natural peptides, such as glycyl-arginyl-glycyl-aspartyl-serine (GRGDS), arginylglycylaspartic acid (RGD), and amelogenin. In some embodiments, the additives can include nutrients, such as bovine serum albumin. In some embodiments, the additives can include vitamins, such as vitamin B2, vitamin Ad, Vitamin D, Vitamin E, and Vitamin K. In some embodiments, the additives can include nucleic acids, such as mRNA and DNA. In some embodiments, the additives can include natural or synthetic steroids and hormones, such as dexamethasone, hydrocortisone, estrogens, and its derivatives. In some embodiments, the additives can include growth factors, such as fibroblast growth factor (FGF), transforming growth factor beta (TGF-β), and epidermal growth factor (EGF). In some embodiments, the additives can include a delivery vehicle, such as nanoparticles, microparticles, liposomes, viral and non-viral transfection systems. The additives can include one or more therapeutics. The therapeutics can be natural or synthetic drugs, including but not limited to: analgesics, anesthetics, antifungals, antibiotics, anti-inflammatories, nonsteroidal anti-inflammatory drugs (NSAIDs), anthelmintics, antidotes, antiemetics, antihistamines, anticancer drugs, antihypertensives, antimalarials, antimicrobials, antipsychotics, antipyretics, antiseptics, antiarthritics, antituberculotics, antitussives, antivirals, cardioactive drugs, cathartics, chemotherapeutic agents, a colored or fluorescent imaging agent, corticoids (such as steroids), antidepressants, depressants, diagnostic aids, diuretics, enzymes, expectorants, hormones, hypnotics, minerals, nutritional supplements, parasympathomimetics, potassium supplements, radiation sensitizers, a radioisotope, fluorescent nanoparticles such as nanodiamonds, sedatives, sulfonamides, stimulants, sympathomimetics, tranquilizers, urinary anti-infectives, vasoconstrictors, vasodilators, vitamins, xanthine derivatives, and the like.

Kits

The present invention also encompasses surgical kits for translocating a valve. The kits can include one or more translocation devices, wherein each device has the same size and thickness or a range of sizes and thicknesses to be selected by a surgeon to fit within a subject. The kits can further include one or more instruments relevant to the translocation procedure, including but not limited to: suture needles, suture thread, suture pledgets, forceps, scissors, scalpels, translocation device holders, and the like. In some embodiments, the kits can further include one or more tools to measure portions of a subject's heart and to select dimensions of a translocation device, such purpose-built sizers to measure a subject's native annulus and mitral valve circumference. In some embodiments, the kits can further include instructions for using a 3D echocardiogram to perform the measurements. For example, a 3D echocardiogram may be performed prior to an operation and a 3D analysis system may perform "in-silico" modeling to determine the optimal dimensions of a translocation device.

Figure 23:
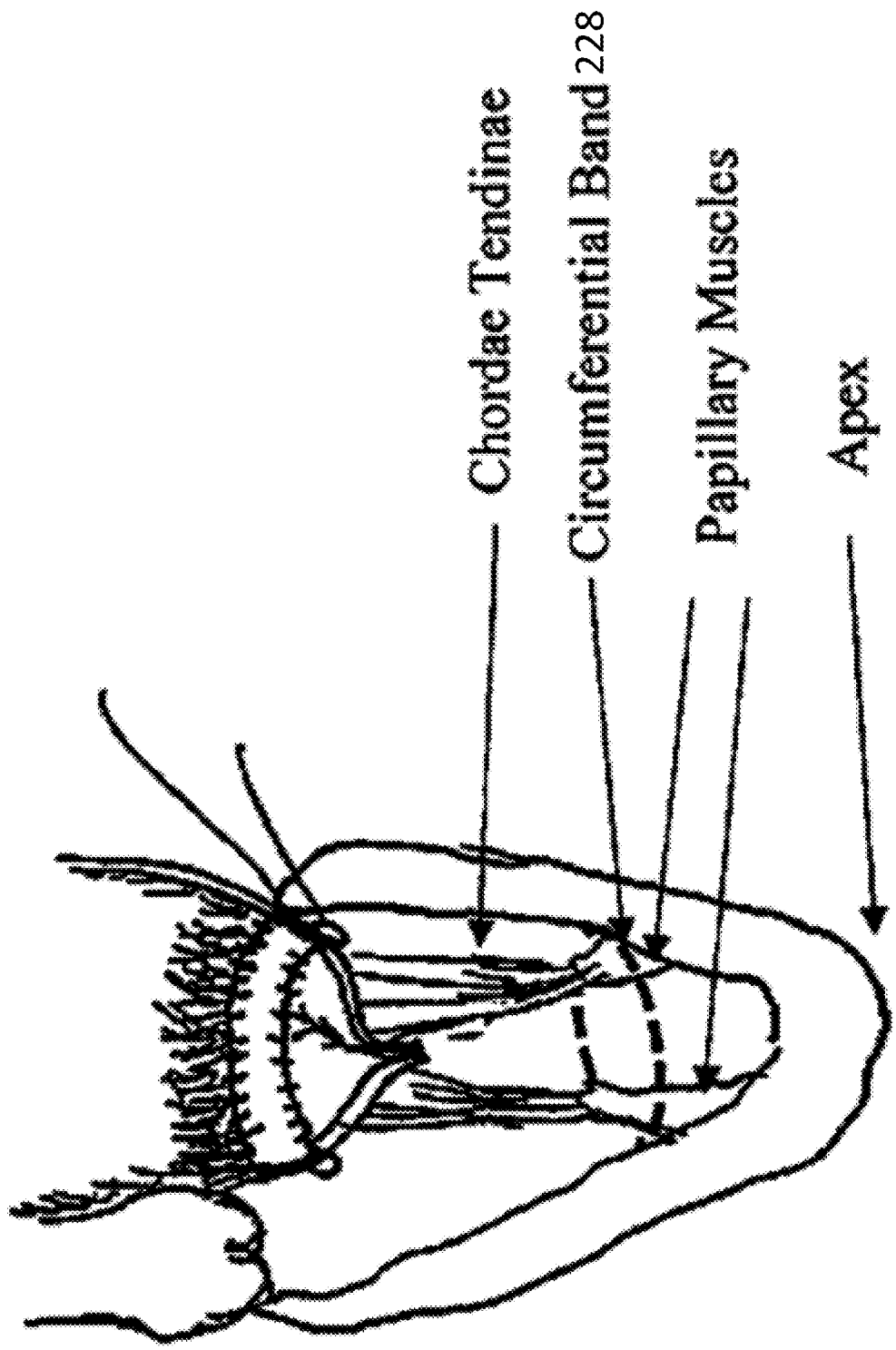
FIG. 23 depicts an exemplary implanted translocation collar device with the addition of a circumferential band around the chordae tendinae and papillary muscles.
Figure 24:
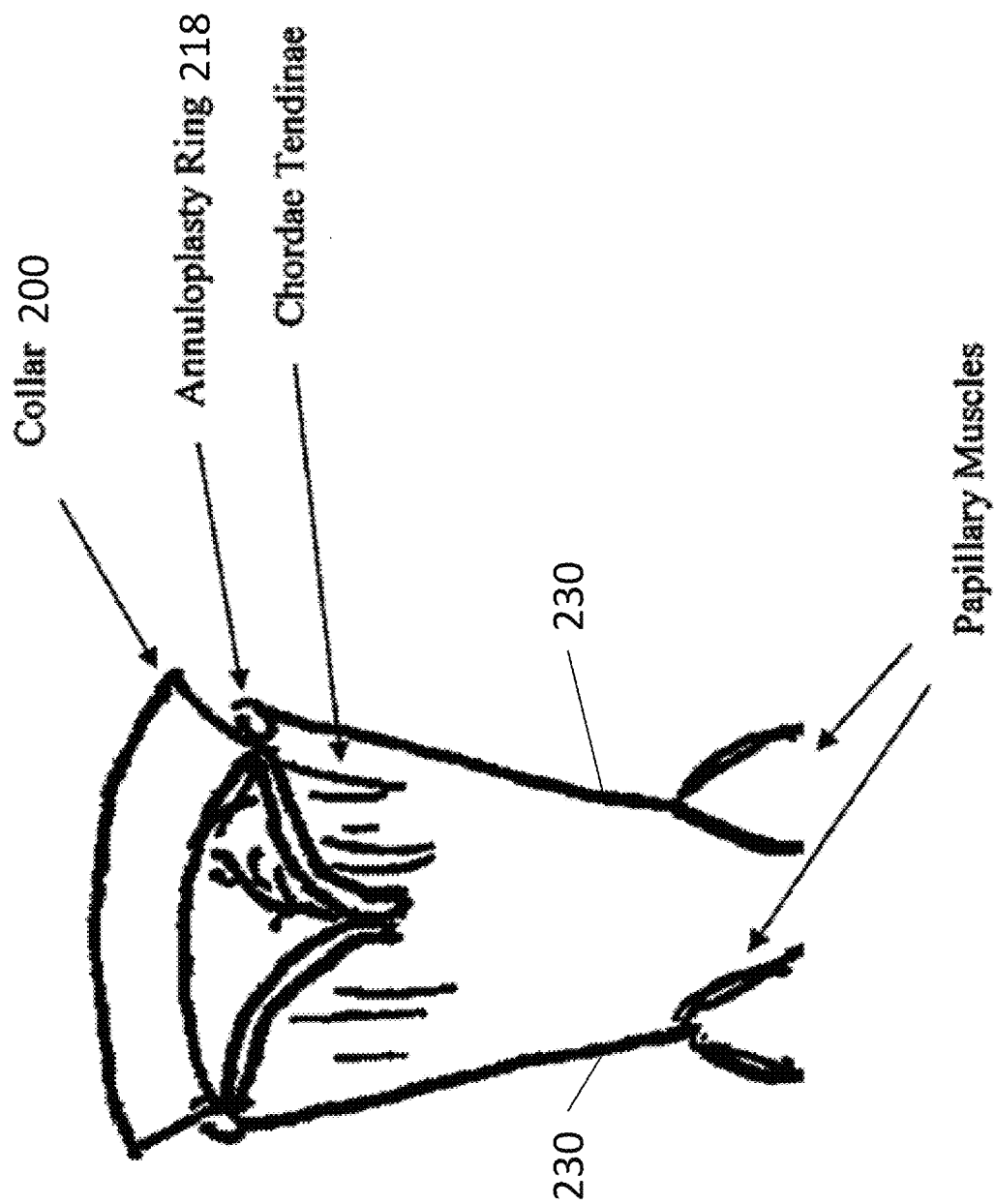
FIG. 24 depicts an exemplary implanted translocation collar device with the addition of supplementary tethers connected to the papillary muscles.

In some embodiments, the kit may also include other tools that further treat FMR. For example, the kit may include a circumferential band 228 configured to bring the papillary muscles closer together, such as by placing circumferential band 228 around the papillary muscles (FIG. 23). In another example, the kit may include one or more tethers or chords 230 configured to increase and maintain the apical length or displacement of an implanted device 200 (FIG. 24). Tethers or chords 230 can be attached to the papillary muscles at one end and to apical edge 214 of device 200 or to a large pledget secured to the epicardium of the heart. Tethers or chords 230 can be constructed from ePTFE sutures, such as sutures that are commonly used for repair of degenerative mitral regurgitation. In another example, the kit may include additional cuffs 26 attachable to device 200 and configured to further reduce the opening diameter of first edge 212 or second edge 214. Cuffs 26 each have a cuff aperture and an outer diameter that attaches, such as by suturing, to first edge 212 or second edge 214 of device 200, and the subject's anatomy can be sutured to the cuff aperture.

Methods of Valve Translocation

Figure 25:
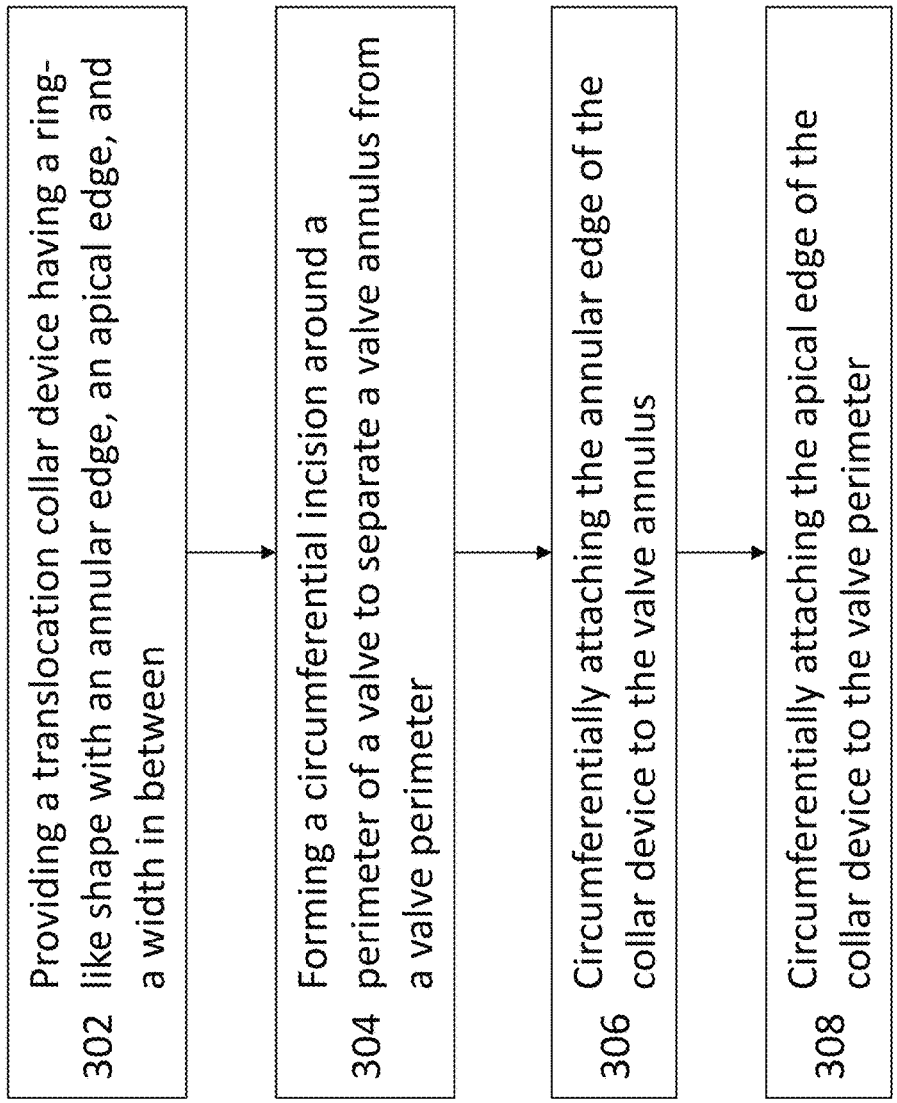
FIG. 25 is a flowchart depicting an exemplary method of implanting a translocation collar device.
Figure 26C:
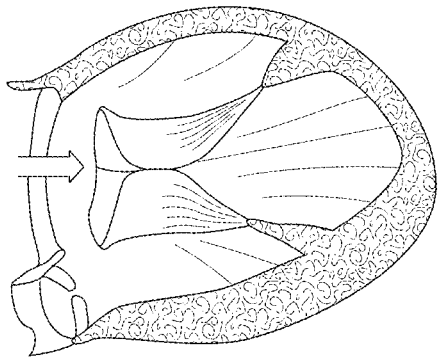
FIG. 26A through FIG. 26E illustrate the steps of implanting an exemplary translocation collar device around a mitral valve.
Figure 26B:
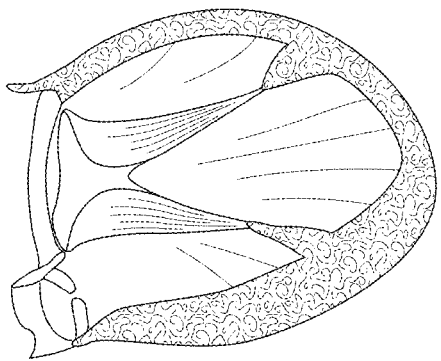
Figure 26A:
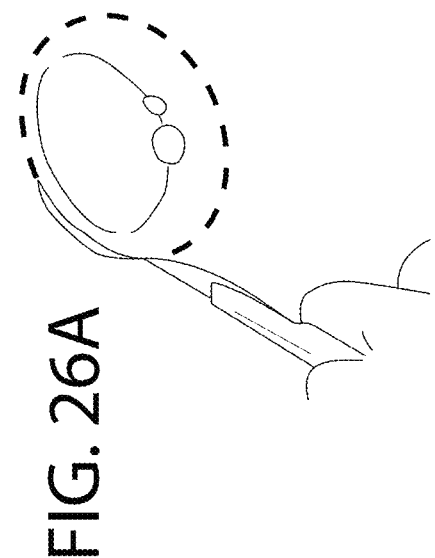
Figure 26E:
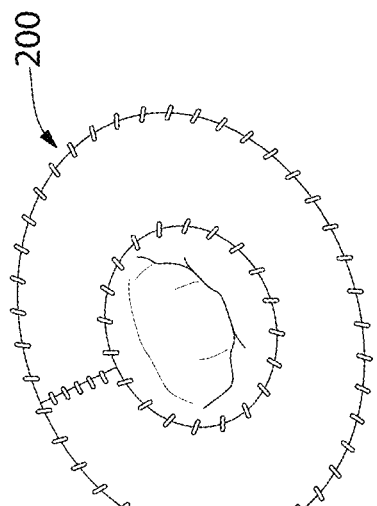
Figure 26D:
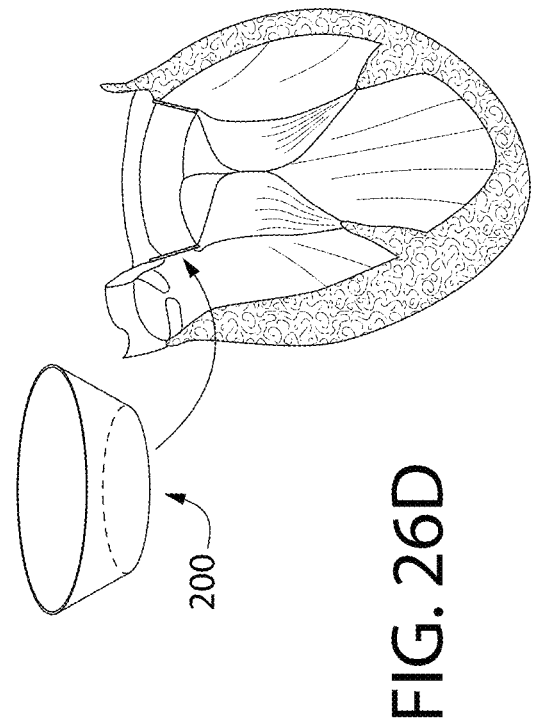

The present invention further includes methods of using the translocation collar devices of the present invention. Referring now to FIG. 25, an exemplary method 300 is depicted. Method 300 begins with step 302, wherein a translocation collar device of the present invention is provided, the collar device having a ring-like shape with an annular edge (e.g., annulus end), an apical edge (e.g., leaflet end), and a width (e.g., distance from annulus end to leaflet end) in between. In step 304, a circumferential incision is formed around a perimeter of a valve to separate a valve annulus from a valve perimeter. The incision keeps the structure of the original valve leaflets, commissures, and other physical features intact, including the chordae tendinae and associated muscles (FIG. 26A through FIG. 26C). In step 306, the annular edge of the collar device is circumferentially attached to the valve annulus. In step 308, the apical edge of the collar device is circumferentially attached to the valve perimeter (FIG. 26D, FIG. 26E). The attachment means can include sutures, adhesives, staples, and/or the like.

In some embodiments, a method for implanting the translocation collar device begins after sizing the device, as discussed herein. The method includes marking four regions (i.e., quadrants) of a patient's mitral valve annulus to prevent rotation of the valve leaflets relative to the annulus during the suturing process. The valve is separated from the annulus in the quadrants. For each quadrant, multiple (e.g., about three or more) horizontal mattress sutures are placed between the device and the annulus and additional (e.g., about three or more) horizontal mattress sutures are placed between the device and the valve leaflets. These sutures allow the device to be seated below the plane of the annulus and the leaflets. Each quadrant is sutured with a running suture, and the method is repeated for all four quadrants. In some embodiments, less or more than four regions can be used.

In some embodiments, the dimensions of the valve are sized before a translocation collar device is provided. In one embodiment, the dimensions are sized by measuring the native annulus after circumferential incision and detachment of the valve with a first set of sizers, and measuring the circumference of the valve perimeter with a second set of sizers. In some embodiments, the dimensions are sized by measuring the heart with a 3D echocardiogram and analyzing the measurement with a 3D analysis system.

In some embodiments, first edge 212 or second edge 214 is sized to a subject's annulus. The dimensions of the opposing edge can be determined in reference to the size of the subject's annulus. First edge 212 or second edge 214 can be reduced or "downsized," such as by one or more sizes. For example, the size can be reduced by 2 sizes (in which 1 size=5 mm circumference). For reference, a common size is 38 (orifice area of about 722 $mm^2$, circumference of about 95 mm). The smaller orifice would then be size 34 (apical opening area of about 572 $mm^2$, circumference of about 85 mm). These can be labeled as small, medium, large, and the like, in which a surgeon uses sizers to determine whether the annulus of a patient is small, medium, large, and the like. Each size can be based on the sizer, and the opposing edge can be downsized by the circumference, such as by 10 mm.

In some embodiments, the valve annulus and valve perimeter are fully separated prior to attaching the collar device. In some embodiments, the valve annulus and valve perimeter are partially separated, and the collar device is attached as the circumferential incision is made in a stepwise sequence. A stepwise sequence can be advantageous in that the valve annulus and valve perimeter are always attached together, either by natural tissue or by the collar device, improving valve stability throughout the operation. In some embodiments, a portion less than the entirety of the valve annulus/perimeter can be separated, and a semi-annular collar device can be attached to the portion (e.g., a subset of native leaflets can be removed, while one or more native leaflets remain attached to the native annulus.

Figure 27:
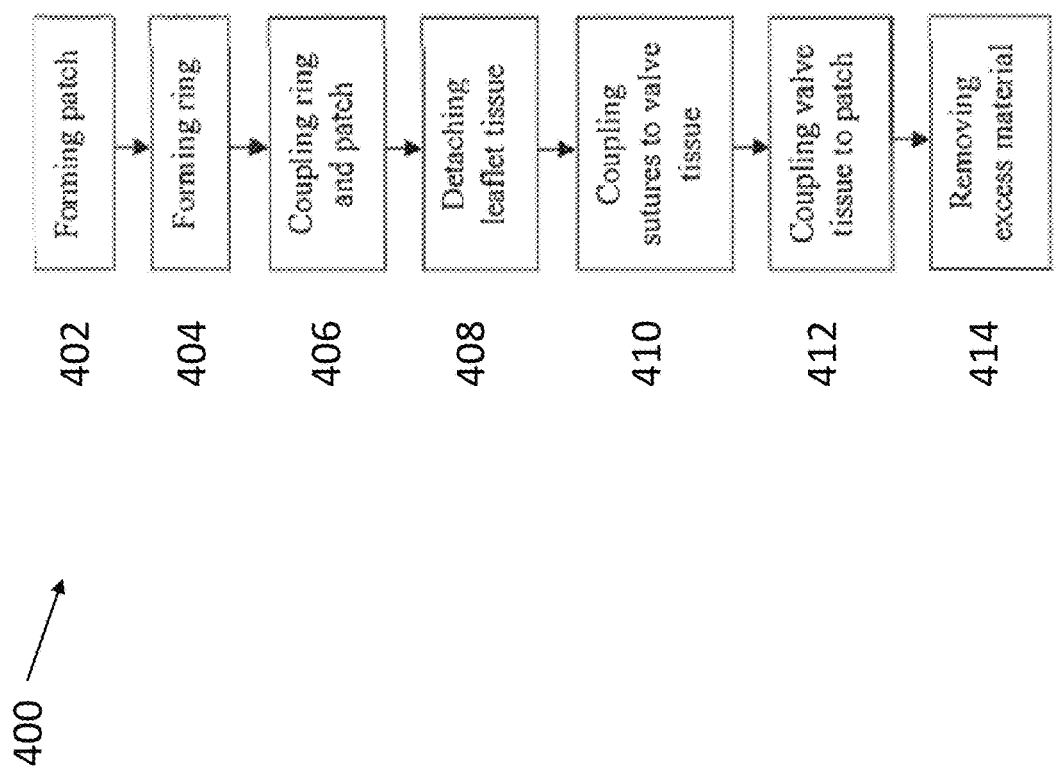
FIG. 27 is a flowchart depicting an exemplary method configured to facilitate durable mitral valve repair.
Figure 28:
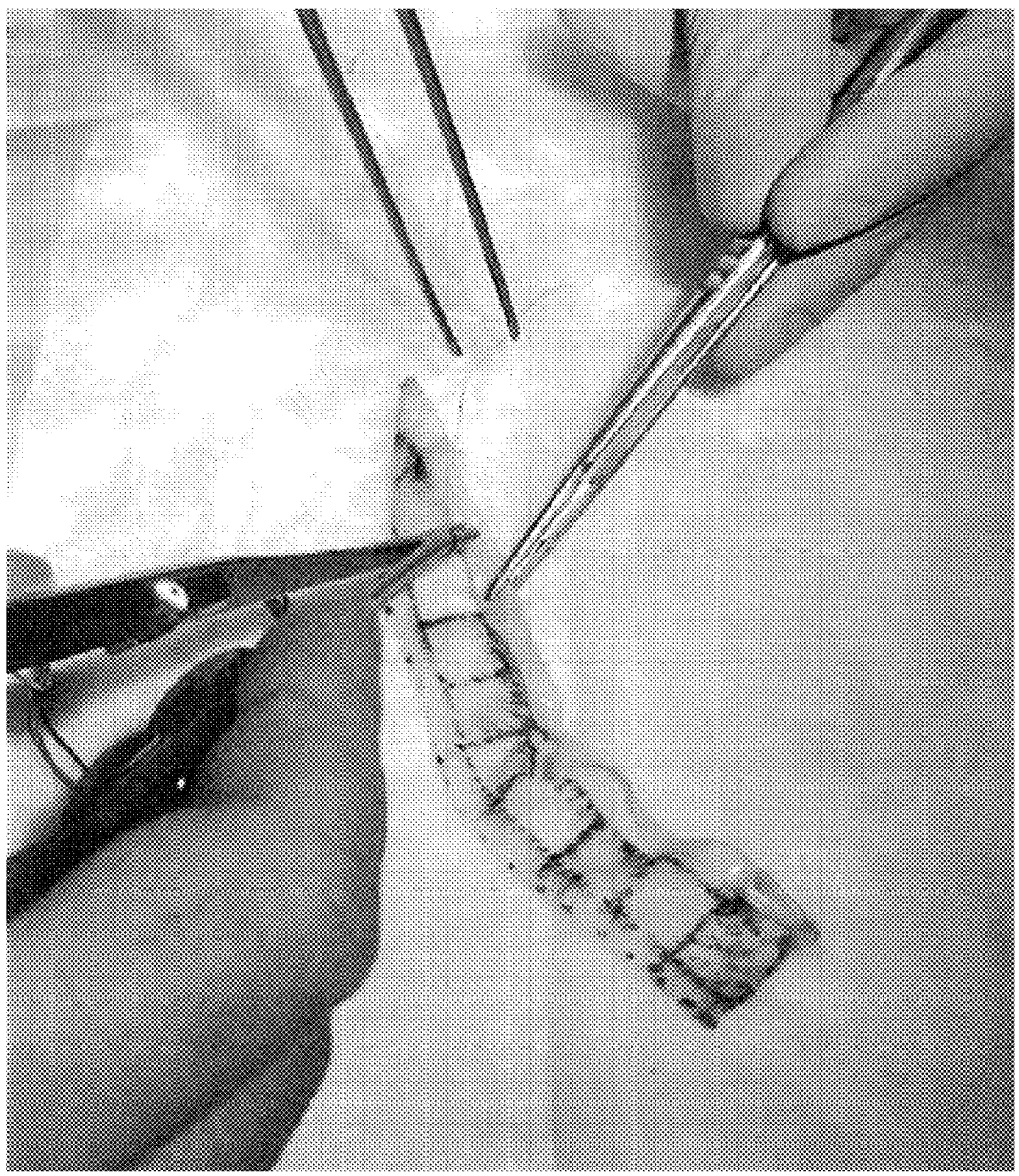
FIG. 28 is a photograph depicting the formation of a translocation collar patch.
Figure 29:
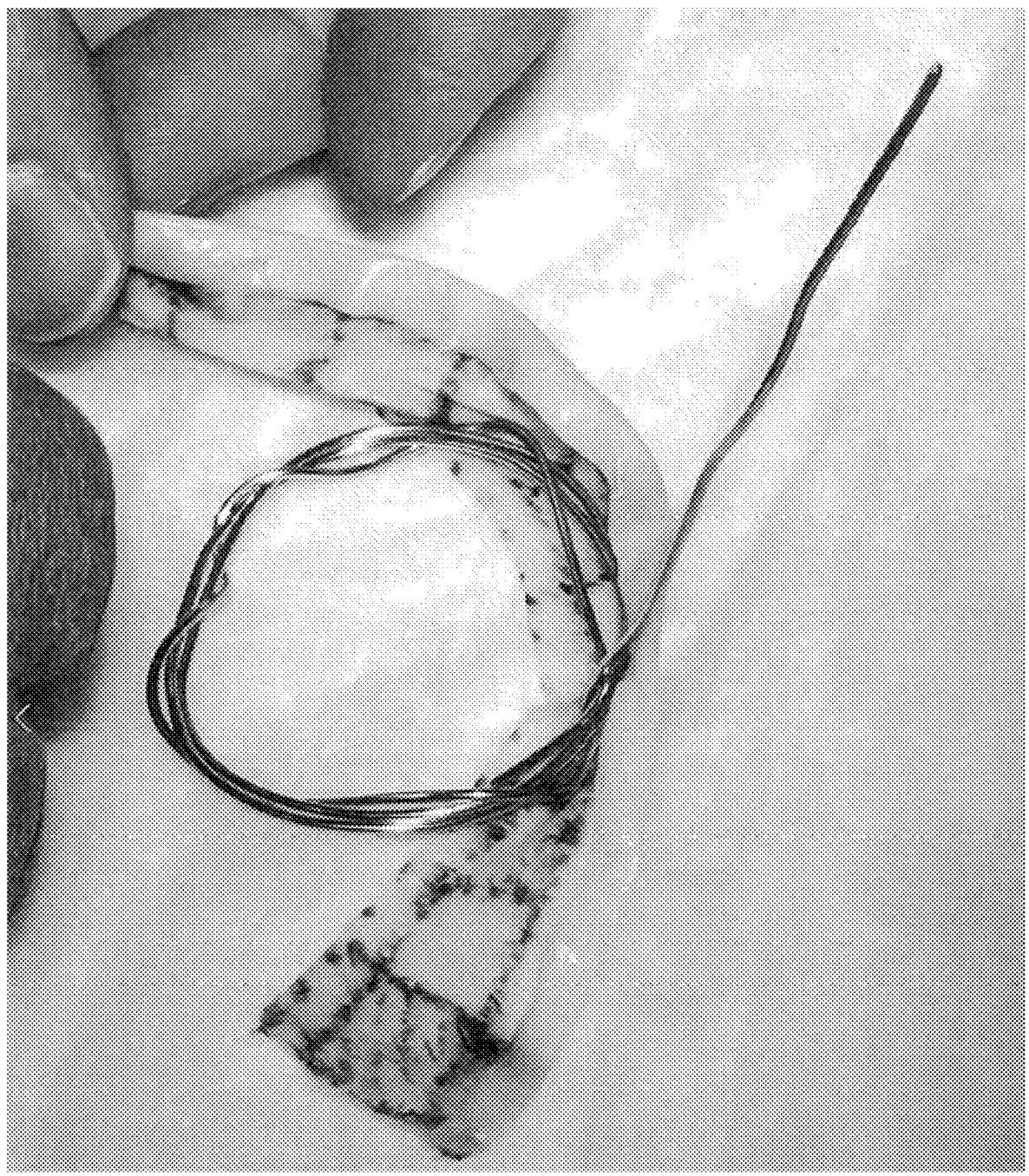
FIG. 29 is a photograph depicting the formation of a ring configured to stiffen the translocation collar patch.

Referring now to FIG. 27 and depicted in FIG. 28 through FIG. 38, another exemplary method 400 is shown, wherein method 400 is configured to facilitate durable mitral valve repair for many patients and physicians. The method includes step 402 of forming a patch (implant, as described above; see FIG. 28). In some implementations, step 402 further includes marking regions (e.g., quadrants) and forming an outer ring portion (e.g., folding the patch). The method can further include step 404 of forming a ring configured to stiffen the patch (FIG. 29). The ring can be elliptical, circular-like, or have other shapes intended to adapt the patch to a shape of the mitral valve. The ring can have various stiffnesses depending on the materials (e.g., of the patch and sutures) and size and condition of the patient, etc. Furthermore, the ring can include an extension leg configured to ease handling and maneuvering of the ring, such as when performing the method. The extension leg can be integrally formed to the ring or configured to couple to the ring.

Figure 30A:
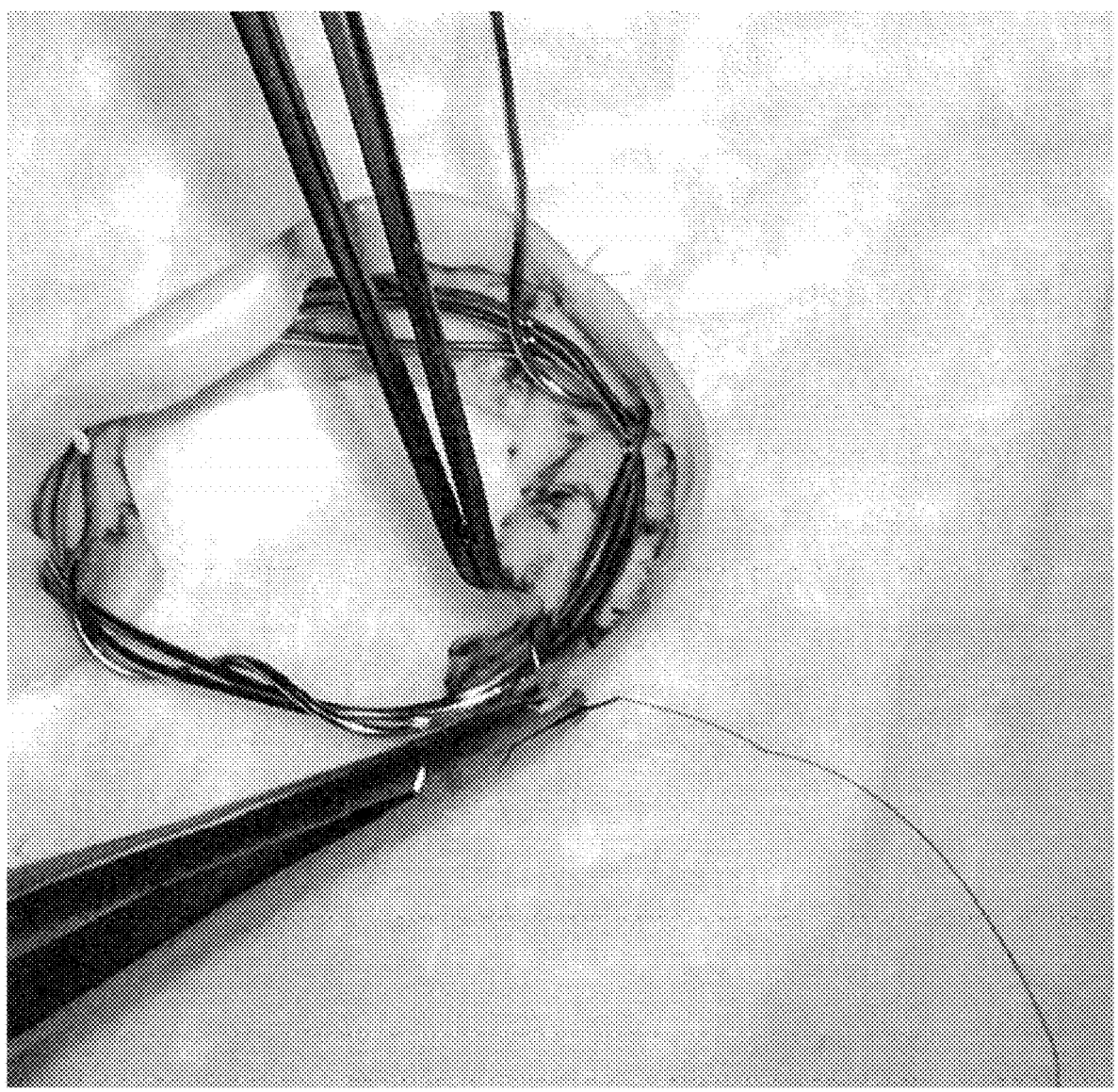
FIG. 30A and FIG. 30B are photographs depicting the coupling of the ring to the translocation collar patch.
Figure 30B:
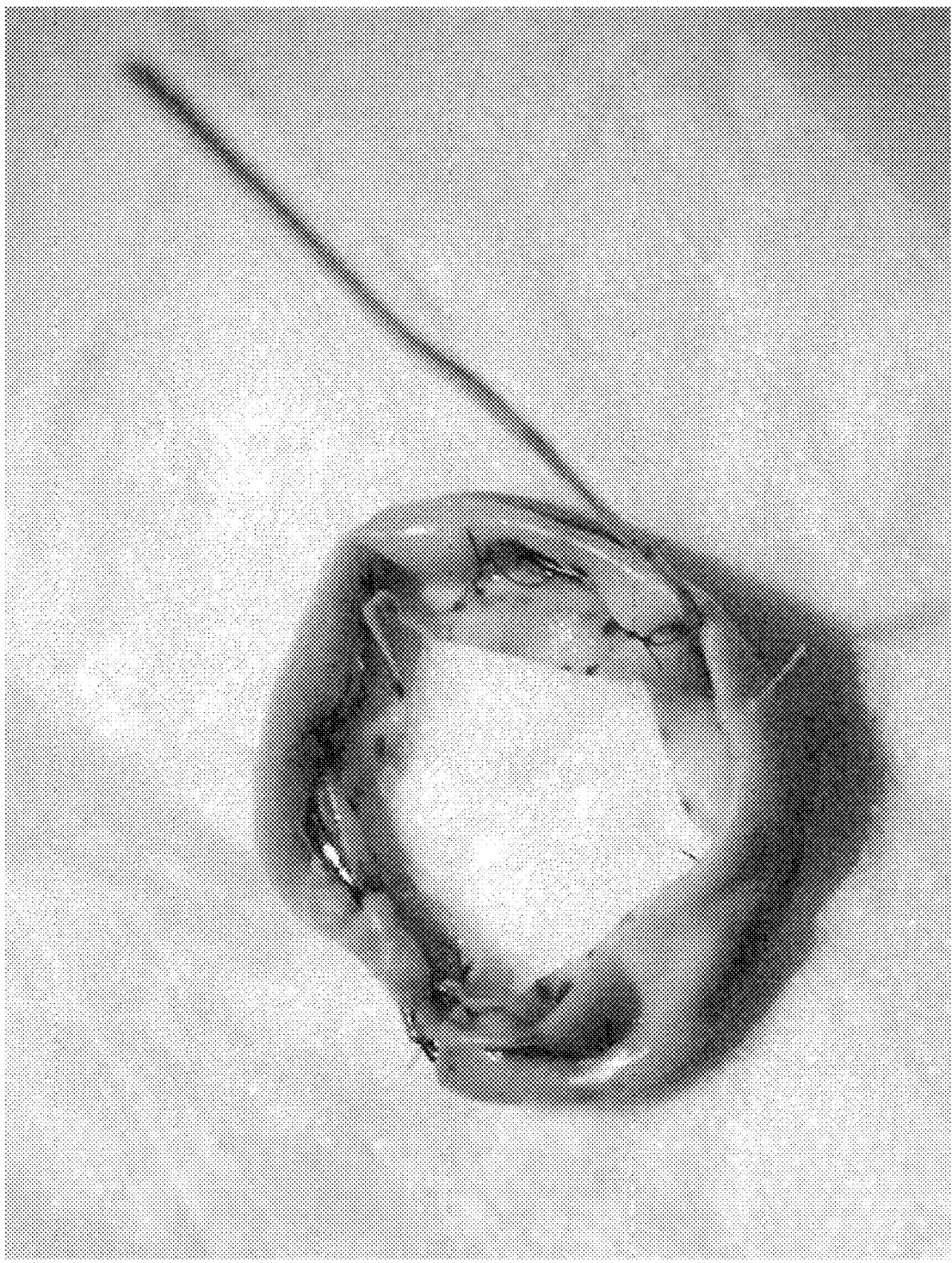

The method further includes step 406 of coupling the ring and the patch (FIG. 30A and FIG. 30B). In some embodiments, this includes inserting the ring and the outer ring portion of the patch. For example, coupling the ring can substantially enclose the ring within an outer portion of the patch. In some embodiments, at least one of the patch and/or ring can include markings to orient and align the patch and/or ring. In some embodiments, the method includes securing the ring within the outer portion of the patch with sutures (which may be permanent or temporary), such as by closing ends of the outer portion.

Figure 31A:
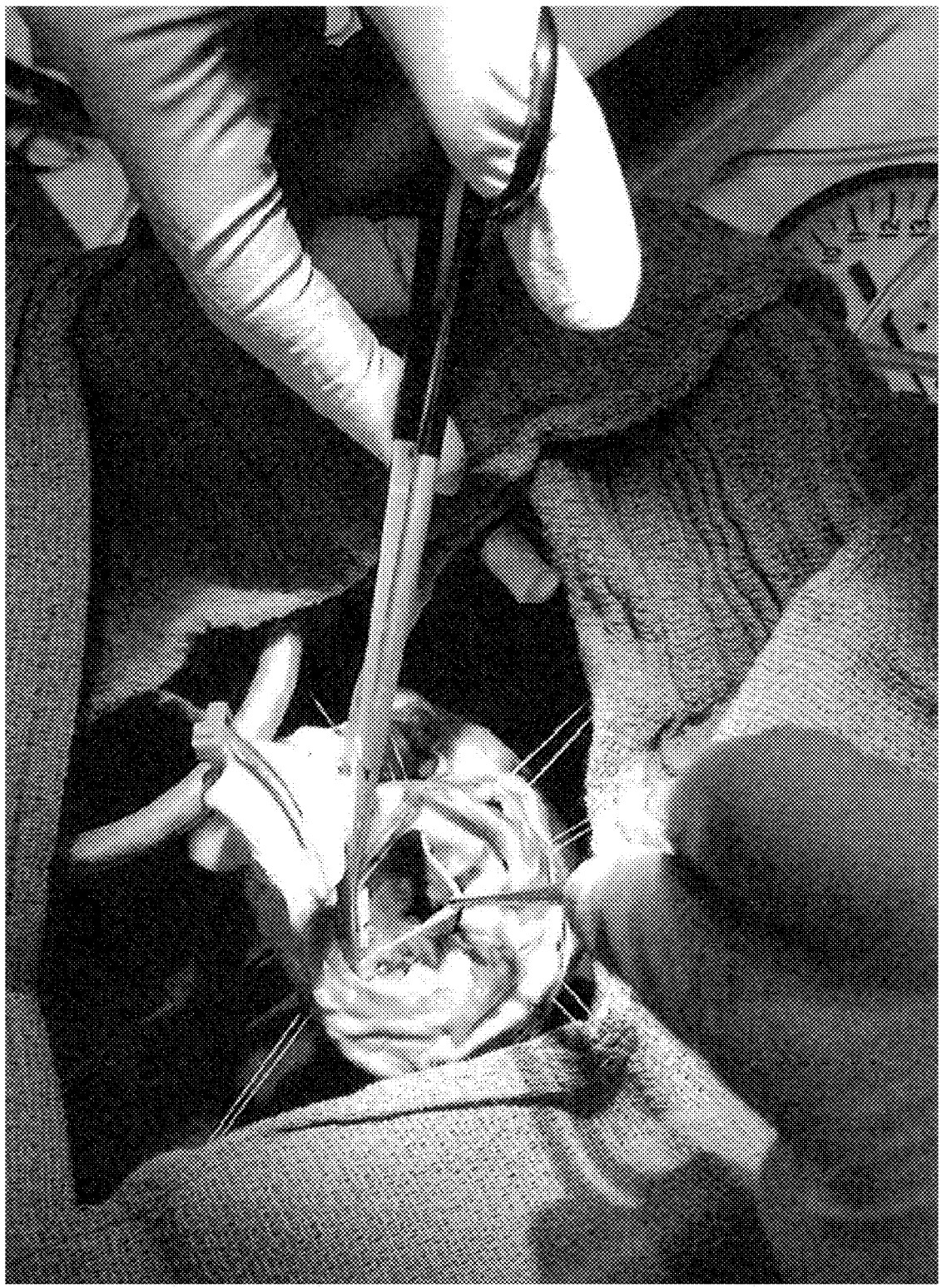
FIG. 31A and FIG. 31B are photographs depicting detaching leaflet tissue from valve tissue within the heart (e.g., using typical methods) prior to attaching a first end of sutures to the valve tissue.
Figure 31B:
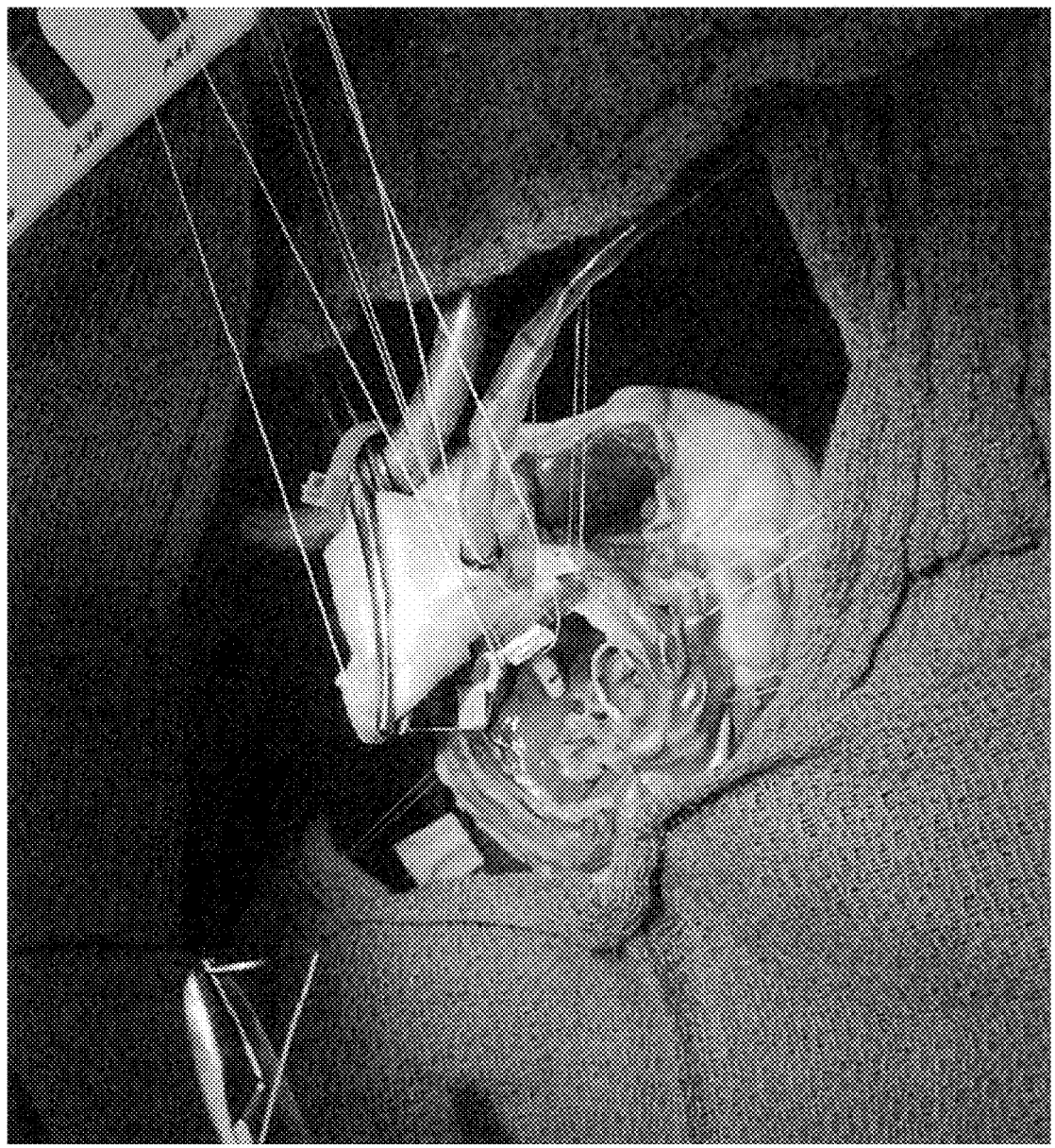
Figure 32:
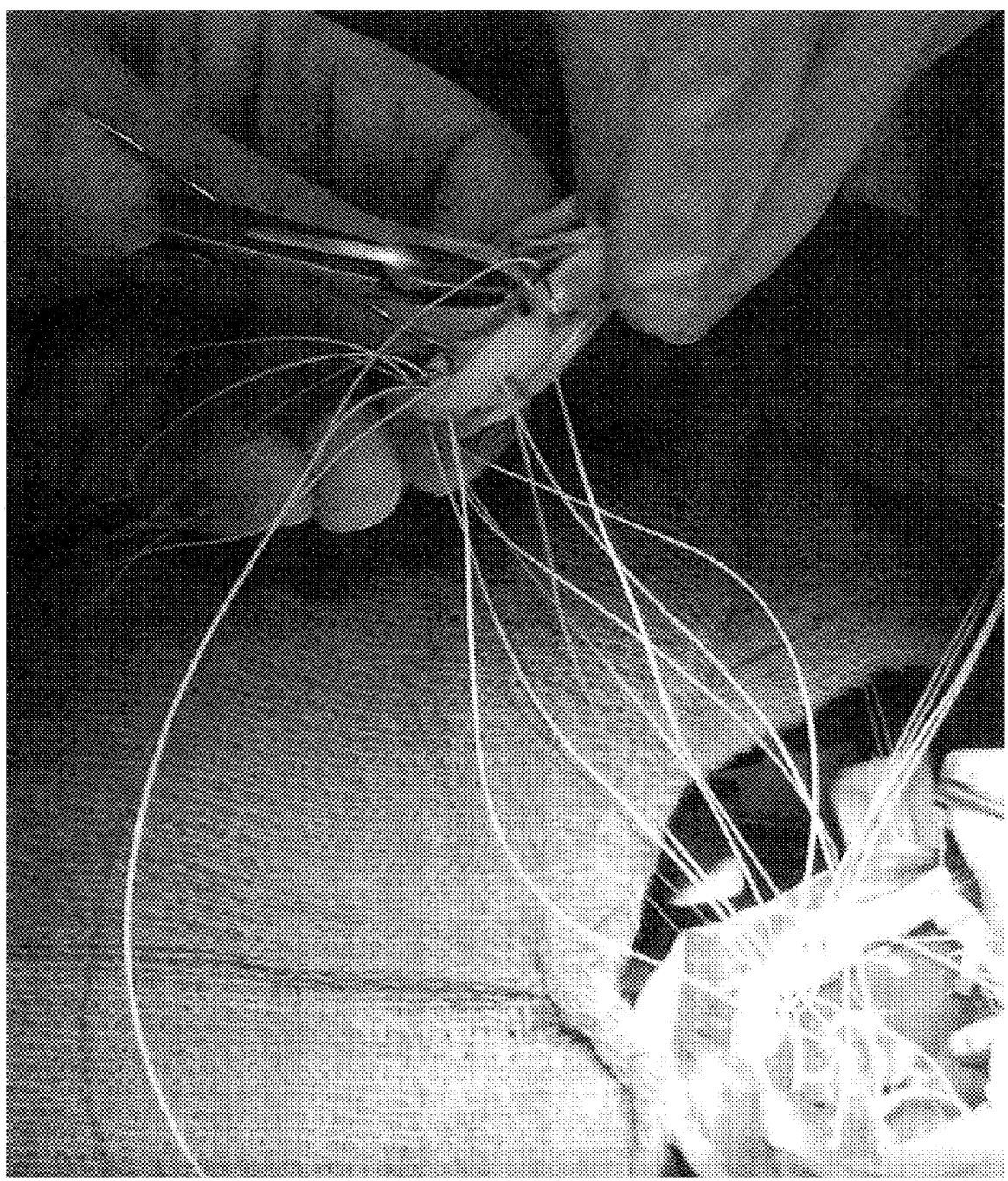
FIG. 32 is a photograph depicting coupling sutures to the patch by passing a second end of the sutures through an inner portion of the patch.
Figure 33A:
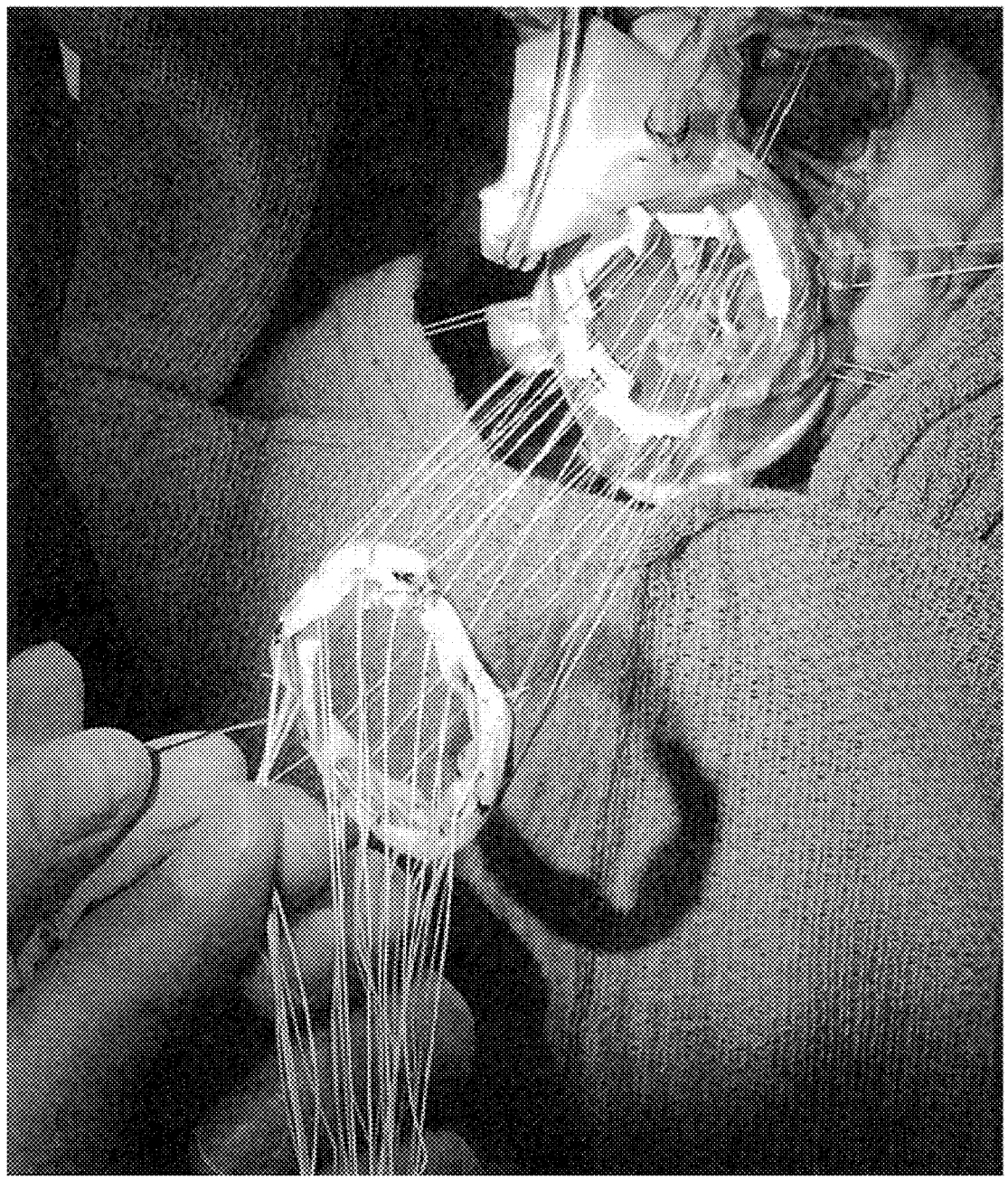
FIG. 33A and FIG. 33B are photographs depicting sliding the patch along the sutures to be adjacent to the first end of the sutures.
Figure 33B:
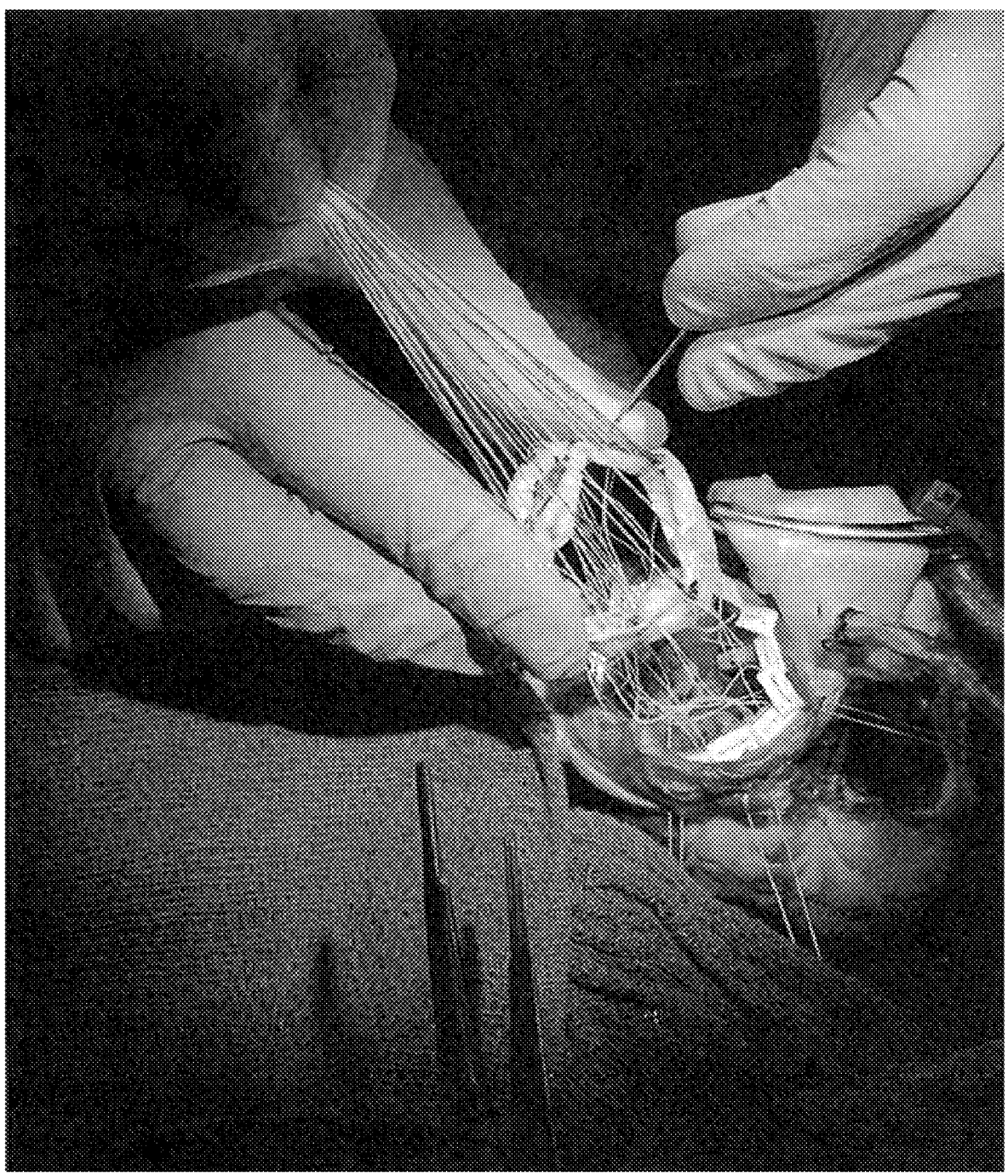
Figure 34:
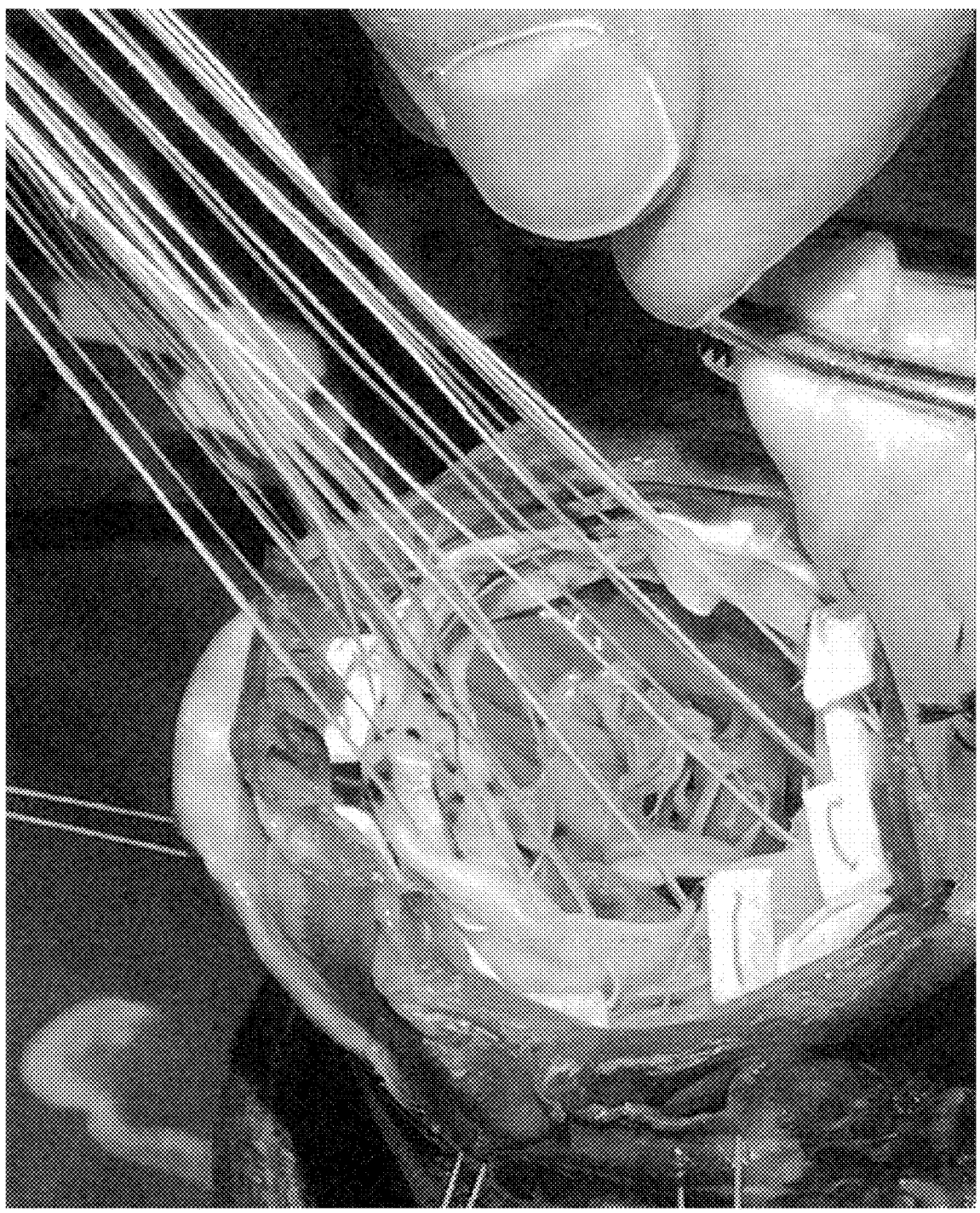
FIG. 34 through FIG. 38 are photographs depicting securing the patch to the valve tissue.
Figure 35:
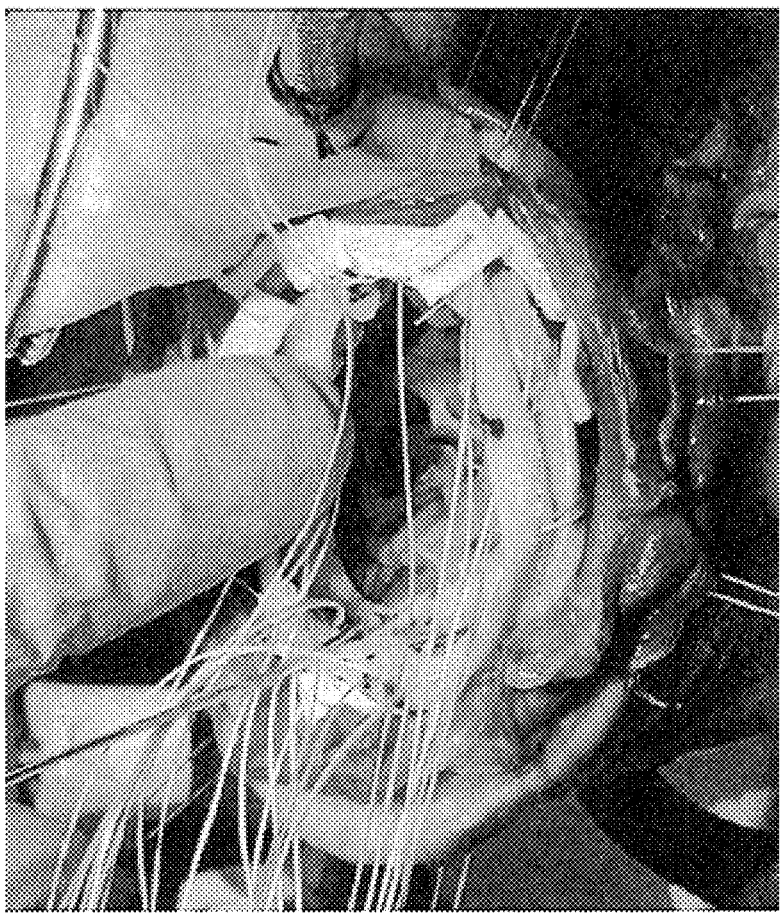
Figure 36:
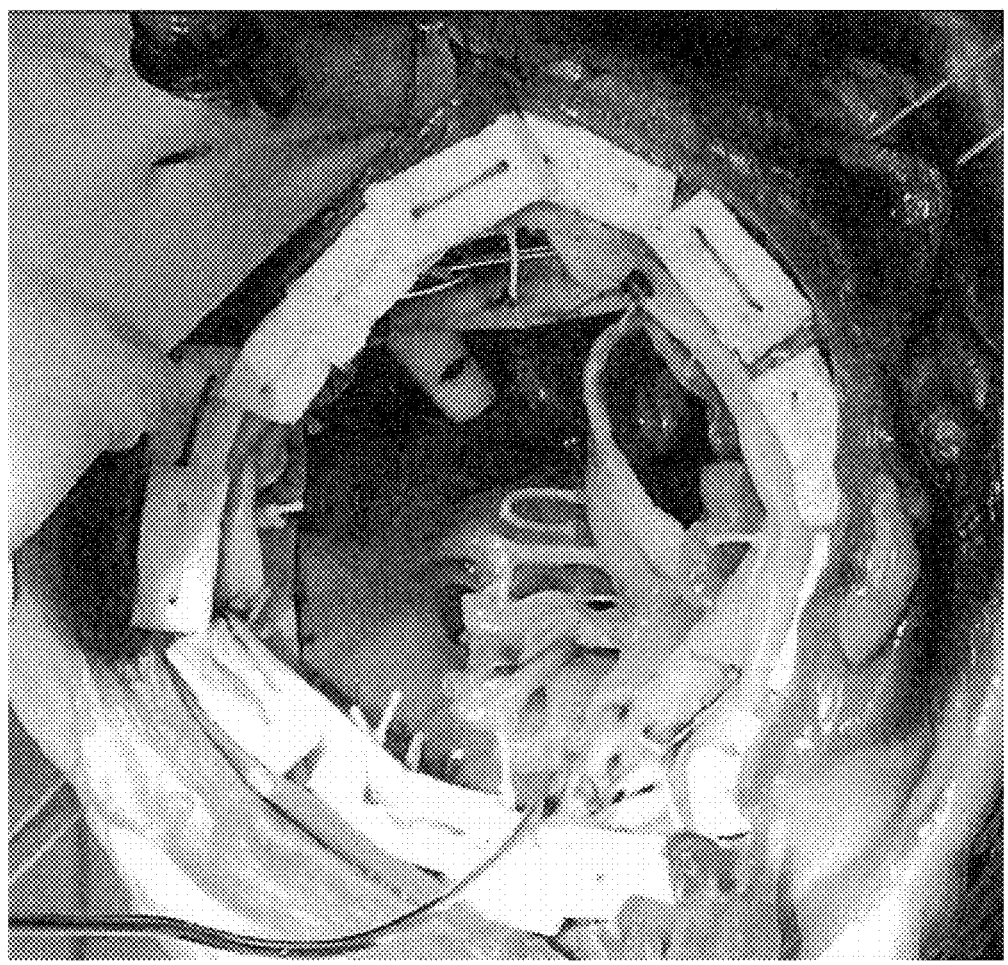
Figure 37:
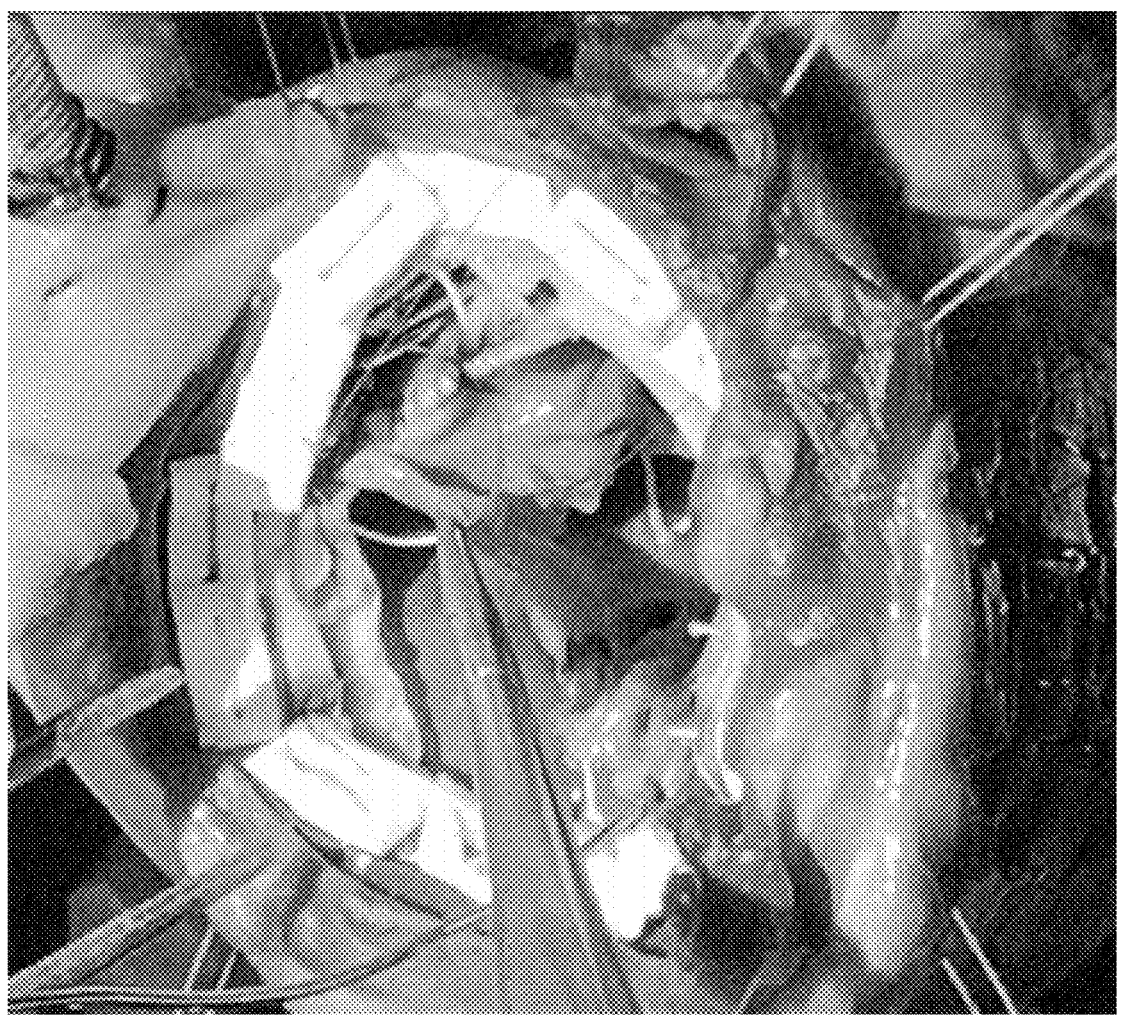
Figure 38:
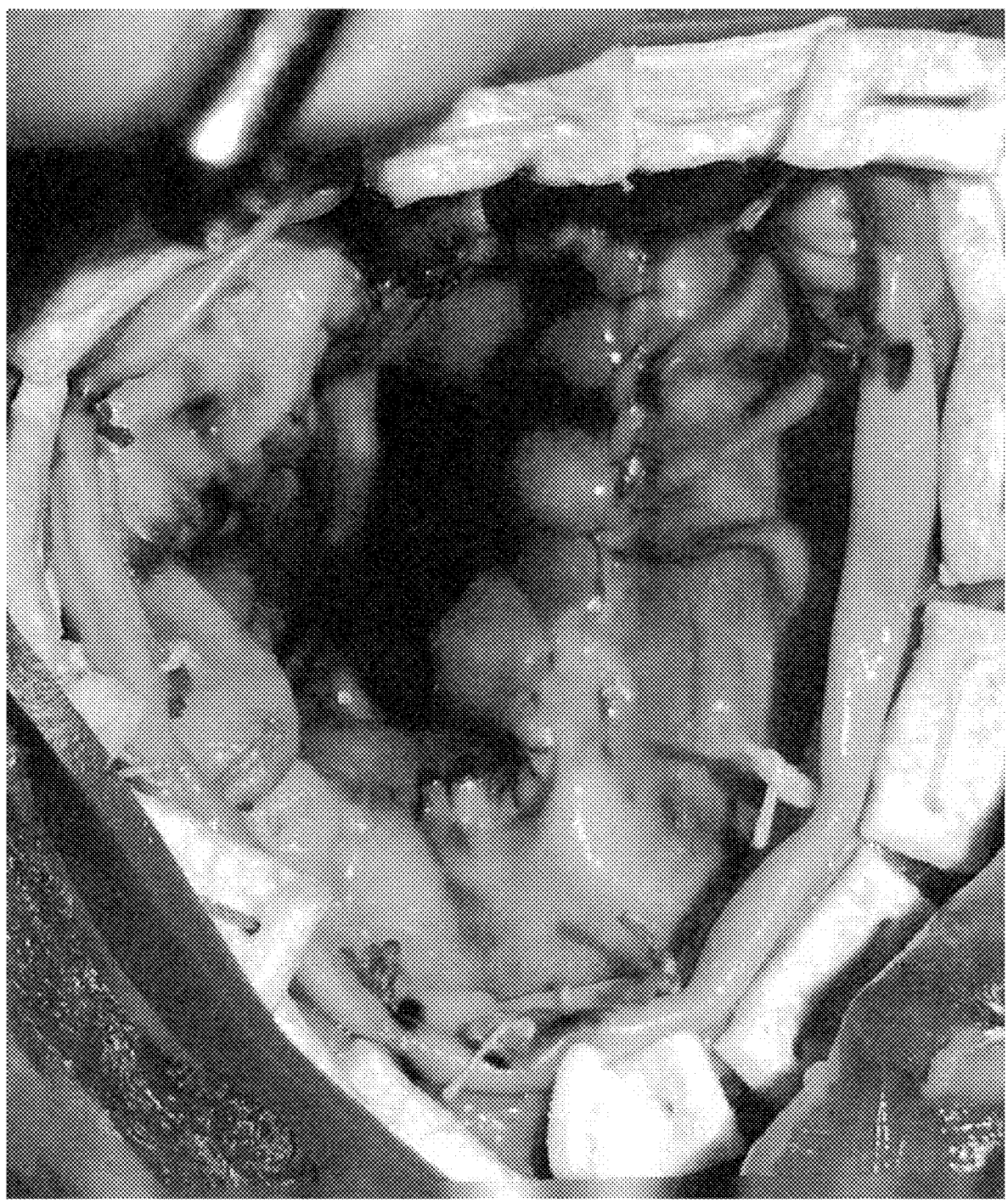

In some embodiments, the method further includes step 408 of detaching leaflet tissue from valve tissue within the heart (e.g., using typical methods) prior to attaching a first end of sutures to the valve tissue (FIG. 31A and FIG. 31B). Furthermore, the method can include step 410 of coupling sutures to the patch (FIG. 32), such as by passing a second end of the sutures through an inner portion of the patch. The patch can be further positioned adjacent to the valve tissue and tightening the sutures (i.e., removing slack in the sutures). For example, positioning the patch adjacent to the valve tissue can include sliding the patch along the sutures to be adjacent to the first end of the sutures (FIG. 33A, FIG. 33B). In some embodiments, the method further includes securing the patch to the valve tissue (FIG. 34 through FIG. 38). For example, the securing of the patch can include tying-off the sutures and removing excess suture material (FIG. 36).

The method can further include step 412 of coupling valve tissue to the patch and/or leaflet tissue to the inner portion of the patch. For example, coupling the leaflet tissue can include placing sutures between the leaflet tissue and the inner portion. Furthermore, in some embodiments the method can further include step 414 of removing excess material, such as the ring (e.g., such as by the extension leg). In some embodiments, only the extension leg is removed. In some embodiments, any temporary sutures are removed.

In some embodiments, the methods of the present invention are performed percutaneously. The collar device can be introduced near the valve site, such as in a ventricle or atrium, using a transapical technique, a transfemoral technique, a transaortic technique, a transseptal technique, and the like to implant the collar device in a circumferential fashion around a subject's normal valve annulus.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out exemplary embodiments of the present invention, and are not to be construed as limiting in any way the remainder of the disclosure.

Example 1: In Vivo Swine Analysis

Figure 39:
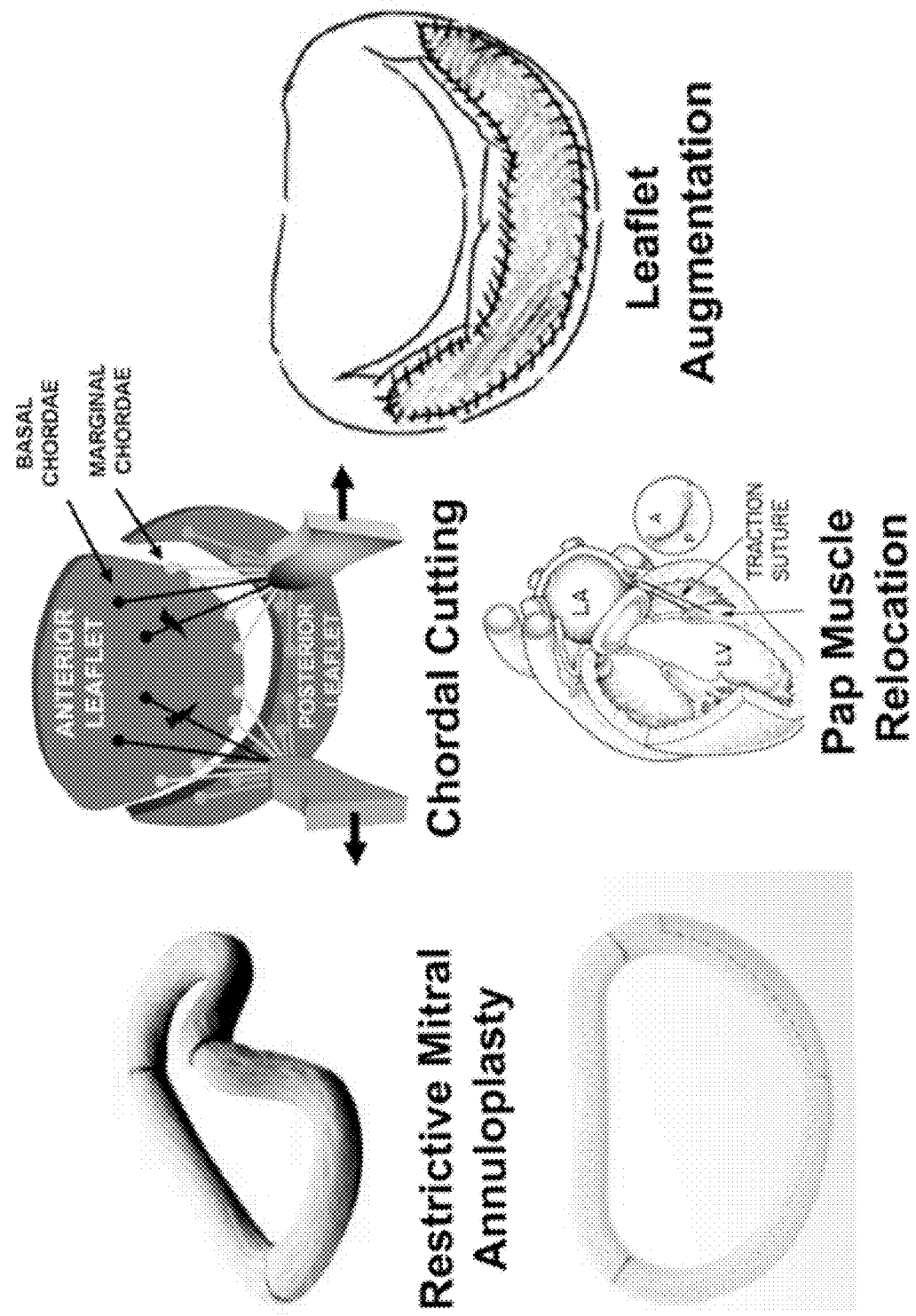
FIG. 39 depicts common surgical approaches to treat functional mitral regurgitation, each with its own drawbacks.

There is no reliable and durable mitral valve repair option for patients with functional mitral regurgitation (FMR). Existing devices (tissue or mechanical) and methods are not durable, suffer high recurrence rates, and are limited by increased risk of bleeding, prosthetic valve dysfunction, infection, and thromboembolism (FIG. 39). The present study aims to improve upon valve repair by examining the efficacy of valve translocation collars.

Yorkshire swine (50-70 kg) were placed on cardiopulmonary bypass for translocation patch repair (n=7). Inner patch diameter was sized to anterior mitral valve leaflet. Leaflet was detached from the annulus and the bovine pericardial patch was sewn in. Pre- and post-operative echocardiography were used to evaluate efficacy of patch (FIG. 40A).

Figure 40B:
FIG. 40A and FIG. 40B depict the implantation of an exemplary translocation collar device into an excised porcine heart. The collar is sewn circumferentially to the mitral valve (i.e., first/distal suture line). After the distal suture line is complete, a standard mitral annuloplasty ring is placed around the collar at the level of the suture line, it is next sewn in place. The annuloplasty ring serves to stabilize and fix the perimeter of the mitral valve in an optimal configuration. In the final result, the collar is in place and the mitral valve is translocated toward the ventricle.
Figure 40A:
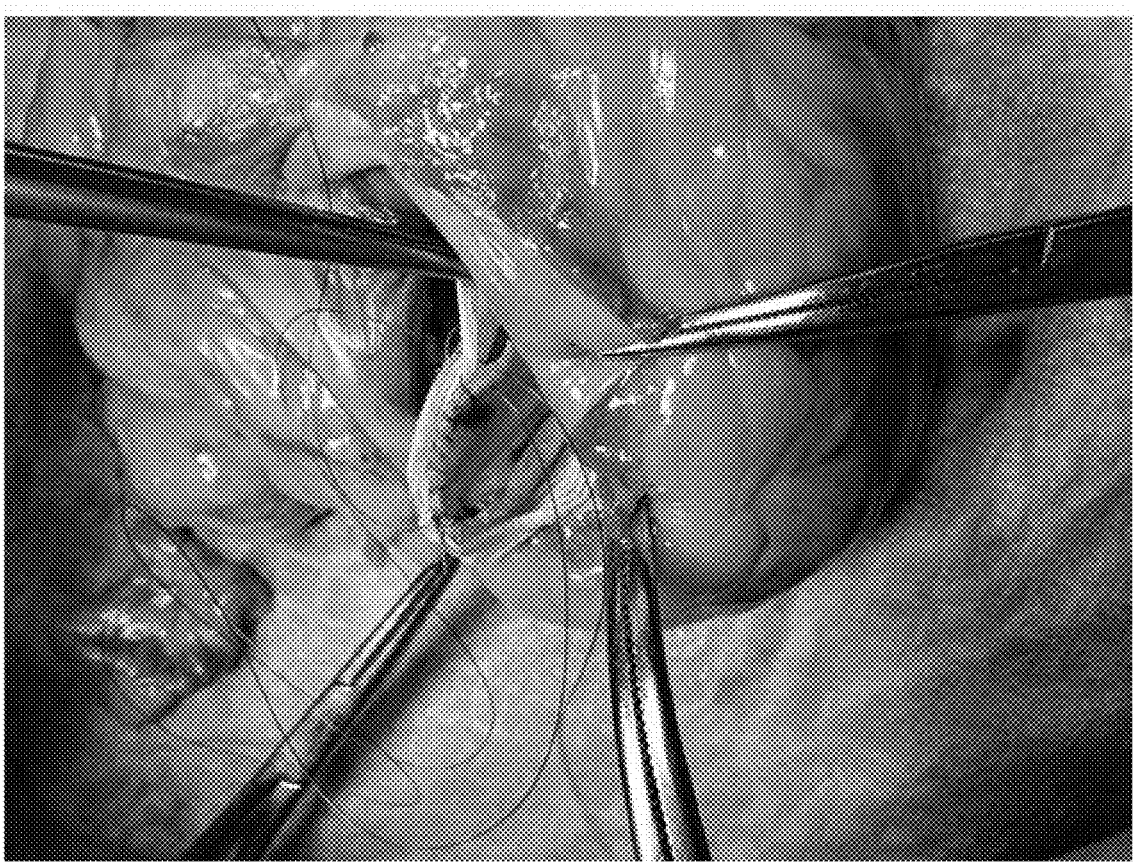
Figure 41:
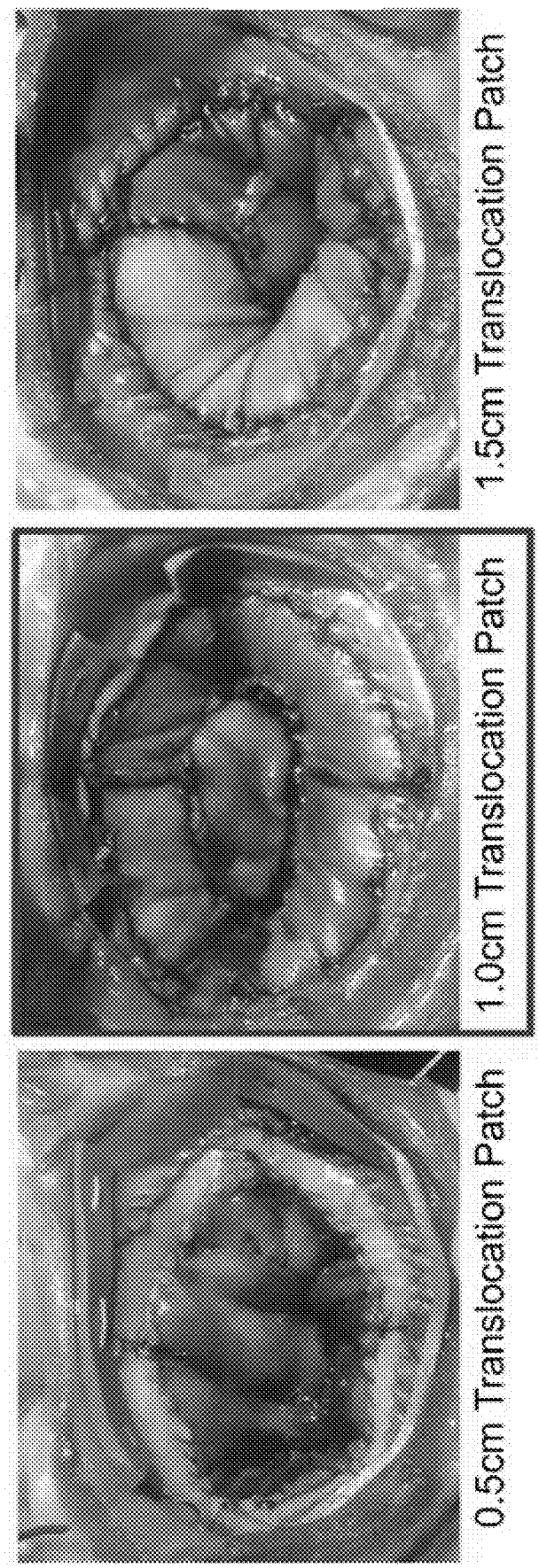
FIG. 41 depicts three prototype translocation collar devices having varying widths.
Figure 43A:
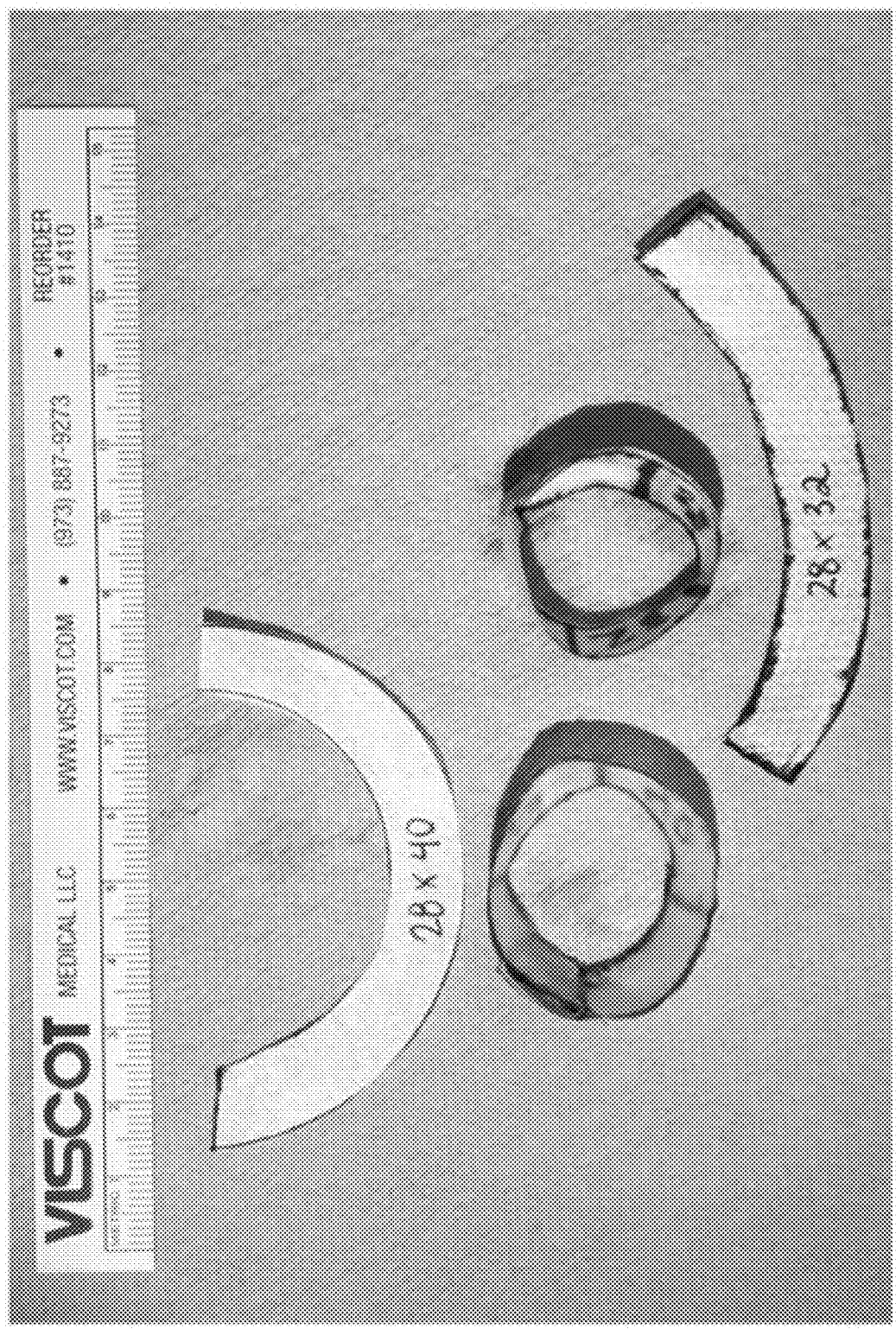
FIG. 43A and FIG. 43B depict a modified fabrication process to create a prototype translocation collar device having a steeper angle and sized to the dimensions of a recipient's annulus.
Figure 43B:
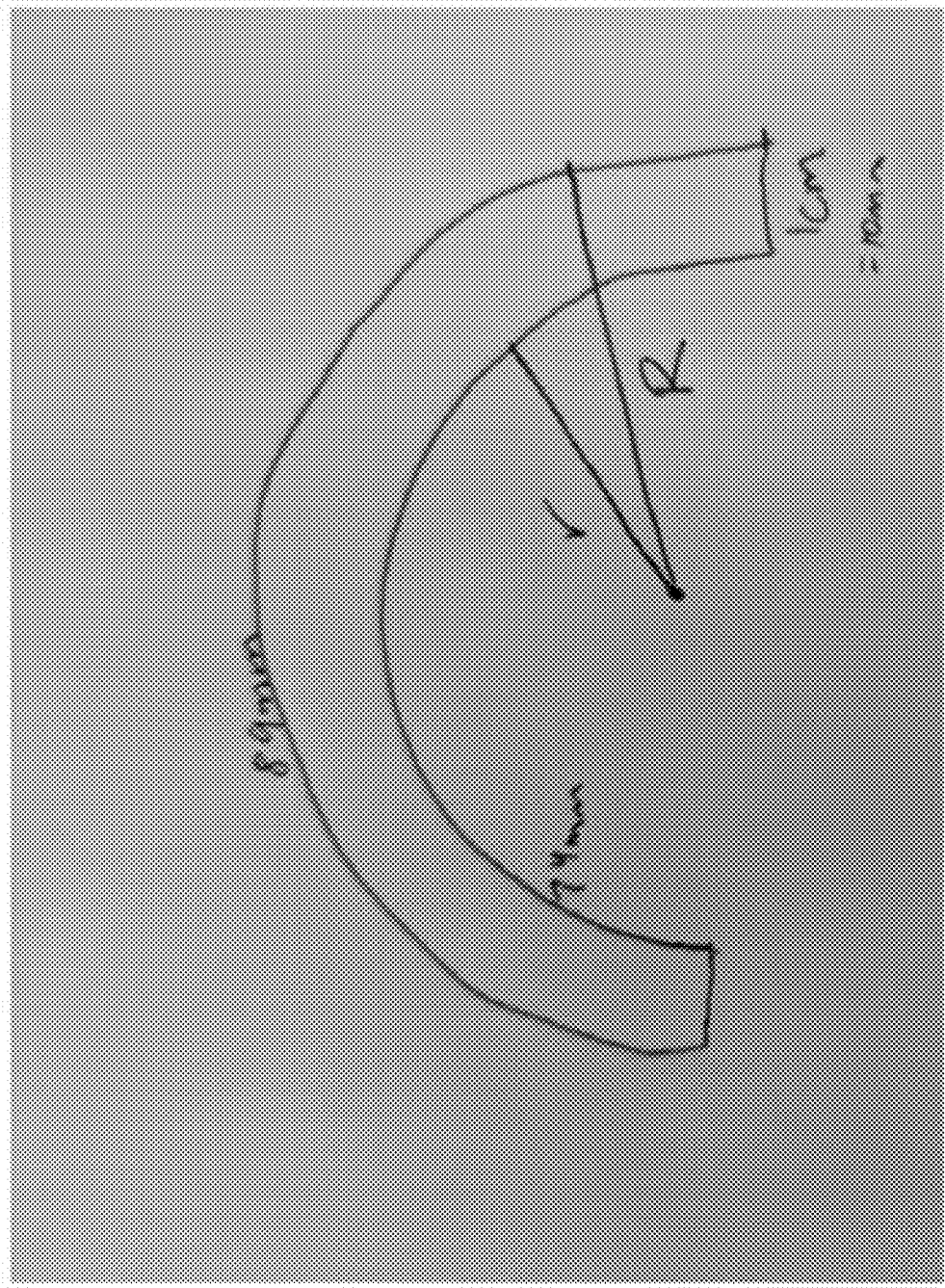
Figure 44B:
FIG. 44A and FIG. 44B depict an implanted translocation collar device having an upper diameter of 40 mm and a lower diameter of 28 mm.
Figure 44A:
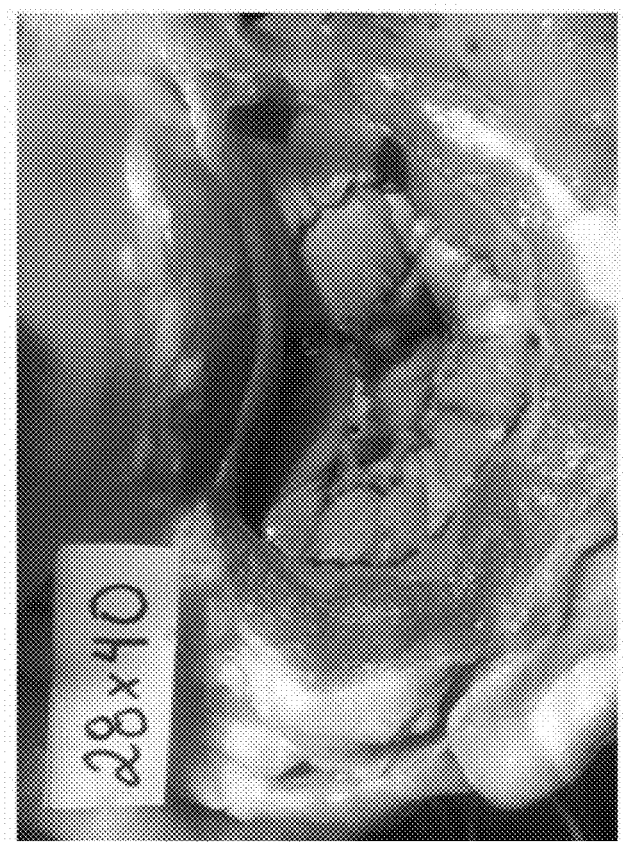

The collar implants improved coaptation from 0-4 mm to 6-10 mm (FIG. 40B). Other areas of improvement include: improved predictors of repair durability; tenting area reduced; leaflet angles improved. Mild suture line regurgitation was observed in 3/7 swine. Mitral valve area after repair was about 2.3 cm$^2$ (normally 5 cm$^2$).

Figure 45B:
FIG. 45A and FIG. 45B depict an implanted translocation collar device having an upper diameter of 32 mm and a lower diameter of 28 mm.
Figure 45A:
Figure 46B:
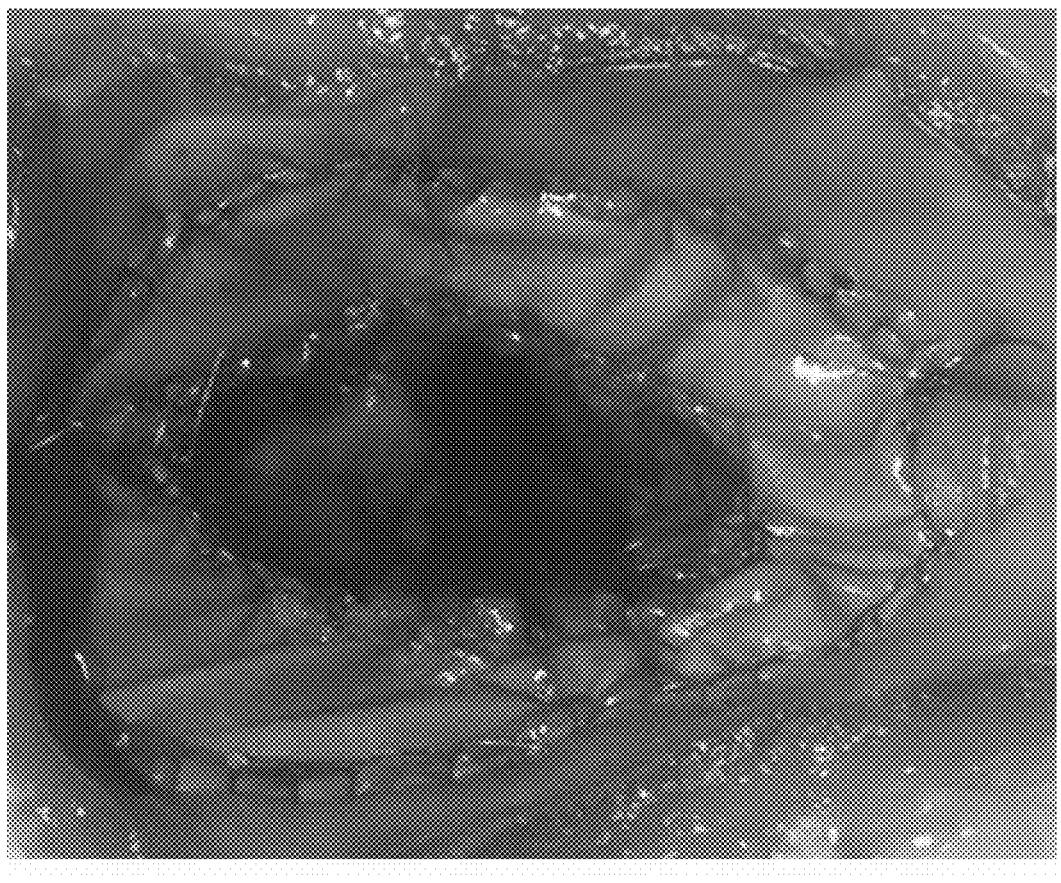
FIG. 46A and FIG. 46B depict the use of non-locking sutures (FIG. 46A) and the use of locking sutures (FIG. 46B) to prevent crimping.
Figure 46A:
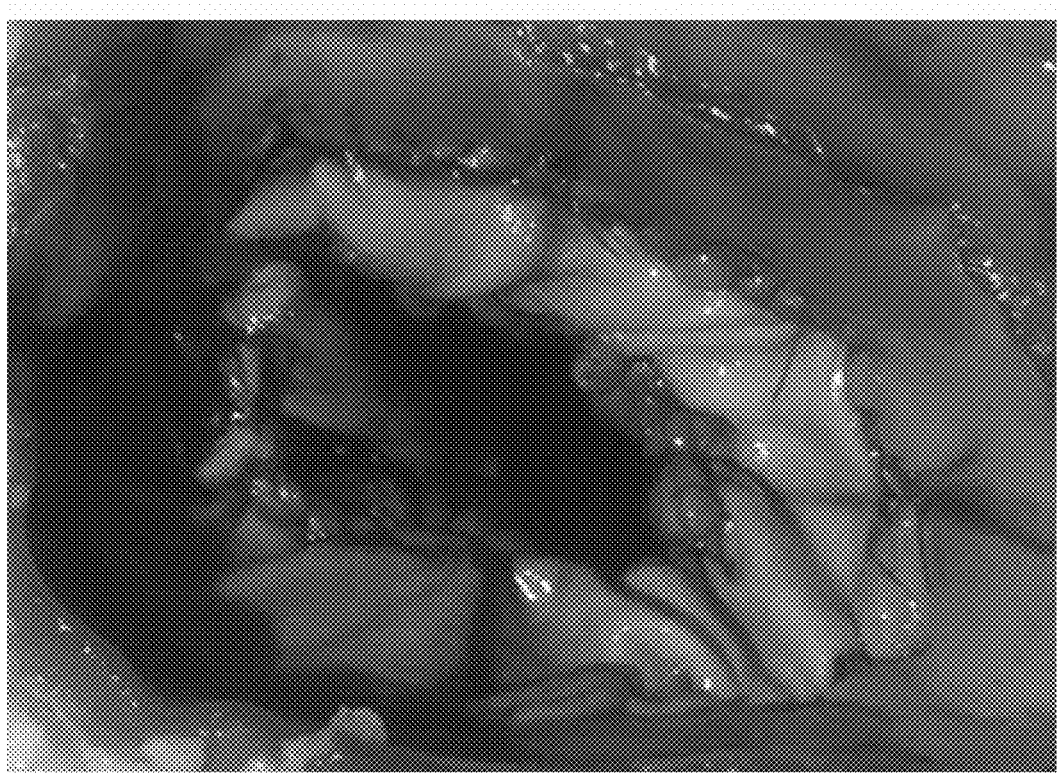

Modifications were made to reduce or prevent suture line regurgitation. The outer diameter of the collar implant is sized to fit the dimensions of the patient's annulus, forming a smaller patch diameter having a more acute patch angle (FIG. 42A). Locking sutures are used to prevent crimping (FIG. 45A, FIG. 45B). 2 mm tabs were added to the upper and lower edges of the collar to improve suturing, and horizontal mattress sutures were used to seat the collar below the annulus/leaflet (FIG. 46A through FIG. 47D).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations.

The embodiments described herein can include various combinations and/or sub-combinations of the functions, components, and/or features of the different embodiments described. Various of the above-disclosed and other features and functions, or alternatives thereof, may be combined into many other different systems or applications. Various presently unforeseen or unanticipated alternatives, modifications, variations, or improvements therein may be subsequently made by those skilled in the art, each of which is also intended to be encompassed by the disclosed embodiments.

What is claimed is:

1. An apparatus comprising:
a ring-shaped body defining an annulus end, a leaflet end, and a length running from the annulus end to the leaflet end, the ring-shaped body having an annulus portion at the annulus end and a leaflet portion at the leaflet end, axially spaced from the annulus portion;
the annulus portion having a perimeter and being configured to be attached to an annulus of a native heart valve from which a leaflet of the native heart valve has been separated; and
the leaflet portion having a perimeter equal to or larger than the annulus portion perimeter and being configured to be attached to the separated native heart valve leaflet and thereby to connect the separated native heart valve leaflet to the native heart valve annulus;
the ring-shaped body including a pleat parallel to the length, the pleat having an expandable portion extending to the leaflet end of the ring-shaped body to define in part the perimeter of the leaflet end, and a fixed portion spaced from the leaflet end, the expandable portion of the pleat being configured to be attached to the separated native heart valve leaflet.

2. The apparatus of claim 1, wherein:
the pleat is a first pleat;
the expandable portion of the first pleat is configured to be attached to the separated native heart valve leaflet;
the leaflet portion of the ring-shaped body includes a second pleat having an expandable portion extending to the leaflet end of the ring-shaped body further to define in part the perimeter of the leaflet end and a fixed portion spaced from the leaflet end, the expandable portion of the second pleat being configured to be attached to the separated native heart valve leaflet.

3. The apparatus of claim 1, wherein:
the leaflet end of the ring-shaped body has a first circumferential portion having a thickness and a second circumferential portion have a thickness different from the thickness of the first circumferential portion.

4. The apparatus of claim 3, wherein:
the separated native heart valve leaflet is a first leaflet from a plurality of native heart valve leaflets that have been separated from the native heart valve and;
the first leaflet having a first thickness and a second leaflet from the plurality of native heart valve leaflets having a second thickness, the first thickness being greater than the second thickness.

5. The apparatus of claim 4, wherein the native heart valve is a mitral valve, the first leaflet is an anterior leaflet and the second leaflet is a posterior leaflet.

6. The apparatus of claim 1, wherein the annulus end has a thickness greater than a thickness of the remainder of the annulus portion.

7. The apparatus of claim 6, wherein the annulus portion is formed of a sheet of material, the annulus end is integrally formed with the remainder of the annulus portion with multiple layers of the sheet of material.

8. The apparatus of claim 7, wherein the annulus end is formed by rolling the sheet of material.

9. The apparatus of claim 6, wherein the annulus end is formed separately from, and coupled to, the annulus portion.

10. The apparatus of claim 1, wherein the ring-shaped body is formed of biological tissue.

11. The apparatus of claim 10, wherein the biological tissue is human or bovine pericardial tissue.

12. The apparatus of claim 1, wherein the ring-shaped body is formed of at least one of decellularized tissue, polymer, or artificial fabric.

13. The apparatus of claim 1, wherein the annulus portion has a thickness different from the leaflet portion.

14. An apparatus comprising:
a ring-shaped body defining an annulus end, a leaflet end, and a length running from the annulus end to the leaflet end, the ring-shaped body having an annulus portion at the annulus end and a leaflet portion at the leaflet end, axially spaced from the annulus portion;
the annulus portion being configured to be attached to an annulus of a native heart valve from which a leaflet of the native heart valve has been separated, the leaflet portion including a pleat parallel to the length, the pleat having an expandable portion extending to the leaflet end and a fixed portion spaced from the leaflet end, the expandable portion of the pleat being configured to be attached to the separated native heart valve leaflet and thereby to connect the separated native heart valve leaflet to the native heart valve annulus.

15. The apparatus of claim 14, wherein the expandable portion of the pleat has a first configuration in which the leaflet end has a first perimeter and a second, expanded configuration, in which the leaflet end has a second perimeter greater than the first perimeter.

16. The apparatus of claim 15, wherein the annulus end has a perimeter, and the leaflet end has a perimeter equal to or greater than the annulus end perimeter when the expandable portion of the pleat is in its second, expanded configuration.

17. The apparatus of claim 15, wherein the annulus end has a perimeter, and the leaflet end has a perimeter less than the annulus end perimeter when the expandable portion of the pleat is in its second, expanded configuration.

18. The apparatus of claim 14, wherein the leaflet end of the ring-shaped body has a first circumferential portion having a thickness and a second circumferential portion having a thickness different from the thickness of the first circumferential portion.

19. The apparatus of claim 14, wherein the annulus end has a thickness greater than a thickness of the remainder of the annulus portion.

20. An apparatus comprising:
a ring-shaped body having an annulus end, a leaflet end and a length therebetween, wherein the length defines an annulus portion adjacent to the annulus end and a leaflet portion adjacent to the leaflet end and axially spaced from the annulus portion;
the annulus end having a perimeter and being configured to be attached to an annulus of a native heart valve from which a leaflet of the native heart valve has been separated;
the leaflet end having a perimeter larger than the annulus end perimeter and being configured to be attached to the separated native heart valve leaflet and thereby to connect the separated native heart valve leaflet to the native heart valve annulus; and
at least one expandable pleat within the leaflet portion of the ring-shaped body length, wherein the at least one expandable pleat runs perpendicular to the leaflet end perimeter.

* * * * *